(12) United States Patent
Nielsen

(10) Patent No.: US 6,246,330 B1
(45) Date of Patent: Jun. 12, 2001

(54) ELIMINATION-ABSORBER MONITORING SYSTEM

(76) Inventor: Wyn Y. Nielsen, 8650-6 Villa La Jolla Dr., La Jolla, CA (US) 92037-2361

(*) Notice: Subject to any disclaimer, the term of this patent is extended or adjusted under 35 U.S.C. 154(b) by 0 days.

(21) Appl. No.: 09/087,782

(22) Filed: May 29, 1998

(51) Int. Cl.[7] ................................................. G08B 21/00
(52) U.S. Cl. .................. 340/604; 605/384.1; 605/391.1; 605/573.1; 604/361
(58) Field of Search .................. 340/604, 605, 340/384.1, 384.7, 384.73, 387.1, 391.1, 573.1, 575; 381/152, 396; 604/361, 358

(56) References Cited

U.S. PATENT DOCUMENTS

| | | | |
|---|---|---|---|
| 3,460,123 | 8/1969 | Bass | 340/235 |
| 4,090,041 | * 5/1978 | Mori et al. | 179/115 R |
| 4,106,001 | 8/1978 | Mahoney | 340/604 |
| 4,163,449 | 8/1979 | Regal | 128/138 |
| 4,205,672 | 6/1980 | Dvorak | 128/138 |
| 4,356,479 | 10/1982 | Wilson | 340/604 |
| 4,356,818 | 11/1982 | Macias et al. | 128/138 |
| 4,539,559 | 9/1985 | Kelly et al. | 340/573 |
| 4,704,108 | 11/1987 | Okada et al. | 604/361 |
| 4,754,264 | 6/1988 | Okada et al. | 340/573 |
| 4,768,023 | 8/1988 | Xie | 340/573 |
| 4,796,014 | 1/1989 | Chia | 340/573 |
| 4,800,370 | 1/1989 | Vetecnik | 340/573 |
| 5,012,219 | * 4/1991 | Henry | 340/825.44 |
| 5,036,859 | 8/1991 | Brown | 128/734 |
| 5,219,341 | 6/1993 | Serbiak et al. | 604/361 |
| 5,264,830 | 11/1993 | Kline et al. | 340/604 |
| 5,266,928 | 11/1993 | Johnson | 340/604 |
| 5,392,032 | 2/1995 | Kline et al. | 340/604 |
| 5,395,358 | 3/1995 | Lu | 604/361 |
| 5,469,145 | 11/1995 | Johnson | 340/604 |
| 5,557,263 | * 9/1996 | Fisher et al. | 340/605 |
| 5,760,694 | * 6/1998 | Nissim et al. | 340/604 |
| 5,790,035 | * 8/1998 | Ho | 340/604 |
| 5,903,076 | * 5/1999 | Suyama | 310/81 |
| 5,908,411 | * 6/1999 | Matsunari | 604/361 |

* cited by examiner

Primary Examiner—Jeffery Hofsass
Assistant Examiner—Anh La
(74) Attorney, Agent, or Firm—David A. Lowin

(57) ABSTRACT

An elimination-absorber monitoring system addresses diaper-monitoring problems with a unique, low cost, multi-layer disposable sensor structure that absorbs small volumes of urine, yet allows most urine volume to flow unimpeded through it, and into the diaper below. When connected with a reusable, miniature monitor/indicator unit, the sensor presents a clear and on-going change of measurement condition upon experiencing a rapid influx into the diaper of a significant volume of urine, and/or upon a significant reduction in the available absorbency of the diaper's top surface. The sensor additionally provides recessed, protected elements for similarly presenting a clear and on-going change in measurement condition upon experiencing the presence of fecal matter. Further provided is the monitor unit employing narrow, widely-spaced, fast rise-time, fast transition-time pulses for conductivity measurement and alarm activation. The monitor and sensor are interconnected and attached to a diaper by particularly effective and unique means, and the monitor is equipped with a highly intuitive and convenient control interface, as well as improved assemblies for the transmission of audible and visual alarm indications. Also described is a convenient test-strip device which, when connected to the monitor/alarm unit of the system, can selectively simulate either a soiled or unsoiled elimination-absorber/sensor for test, caregiver-training or demonstration purposes.

43 Claims, 33 Drawing Sheets

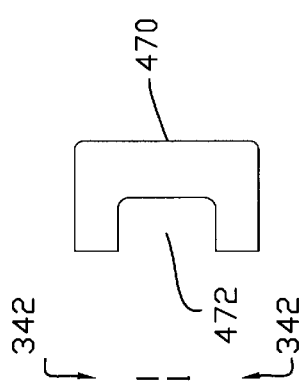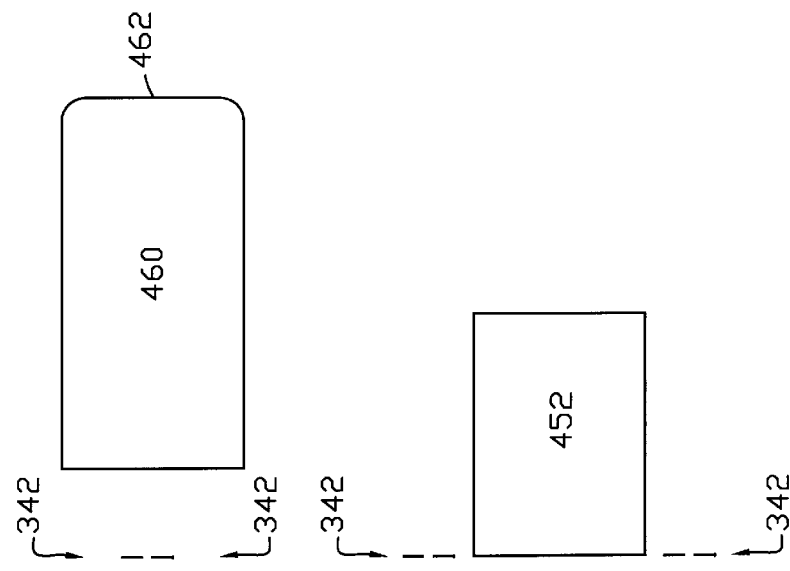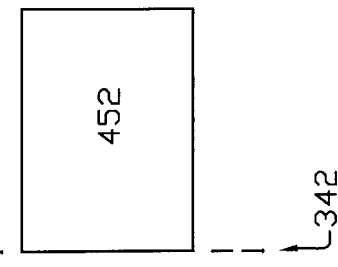
FIG. 9
FIG. 8
FIG. 7

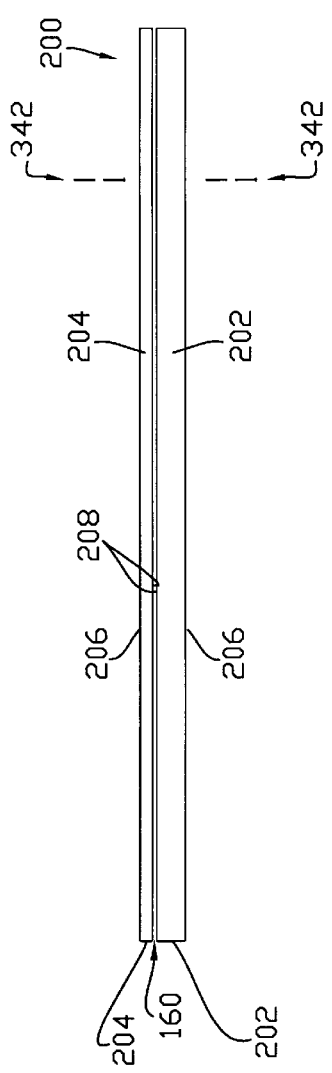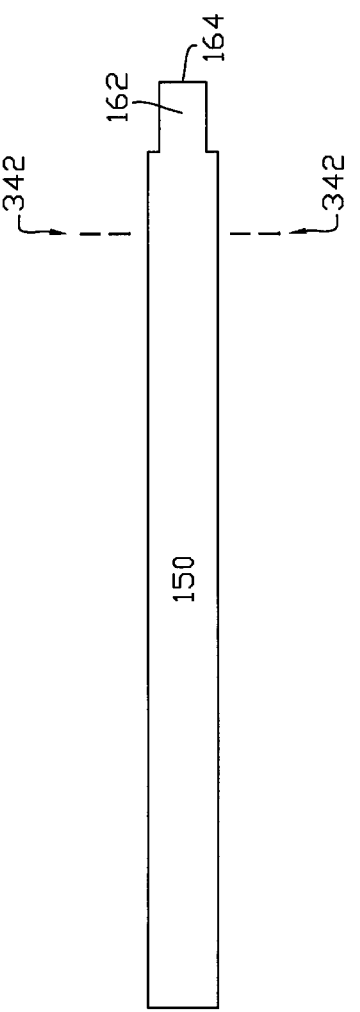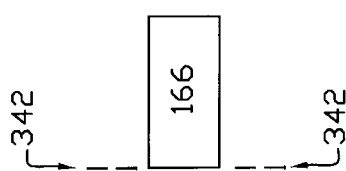

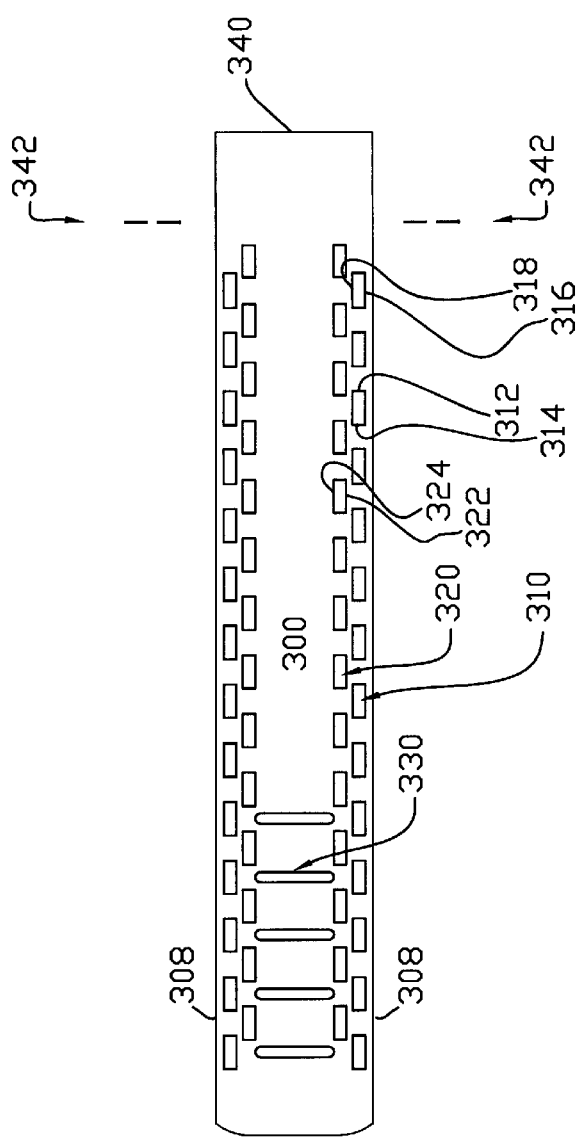
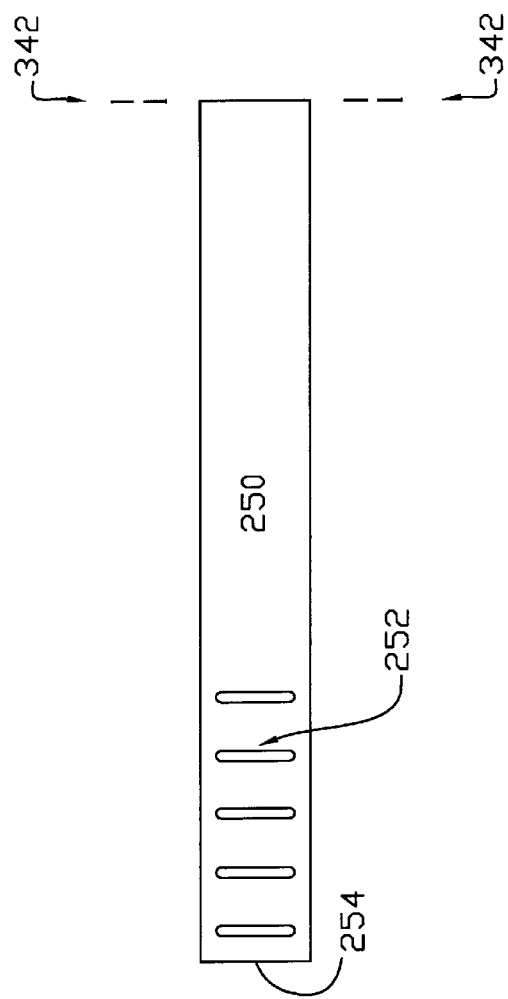

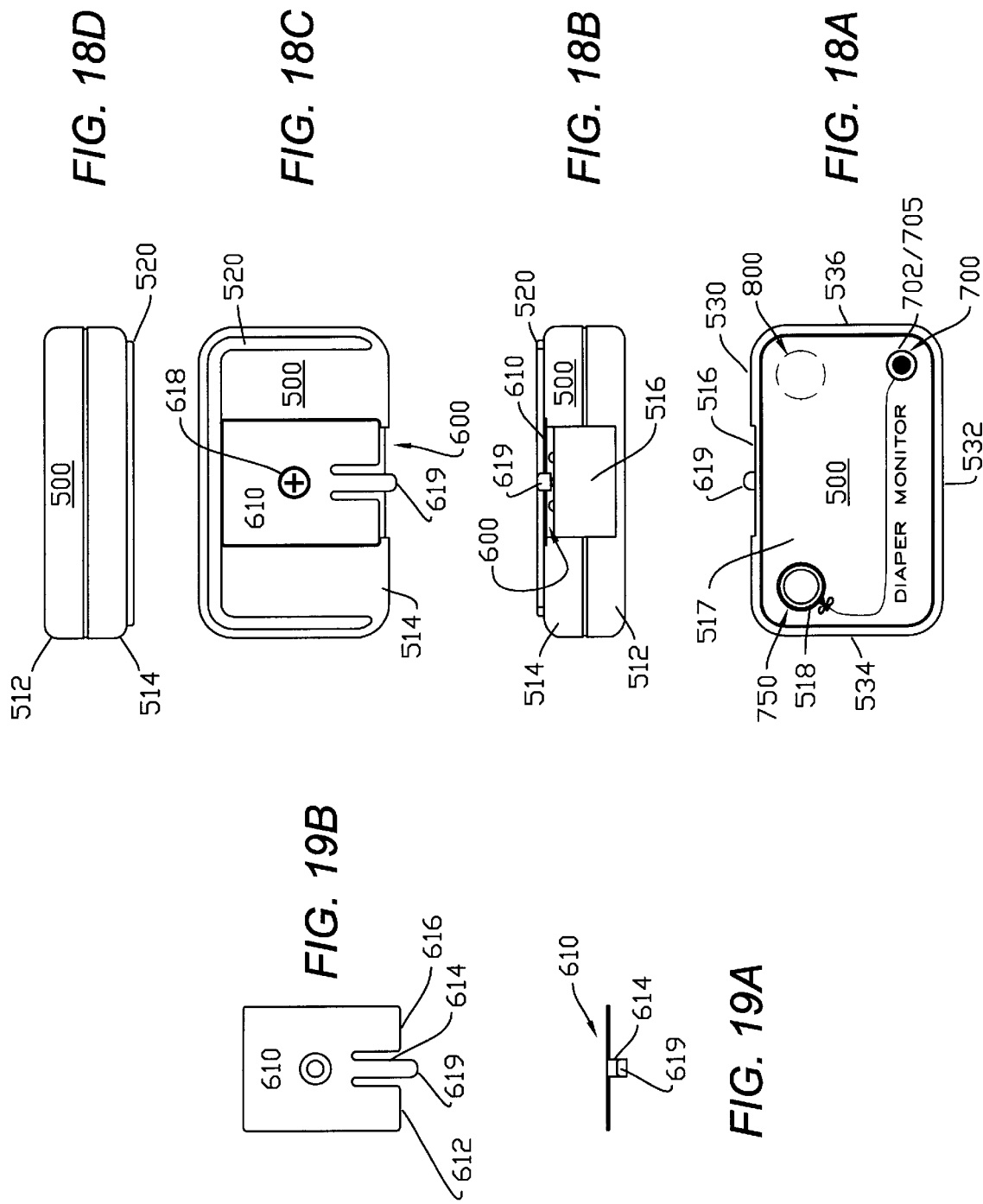

ELIMINATION-ABSORBER MONITORING SYSTEM

FIELD OF THE INVENTION

The present invention relates to systems and devices for monitoring the condition of a diaper, other undergarment, bedding or the like; particularly with regard to the clean or soiled status thereof, and specifically to a sensor and monitor/alarm assembly useful as an elimination-absorber monitoring system.

BACKGROUND INFORMATION

Inventors have long sought to provide a system of associated devices for effectively monitoring the condition of a diaper, other undergarment, bedding or the like. While the present invention provides an elimination-absorber monitoring system useful in each of these environments, a preferred embodiment is utilized in conjunction with a disposable diaper. Thus, for purposes of brevity in the present specification, the term "diaper" shall indicate any of the above-described use environments, except where otherwise specifically stated or apparent from context.

The art is replete with examples of prior attempts to satisfy the need for an elimination-absorber monitoring system. Each has, for one reason or another, apparently failed to achieve significant implementation and consumer acceptance. Upon review, the prior systems appear either impractical, unsuitable to the use environment, unworkable and/or uneconomical—largely for one or more of the following reasons: failure to provide an appropriate sensor response or alarm criteria with respect to urine-soiling; inability to detect fecal matter, or to provide an appropriate sensor response or alarm criteria with respect to feces-soiling; lack of important user-oriented features; and unsuitability to cost-effective manufacturing.

PRIOR ART

Most previous systems have utilized the measurement of electrical conductivity between two spaced electrodes disposed somewhere on top of, within, or under the absorbent layers of a diaper, to detect the presence of liquid urine when it bridged some path between the electrodes. This approach is described in U.S. Pat. No. 3,460,123 (Bass), U.S. Pat. No. 4,356,818 (Macias), U.S. Pat. No. 4,800,370 (Vetecnik), U.S. Pat. No. 4,539,559 (Kelly), U.S. Pat. No. 4,768,023 (Xie), U.S. Pat. No. 5,036,859 (Brown), U.S. Pat. Nos. 5,264,830 and 5,392,032 (Kline), U.S. Pat. No. 4,205,672 (Dvorak), and U.S. Pat. Nos. 5,266,928 and 5,395,358 (Lu). These systems all depended on the relatively high conductivity of urine, as compared to the typically low conductivity of unsoiled, dry diaper materials. Several of these prior inventors clearly assumed that the key to a useful "diaper wetness" alarm (as their objective was often termed) would be the detection of virtually any urine in a diaper. They also recognized that, depending on the sensor configuration, urine could miss the intended target. Thus, variations of this approach incorporated either distributed (e.g., screen-like) electrodes or various absorbent pads or modifications of a diaper to help collect, funnel or direct urine flow to bridge the sensing electrodes, e.g., U.S. Pat. No. 4,356,818 (Macias). However, this focus on the detection of simple "wetness" resultant from urination—as opposed to the far more useful determination that an elimination-absorber actually required changing—failed to answer the real needs of caregivers and diaper-wearers. As with all the prior systems, seemingly little emphasis was placed on defining and obtaining truly user-responsive sensor performance. While this simple "wetness detection" focus may have appeared somewhat workable, as applied to certain cloth or early low-absorbency diapers, it did not adequately address the effects of widely differing flow-rates and volumes in various urination events and situations. Moreover, for reasons that shall be explained below, this approach was completely incompatible with the properties (and particularly the much greater capacity) of modern disposable diapers. Thus, previous systems based on simple "wetness detection" typically either failed to work consistently, or were prone to meaningless or premature alarm indications.

Some prior attempts took the view that a "soiled" diaper condition could be deduced by simply detecting the arrival of urine at the bottom (just inside the outer cover) of a diaper, i.e., that this would indicate when the diaper had reached its absorbent capacity. However, high-absorbency diapers are specifically designed to prevent urine from soaking to the outer cover, at least during the expected wearing time. Because urine permeates into and through a diaper with at least some time delay, additional urine will continue to collect after it first reaches a pair of sensing electrodes. If urine is detected only after soaking to the bottom of a diaper, the continued accumulation will tend to quickly spread along the inside of the cover, and quite likely leak out before the diaper can be changed. Thus, the determination of a fully saturated condition based on the sudden presence of urine at the bottom layers is not practically useful. Even completely non-electronic approaches to diaper monitoring, such as the "happy face" visual indicators incorporated into the outer cover of Fitti™ brand diapers, can similarly suffer from the limitations of over-simplified alarm criteria and inappropriate, inconsistent, or untimely sensor response. Also, such purely visual wetness-indicating devices, which are necessarily disposed directly on a diaper cover, have limited value for other reasons. Just as with traditional methods, they still require frequent and continual checking by a caregiver—and the awkward removal of clothing layers worn over a diaper—to permit viewing of the indicator. They thereby fail to provide a convenient, automatic, attention-getting signal that a diaper needs changing.

Still other inventors tried to "intercept" the flow of urine somewhere in the mid-layers of a diaper, but as will be appreciated by those skilled in the art, another problem results from the modern disposable diaper being such an aggressive absorber. No choice of conductivity-sensing path within such diapers (including midway through the absorbent layers) is likely to conveniently go from "dry" to fully "wet" at such time as to appropriately reflect a "needs to be changed" condition. In some such diapers, "super-absorbent" particles or polymer jells have been used to dramatically increase the liquid-holding capacity in a central core of the absorbent structure. These central absorbers are typically surrounded by conventional (e.g., cellulose based) absorbent wadding because the super-absorbers tend to react relatively slowly in absorbing liquid, as compared to the conventional materials. This means that the distribution of liquid through the diaper is highly non-uniform and it changes markedly after a urination event, as the super-absorber core gradually pulls liquid out of the conventional absorbent bulk. Also, with intermediate levels of moisture in any type of diaper (where the absorbent material is not yet completely saturated), urine can accumulate gradually or unevenly—often separated into discontinuous droplets or unpredictably scattered wet or merely damp regions. Thus, these regions may not happen to span a chosen path between electrodes so that the urine can be reliably detected. Moreover, the mere presence of relatively high conductivity (and hence the presence of liquid) along any given path through a diaper may not reflect a true "needs to be changed" condition (i.e., correlate with caregiver expectations or with traditional diaper inspection methods), particularly in the case of modern high-absorbency, disposable diapers. As explained above, none of the foregoing simple conductivity-based systems reflected a truly appropriate sensor response or "alarm criteria" with respect to urine-soiling of diapers. They typically responded either immediately or prematurely to the presence of trivial amounts of urine passing into a diaper; or alternatively, they responded either inconsistently, or not until after the diaper was soaked beyond its safe absorbent capacity—depending primarily on the choice of sensing location.

Other prior devices have measured AC-conductivity (or related electrical capacitance) across a bulk volume of diaper absorbent material, to achieve more appropriate alarm indications, e.g., U.S. Pat. Nos. 4,704,108 and 4,754,264 (Okada). These methods employed indirect determination of the average "moisture content" or "dampness" in some portion of the diaper absorber. This indirect determination was based on the presumed proportionality of average dampness to directly-measured capacitance or AC-conductivity. Proponents of this approach held that an accurate measurement exceeding a certain fixed threshold value would indicate a urine-soiled condition. They also held that such would be appropriate and sufficient to determine that a diaper needed changing. To be even partially correct, however, this assumption required that the portion of absorbent material actually measured be truly representative of the average dampness in the entire absorber volume. Also for meaningful measurements, that portion would have to be held in a constant shape and position, relative to the sensing means. Furthermore, selecting an appropriate fixed threshold value (that would remain valid with different sizes and applications of diapers) may not be possible. Thus, making sufficiently accurate and meaningful measurements (under all expected conditions) presented serious and unanswered practicality problems. These problems result from variations in measurable conductivity or capacitance due to many factors such as high humidity, perspiration, residual dampness from the washing of soiled skin, and the relative movement and random compression of the absorber as the wearer shifts position—all of which are likely to be experienced in the use environment.

In U.S. Pat. No. 5,469,145 (Johnson), the use of capacitive coupling of a sensing circuit (disposed on the outside of a diaper) to the material to be measured (inside the diaper) eliminated all direct connection between the monitoring device and the inside of a diaper. However, the described relatively high-impedance capacitor input to a monitor circuit would likely be particularly prone to external electrical noise and interference, as well as to significant capacitance variations due to unpredictable moisture distribution, the presence of other nearby conductive surfaces and physical movement—as the diaper wearer actively and continually shifts position. In short, all the previously described difficulties associated with other distributed dampness measurement approaches would tend to be worsened with the sensing elements moved farther away from the measurement volume. In addition, the use of continuous sinusoidal AC signals for sensing also typically entails greater energy consumption than does the use of DC conductivity methods. In prior systems this has required either the recharging or replacement of batteries, and thus complicated or precluded the use of a permanently sealed monitor unit.

Moreover, the prior systems were all ineffective for detecting the feces-soiling of diapers. Only a minuscule change in DC-conductivity or absorbent-bulk AC-conductivity (or capacitance) results from a small quantity of fecal matter on the surface of a diaper. This has rendered it typically undetectable by prior methods relative to much larger background changes produced by many of the above-described factors in the use environment. In general, the prior devices' collective inability to reliably detect feces stems from both the physical nature of the sensors and the electronic systems employed with them.

As described above, prior electronic systems have measured either DC or AC-conductivity or capacitance to detect urine. DC systems for accurately measuring liquid ionic conductivity typically require some "latching" means (such as circuits which detect an initial event and then remain "triggered"), because the applied electric field used for measurement causes dissociation of the very ions that enable electrical conduction, thus decreasing the measured conductivity over time. This effect poses only a minor problem when liquid urine directly bridges two closely spaced contacts, because the sudden initial increase in conductivity is substantial (due to the relatively high uric acid ionic concentration in urine) and this sudden increase can be easily differentiated from the baseline "dry diaper" condition. However, neither proportional bulk moisture content distributed in a diaper, nor the presence of feces, are suitable for direct DC-conductivity measurement. Particularly with feces, the ionic concentration is much lower than with direct liquid urine contact—and the water content, which allows the ions mobility, is often much lower in semi-solid waste. If a steady-state voltage is applied in an attempt to detect feces by inducing a DC current, the ionic dissociation effect results in rapid reduction in measured conductivity. With DC sensing of urine, a reference alarm threshold can be chosen such that the alarm condition will persist for a reasonable time—but probably not in all cases. This approach does not work at all with feces, however, because the initial conductivity is so low—and the decrease is so rapid—that after mere seconds, the conductivity falls below a practically measurable level. If a "latching" electronic detector is used to circumvent this problem—and is made sufficiently sensitive for detection of feces—this type of circuit may be easily triggered by momentary and insignificant conditions. Should this occur in actual use situations with a diaper monitoring system, caregiver intervention would likely be required to reset it. Because the true state of the diaper could not, in such cases, be reliably determined (without reverting to traditional diaper inspection), latching-type detectors are undesirable for use in elimination-absorber monitoring systems.

An additional problem is presented by the appropriate alarm criteria for feces-soiling. Since a diaper does not absorb feces and carry it away from direct contact with the skin (as it does with urine), and particularly given the irritation resultant from prolonged contact, feces must be detected virtually at the diaper surface—and a feces-soiled diaper needs to be changed as quickly as is practical. Obviously, for feces detection purposes, the various prior AC bulk-dampness type of sensors were not useful, as their sensing elements focused on a bulk volume of a diaper, not on its surface. On the other hand, a sensor structure involving exposed electrodes placed on the top surface of a diaper, while not only disconcerting to a caregiver, would prematurely respond to the presence of any urine. Such arrangement would also greatly increase the likelihood of false alarms resulting from bridging of the electrodes through either AC-coupling, or direct contact with skin, particularly if damp. As discussed above, feces are relatively very low in conductivity, and are thus difficult for such a system to reliably detect in the use environment. The overall elimination-absorber feces-detection problem is even more difficult, because a truly practical system must effectively combine the determination of both feces and urine-soiling of diapers. Clearly, no prior system has successfully done so.

OBJECTS AND ADVANTAGES OF THE INVENTION

In contrast to the previous devices and methods, in an aspect of the present invention the appropriate "alarm criteria" and detection methods reliably establish that:

1) a significant volume of urine has been rapidly discharged into a diaper and/or,
2) a diaper's remaining ability to absorb has been significantly reduced and/or,
3) any feces has been deposited into a diaper.

The above conditions are defined and automatically detected so as to appropriately correlate with traditional perceptions of when a modern, high absorbency diaper should probably be changed. This response not only reflects the criteria of conventional checking, but it leads to diaper-changing at similar intervals.

Other requirements, identified and provided in the present invention for a disposable elimination-absorber monitoring sensor, pertain to its "feel", appearance and cost. The sensor is comfortable for the wearer, whether incorporated into a diaper or applied to its inner surface before use. It is soft, flexibly compliant and pleasing in appearance. From a cost standpoint, the materials are particularly economical and the sensor design is specifically oriented toward high-speed manufacturing processes such as continuous-strip based assembly methods.

In addition to providing a sensor system that consistently determines "diaper needs changing" conditions (with respect to both urine and feces soiling) in a manner responsive to the needs of both caregiver and wearer, the present invention additionally addresses certain practical problems with the prior approaches and critical needs that have remained unanswered. The monitor unit produces a relatively pleasant audible alarm that can be heard from a reasonable distance over typical background noise and is compatible with common remote audio baby monitors. Audible alarms, however, are not desirable for night and nap use (or in certain public situations), so an alternative (e.g., visible) alarm that is designed to not disturb a sleeping infant or surrounding people is also provided. The visible alarm is bright enough to be readily seen outdoors in daylight, or through one or more layers of clothing, and over wide viewing angles. Moreover, a caregiver can easily switch the monitor unit between alarm modes, and can do so with one hand, even through the wearer's clothing without needing to remove it. Re-usable monitor units for elimination-absorber monitoring systems will inevitably become exposed to moisture and, when soiled, require cleaning. They are also likely to occasionally be dropped onto hard surfaces while being routinely handled. Thus, a compact, rugged, waterproof case is needed to house the monitor unit circuitry, switching means, and visible and audible alarms and to provide physical and electrical connection to a diaper and sensor. A fully sealed case potentially limits or altogether precludes access for battery recharging or replacement, however, thereby complicating the power requirements for such a device. Therefore, the monitor unit's energy use must be sufficiently miserly for the complete system to be powered throughout its expected lifetime using a single, pre-installed battery. Additionally, a sealed monitor case can also inhibit audible and visual alarm signal transmission as well as complicating the reliable and convenient interconnection of the monitor unit with a disposable sensor. Thus, the system employs innovative means to effectively overcome these problems. The monitor unit attaches to, and can be removed from, the disposable sensor and diaper quickly and easily. It remains securely positioned and electrically connected while in use. A self-test indication of proper operation is automatically given when the system is activated (by means of simply attaching it to a disposable sensor/diaper). This self-test indication also confirms the mode (audible or visible) to which the monitor is set.

The absence of any widely marketed consumer product for elimination-absorber monitoring further highlights the unsuitability of prior inventors' attempts. Today's parents and caregivers are still embarrassed by sniffing our kids and pulling their pants down in public to see whether they need to be changed. Thus, the desire remains for a truly effective, economic, safe, reliable, convenient, and energy efficient system for use with infants and other individuals dependent on a caregiver. These and other objectives, as will become apparent from the following specification and drawings, are satisfied by the present invention.

SUMMARY OF THE INVENTION

A sensor, for use with an elimination-absorber monitoring system, has sensing means and a flow-baffling layer disposed to preclude direct flow of a liquid to be sensed onto the sensing means. The sensor can also have a first liquid-permeable flow-conducting layer disposed adjacent the flow-baffling layer, opposite the sensing means, to collect and conduct a liquid to be sensed across said flow-baffling layer. A second liquid-permeable flow-conducting layer can be disposed adjacent the flow-baffling layer, opposite the first flow-conducting layer, to conduct liquid from the first flow-conducting layer, around the flow-baffling layer and toward the sensing means. In a preferred embodiment, the sensor has a second relatively liquid-impermeable layer disposed opposite the flow-baffling layer, with respect to the sensing means and the second flow-conducting layer, to form a capillary channel within the sensing means.

In a further preferred embodiment, the sensor has a first series of openings through and disposed toward the outer edges of the flow-baffling layer to conduct liquid from the first flow-conducting layer, through the flow-baffling layer and to the second flow-conducting layer, and a second series of openings through the flow-baffling layer, disposed between the first series of openings and the outer edges of the flow-baffling layer to conduct liquid from the first flow-conducting layer, through the flow-baffling layer, to the elimination-absorber. In this embodiment, the second flow-conducting layer is sufficiently wide to communicate with the first flow-conducting layer through the first series of openings, but not through the second series of openings. It is disposed between the flow-baffling layer and the sensing means. The relatively liquid-impermeable layer is sufficiently wide to preclude direct flow between the sensing means and the elimination-absorber.

In another embodiment of the sensor the second flow-conducting layer is preferably selected from a material that is less absorbent than a dry elimination-absorber, but more absorbent than an elimination-absorber sufficiently wetted to require replacement. The second flow-conducting layer is configured in size and materials to delay the conduct of the liquid from the first conducting-layer to the sensing means until the elimination-absorber is sufficiently wetted to require replacement.

In yet another embodiment of a sensor for use with an elimination-absorber monitoring system, the sensor has a layer, sensing means disposed beneath the layer and a series of openings through the layer, the openings being of sufficient size, shape and thickness to permit the passage of feces to contact the sensing means, while deterring contact between the sensing means and the skin of a wearer of the elimination-absorber. It is preferred that the openings be disposed posterior to the sensor portion most likely to be directly impacted by a drop or stream of urine, and that the layer be sufficiently absorbent to retain and thereby prevent small volumes of liquid or condensation from penetrating the openings and being detected by the sensing means. The liquid-impermeable layer is preferably relatively hydrophobic as compared to the absorbent layer, even when the absorbent material becomes saturated, and the absorbent layer can be bounded by the liquid-impermeable layer to direct the flow of liquid away from the openings. It is preferred that a cover layer be disposed adjacent to the layer opposite the sensing means, the cover layer having nominally closed slits/flaps covering the openings. These slits/flaps are resistant to passage of urine but displaceable by contact with feces to permit the passage of feces into the openings.

The sensor of the present invention can be incorporated as part of a disposable diaper or adapted for application to an elimination-absorber, in which embodiment there are provided means for affixing the sensor to the elimination-absorber, and an optional cover layer for separating the first flow-conducting layer from the skin of a wearer of the elimination-absorber.

In still another embodiment of the invention, there is provided a monitor/alarm unit retainer for use with an elimination-absorber monitoring system, the retainer having an interlocking protrusion and receiving portion respectively disposed on either an elimination-absorber/sensor or an elimination-absorber monitor, the elimination-absorber/sensor having an elastic or semi-elastic flap adapted to be stretched over the monitor/alarm unit and releasably adhered to the elinination-absorber. The retainer is preferably employed with the releasable circuit electrical connector of the invention, which includes a flexible-tab portion and a tab-receiving portion. The tab portion has two or more conductive members disposed on a resilient support. The tab-receiving portion has two or more protruding contacts arranged to engage the conductive members, lateral surfaces for guiding and positioning the tab, and has means to deform the resilient support thereby retaining the tab portion while maintaining its orientation and pressure against the contacts to ensure continuous electrical connection of the conductive members with the contacts. This connector has applicability in widely varying environments and systems, and is not intended to be limited to application with the elimination-monitoring system of the invention.

Also provided is an elimination-absorber monitoring system kit including one or more of any of the sensors of the invention with a monitor/alarm unit, and preferably including a test strip for use in confirming proper function of the system. The monitor/alarm unit preferably includes a power source, an alarm means, an interlocking protruding or receiving portion corresponding with the portion on the monitor/alarm unit retainer, a releasable sensor connector (as described above), and electronic circuitry employing relatively narrow, relatively low duty-cycle pulses to measure conductivity or capacitance between a pair of spaced conductors or semiconductors that are disposed within or that span an appropriate measurement path relative to the elimination-absorber to be monitored and actuates the alarm means when the elimination-absorber requires replacement. The monitor/alarm unit forms a separate aspect of the present invention. It is preferably provided within a waterproof case enclosing the power source, the alarm means and the electronic circuitry. The releasable sensor connector is preferably fabricated as part of the case. The case has control surfaces with access for the alarm means and control means, the access being sealed by a thin, at least partially flexible membrane.

In another aspect of the invention there is provided visible alarm means including an electro-optical source disposed in a through-opening that is sealed by a relatively thin, substantially optically-permeable covering. In a preferred aspect, disposed above the visible alarm means covering is a removable or repositionable, relatively thin, light-transmissive, protective or retaining covering layer, flap or pocket of material above. The flap significantly protects, retains and positions the monitor/alarm unit and acts as a rear-projection screen for the electro-optical source, dispersing or de-focusing the relatively narrow light beam from an electro-optical source into a significantly wider beam or viewing angle than that of the source.

In still another aspect, audible alarm means are located behind a shallow recess in the case disposed behind an audibly transmissive, relatively thin flexible membrane with a sound permeable, structurally supportive, relatively rigid, perforated bottom. The recess allows the membrane to vibrate freely in response to acoustic pressure waves from an electro-acoustic transducer disposed behind the recess but which limits the maximum deflection of the membrane to within its elastic limit thereby protecting the membrane from mechanical damage without excessively attenuating the sound transmission from the transducer during intended operation.

Control means are provided, disposed through a surface of the case. The control means both changes and indicates the alarm or indicative function selected for the system's operation in response to repeated actuation, where the indication is by means of the visible or audible alarm to emit a representative signal. The control means preferably provides such indication only upon proper connection of an elimination-absorber sensor through the releasable sensor connector.

Also described is a convenient test-strip device which, when connected to the monitor/alarm unit of the system, can selectively simulate either a soiled or unsoiled elimination-absorber/sensor for test, caregiver-training or demonstration purposes.

BRIEF DESCRIPTION OF THE DRAWING FIGURES

FIG. 1 is a top plan view showing the two main elimination-absorber monitoring system components, i.e., a disposable sensor and a reusable monitor/alarm unit. For purely illustrative purposes, these components are shown arranged in linear fashion atop the sensor's protective packaging layer as employed in a preferred, disposable add-on embodiment of the invention. Although a sensor is shown with the monitor unit already interconnected, these components would normally not be combined prior to installation of the sensor on a diaper. Sensors are intended to be pre-installed on diapers, after which the monitor unit is attached when a diaper is needed.

FIG. 2A is a perspective illustration of a preferred embodiment of the system with the sensor installed as an add-on to a disposable diaper. The sensor's strippable top protective layer is shown to the right, as if just removed from the area of the sensor that is folded over the top front of the diaper. Also shown is the reusable monitor unit, as if poised for connection and attachment to the sensor-equipped diaper.

FIG. 2B is a perspective illustration of the system as shown in FIG. 2A, where the monitor unit has been connected to the sensor and secured to the front of the diaper, ready for use.

FIG. 3 is a top plan view, showing the various superposed layers of the sensor, including its connection and retention means. The sensor is shown disposed linearly, as if laid out on a flat surface, with both top and bottom protective layers removed. The horizontal scale of the figure and the dashed fold line correspond to FIG. 1 and to FIG. 4. In FIG. 3, as well as in most following views of the sensor and its components (but not, of course, in the cross-sectional views), the relative position of the sensor fold line is shown for reference.

Figure 3:
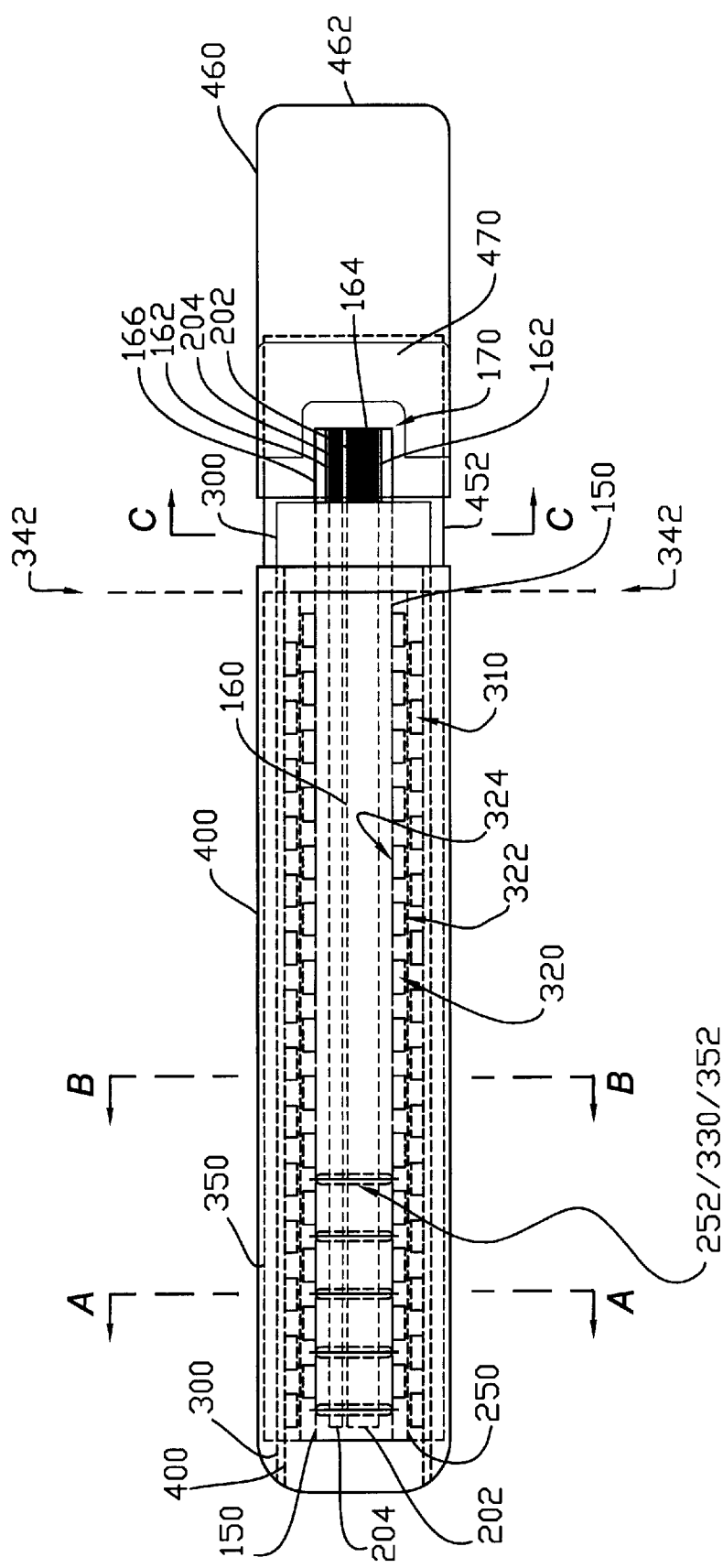
FIG. 3A is a close-up cross-sectional view in elevation taken along line A—A in FIG. 3 (but magnified in scale), showing an embodiment of the feces-responsive structural features of a sensor.
FIG. 3B is a close-up cross-sectional view in elevation taken along line B—B in FIG. 3 (but magnified in scale), showing an embodiment of the urine-responsive structural features of a sensor.
FIG. 3C is a close-up cross-sectional view in elevation taken along line C—C in FIG. 3 (but magnified in scale), showing an embodiment of the portion of a sensor that is disposed just outside and on the top front of a diaper when installed for use. For clarity, the sensor's monitor unit locating block is not shown.
Figure 4:
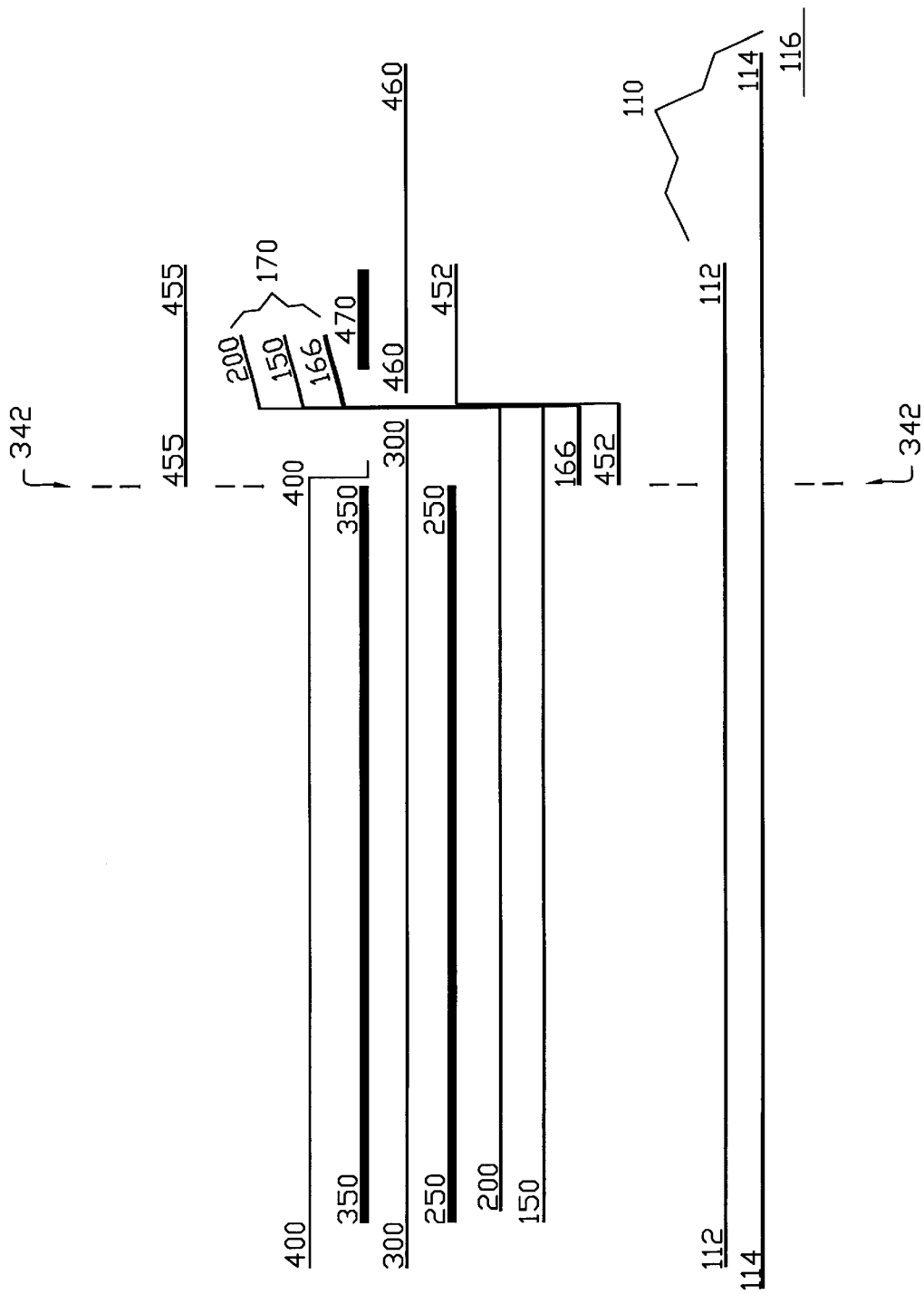

FIG. 4 is a side (edge) view in elevation of a complete, preferred add-on embodiment sensor showing all layers. The thickness and vertical separation of each layer is exaggerated, to clarify its relative position and length. The horizontal scale of FIG. 4 and the dashed fold line both correspond to FIG. 1 and to FIG. 3.

Figure 5A:
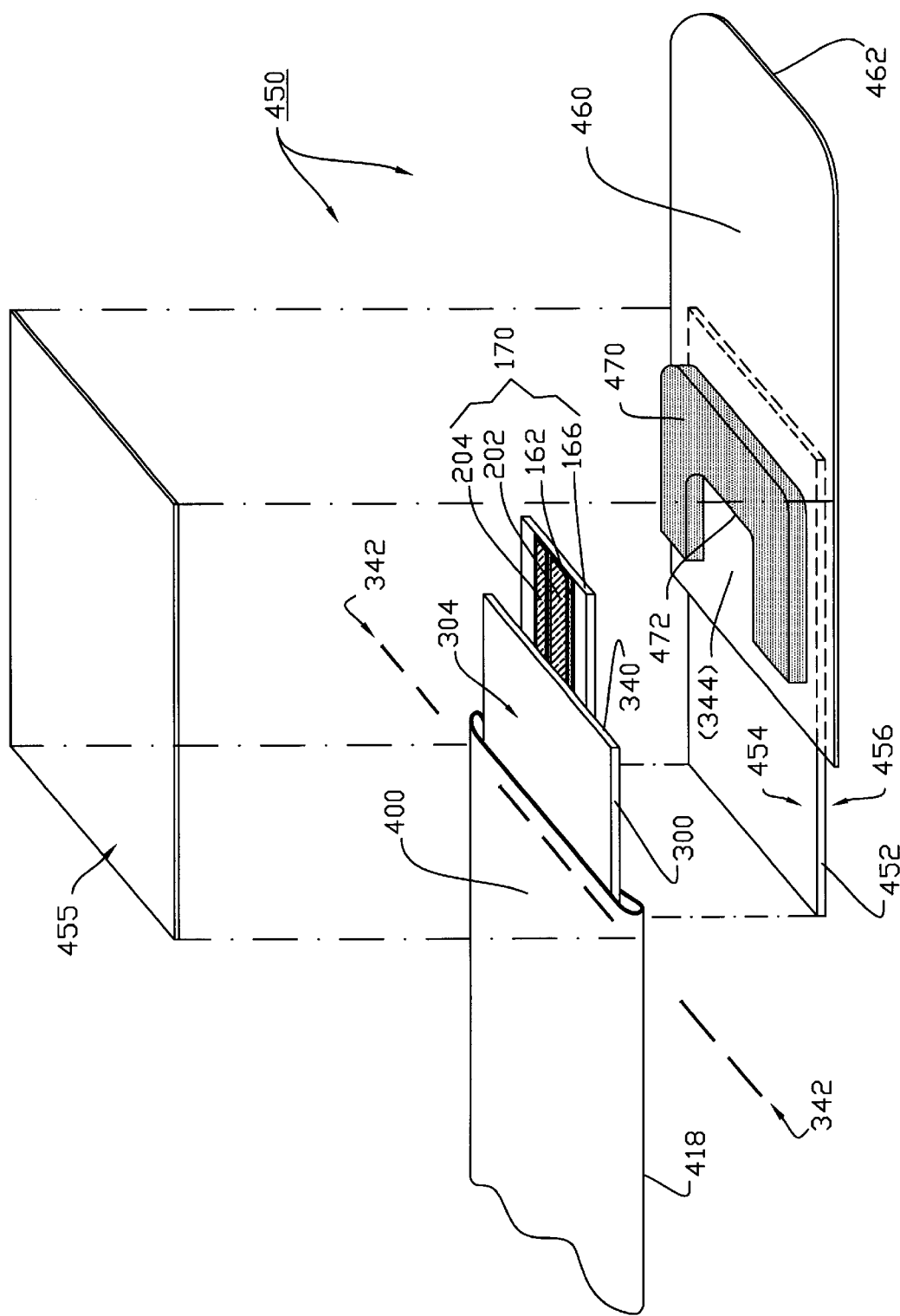

FIG. 5A is a close-up "exploded-view" perspective illustration of the monitor connecting/locating/retaining portion of the elimination-absorber sensor. (The removable bottom protective layer is not shown.)

Figure 5B:
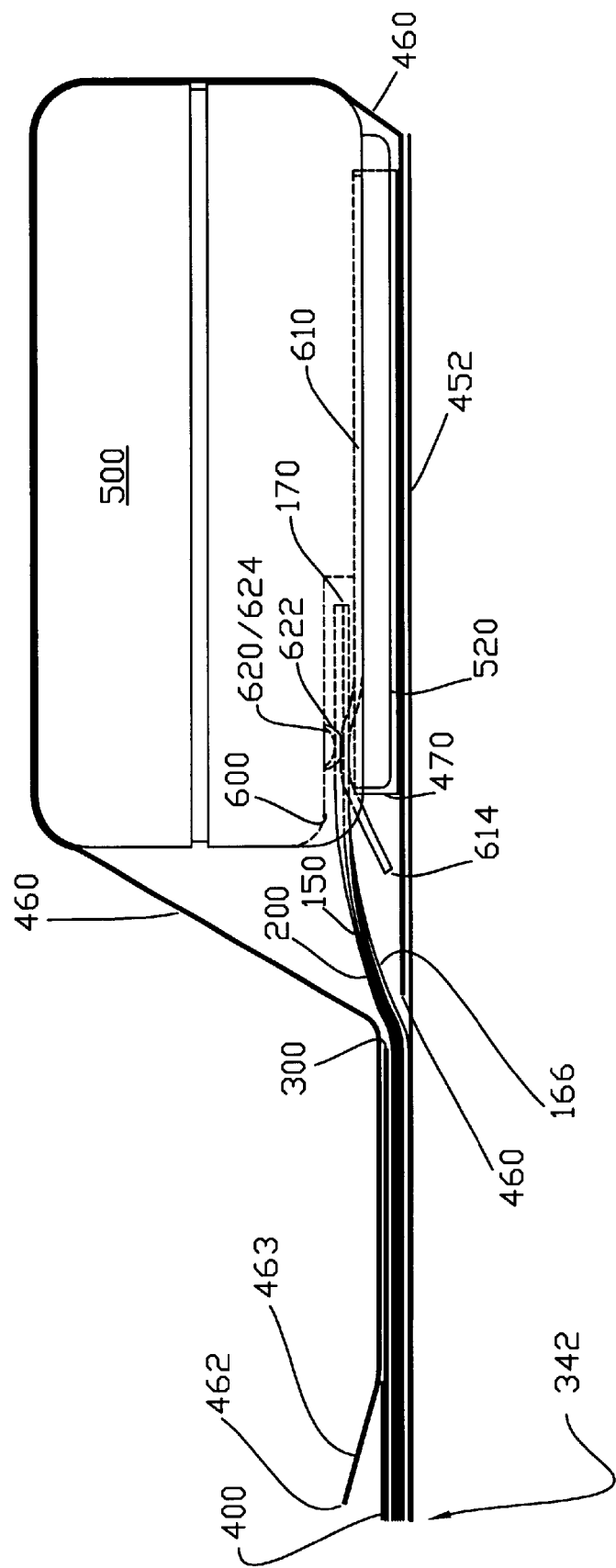

FIG. 5B is a close-up side view of a preferred embodiment of the reusable electronic monitor unit, shown mated to the monitor connecting/locating/retaining portion of the sensor. For clarity, the diaper itself and the in-diaper portion of the sensor beyond the fold line (to the left) are not shown. Hidden (dashed) lines indicate the tab connector portion of the sensor as inserted into the connecting portion of the monitor unit, and how a preferred type of locating block of the sensor is captured under the monitor case. Also shown is the sensor flap portion wrapped around and over the monitor to retain it on the top front of the diaper.

Figure 6:
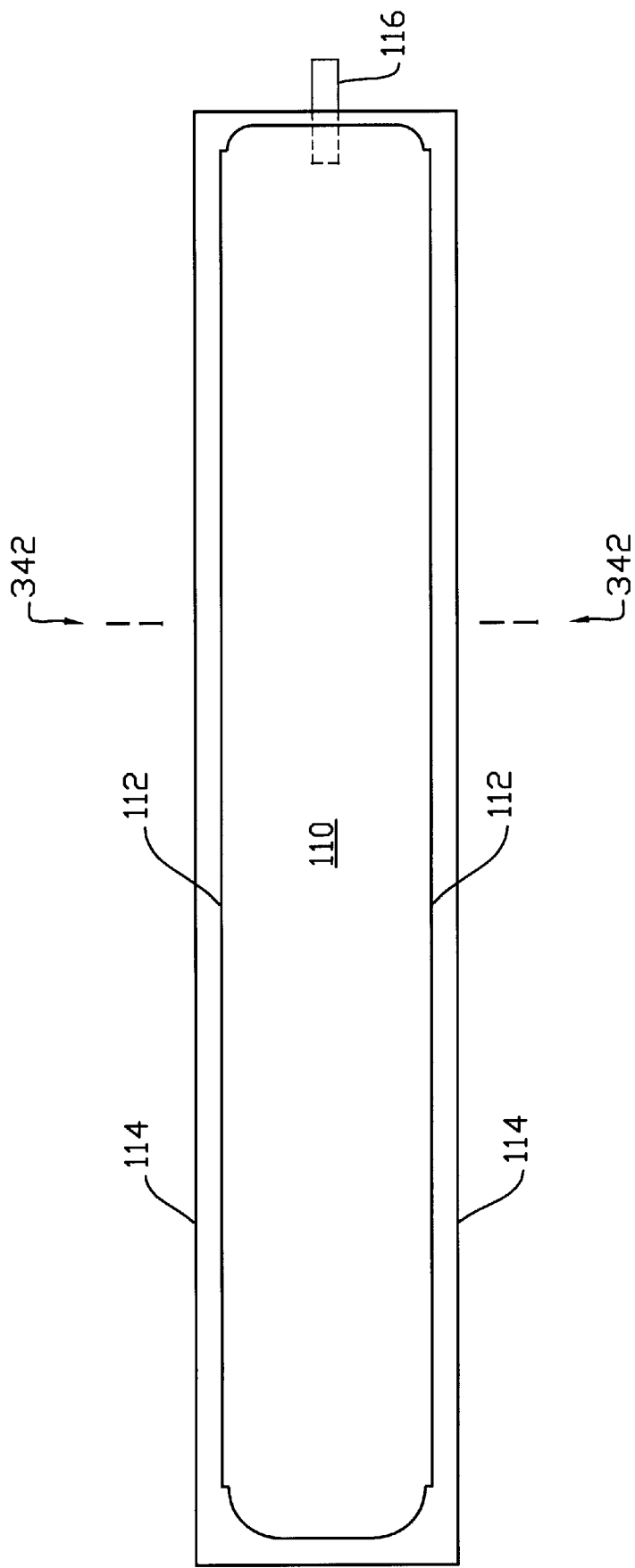

FIG. 6 is a top plan view of the removable bottom protective layer.

FIG. 7 is a top plan view of the lower connecting/ attaching layer of the coupling and retention portion of the sensor.

FIG. 8 is a top plan view of the monitor unit retaining flap layer of the sensor.

FIG. 9 is a top plan view of the monitor unit locating block of the sensor.

FIG. 10 is a top plan view of the reinforcing connector tab of the sensor.

FIG. 11 is a top plan view of the lower impermeable layer of the in-diaper portion of the sensor.

FIG. 12 is a top plan view of elements of the sensor's electrically conductive layer.

FIG. 13 is a top plan view of the lower sensor absorbent layer.

FIG. 14 is a top plan view of the sensor substrate (upper impermeable) layer.

Figure 15:
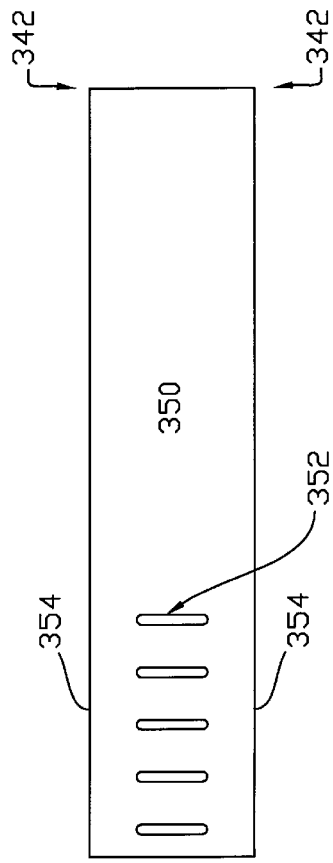

FIG. 15 is a top plan view of the sensor upper absorbent layer.

Figure 16:
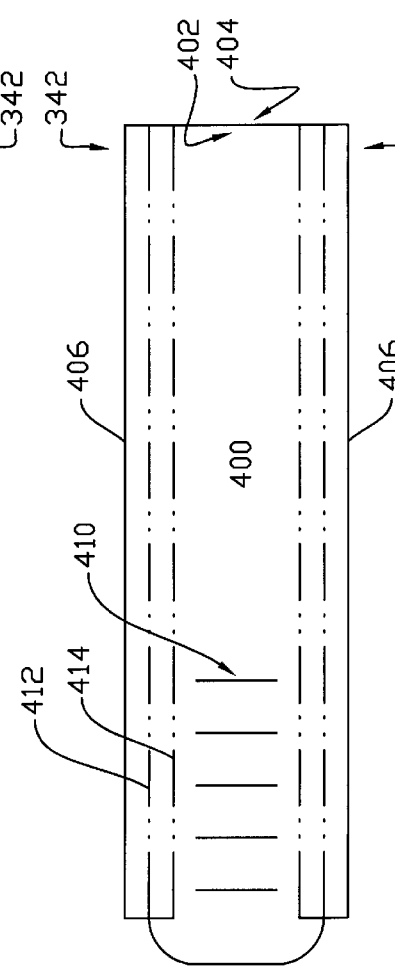

FIG. 16 is a top plan view of the sensor cover layer.

Figure 17:
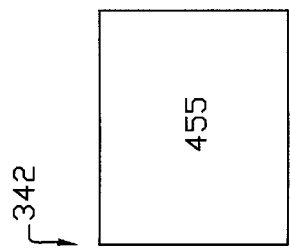

FIG. 17 is a top plan view of the sensor strippable top protective layer.

FIG. 18A is a front (faceplate) view of the monitor/alarm unit. (This view corresponds to the "top plan view" of the unit as it is shown positioned in FIG. 1.)

FIG. 18B is a top edge view of the monitor/alarm unit, showing the opening of the sensor tab receiving portion.

FIG. 18C is a back view of the monitor/alarm unit.

FIG. 18D is a bottom edge view of the monitor/alarm unit.

FIG. 19A is a close-up (magnified scale) back view of the contact spring clip/plate of the monitor/alarm unit.

FIG. 19B is a close-up (magnified scale) top edge view of the contact spring clip/plate of the monitor/alarm unit.

Figure 1:
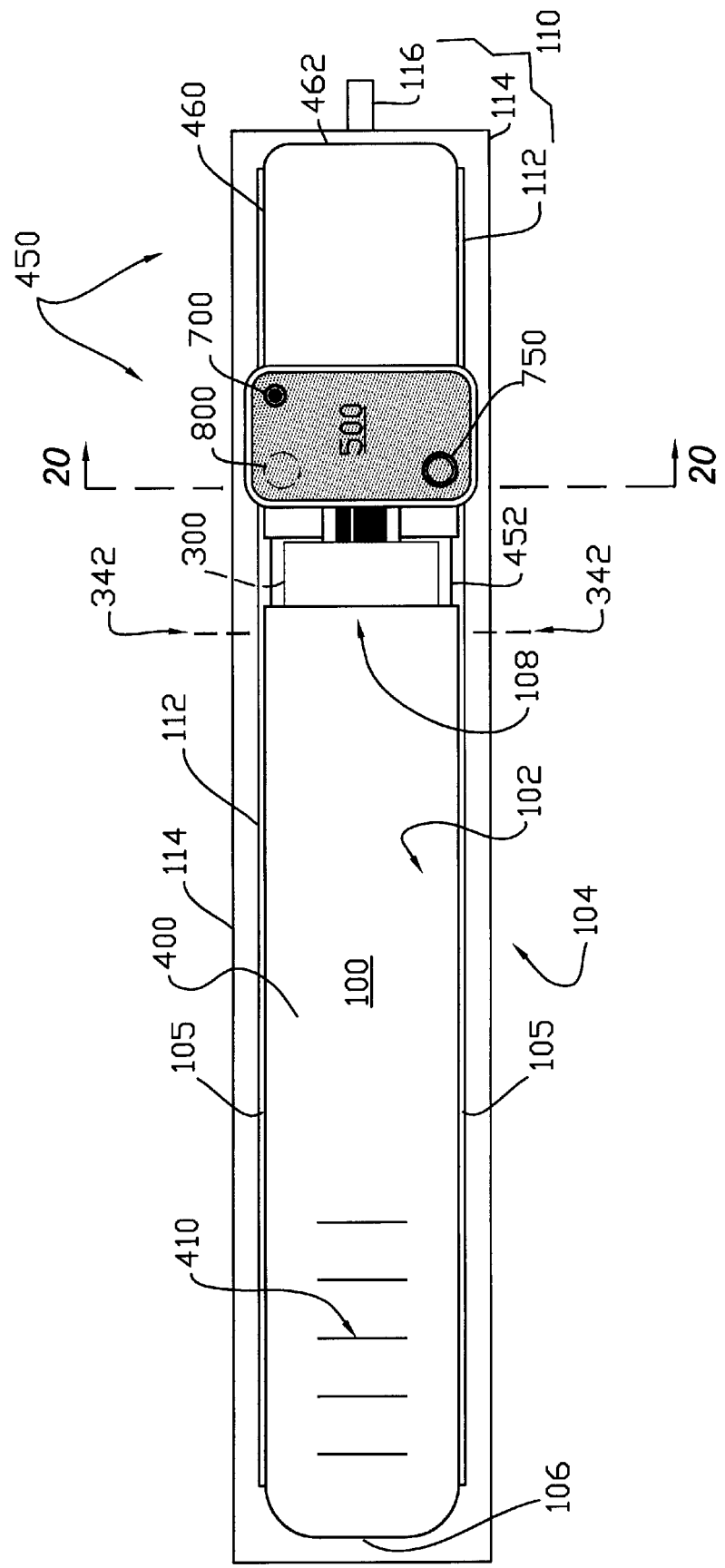
Figure 20:
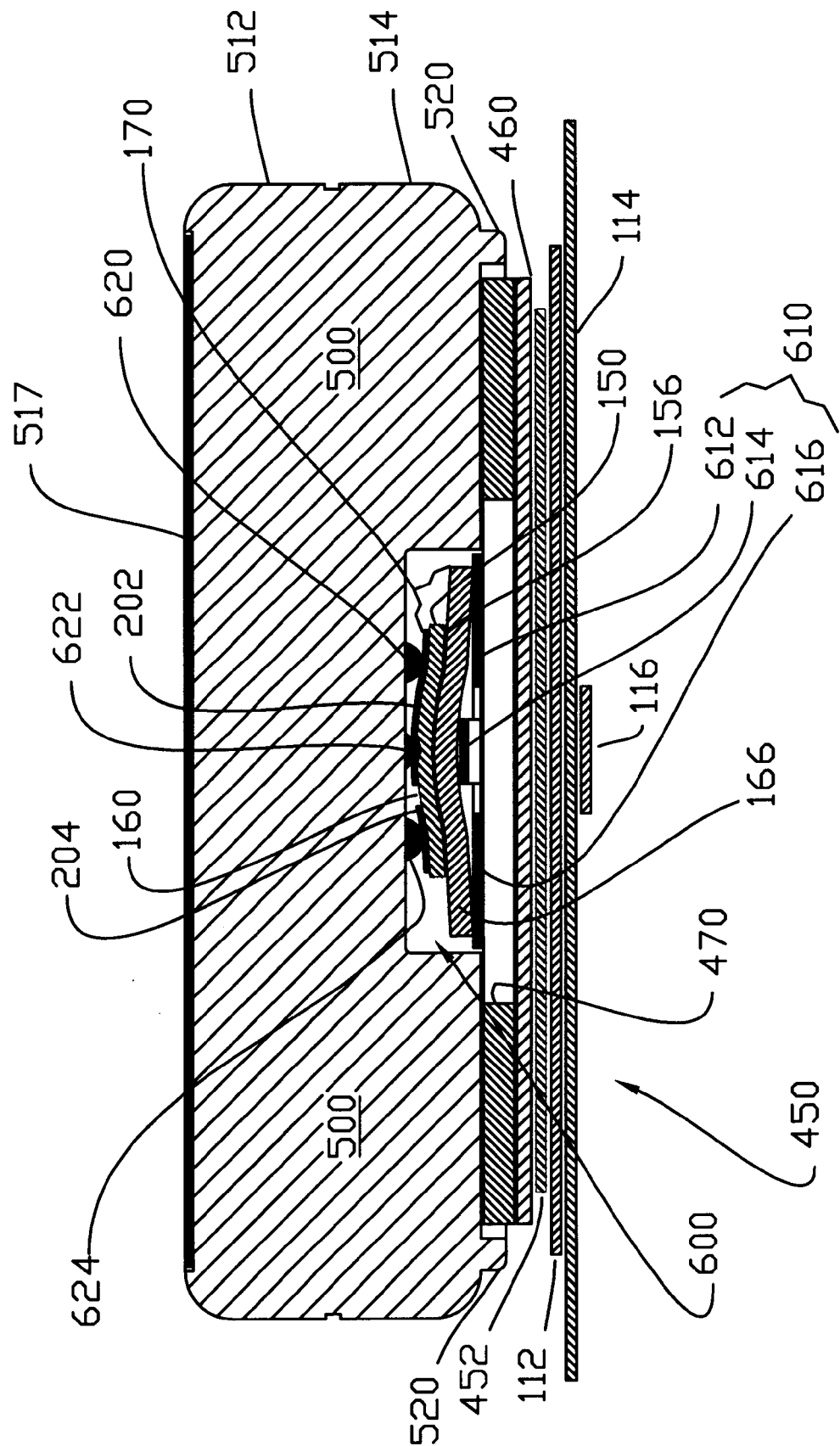

FIG. 20 is a close-up cross-sectional view in elevation taken along line 20—20 in FIG. 1 (but magnified in scale), showing an embodiment of the releasable electronic coupling and retention portion of the sensor, attached to the monitor/alarm unit. This view also shows the flexible, elastic tab-like male connector portion of the sensor, with the conductive members on its upper surface, attached to the monitor/alarm unit. The tab-like sensor portion is shown as deformed between the monitor unit contact-pins, and the prongs of the spring clip/plate.

Figure 21B:
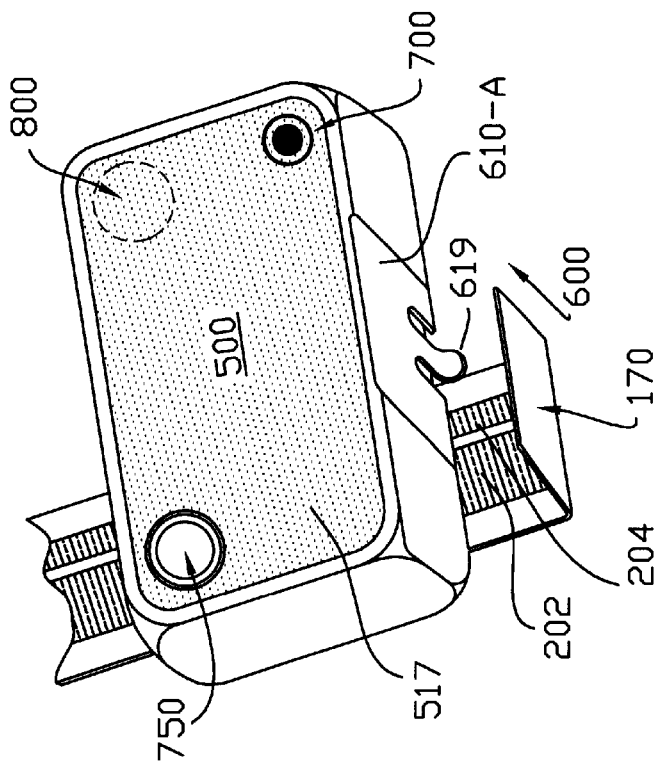
Figure 21A:
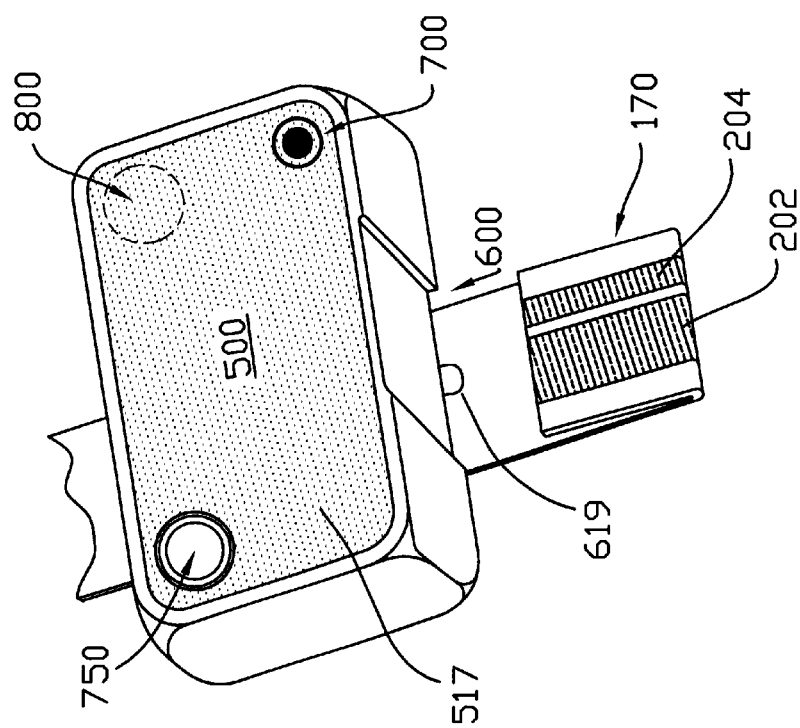

FIG. 21A is a close-up perspective illustration of an alternate embodiment re-usable electronic monitor unit and a segment of the tab-like connector portion of an alternate embodiment disposable sensor, shown entering the receiving portion of the monitor unit.

FIG. 21B is a close-up perspective illustration of another alternative embodiment of the monitor unit and the connector tab portion of a corresponding sensor embodiment, shown entering the monitor unit's receiving portion parallel to an edge of the monitor unit, instead of parallel to the back of the unit as in FIG. 21A.

Figure 22A:
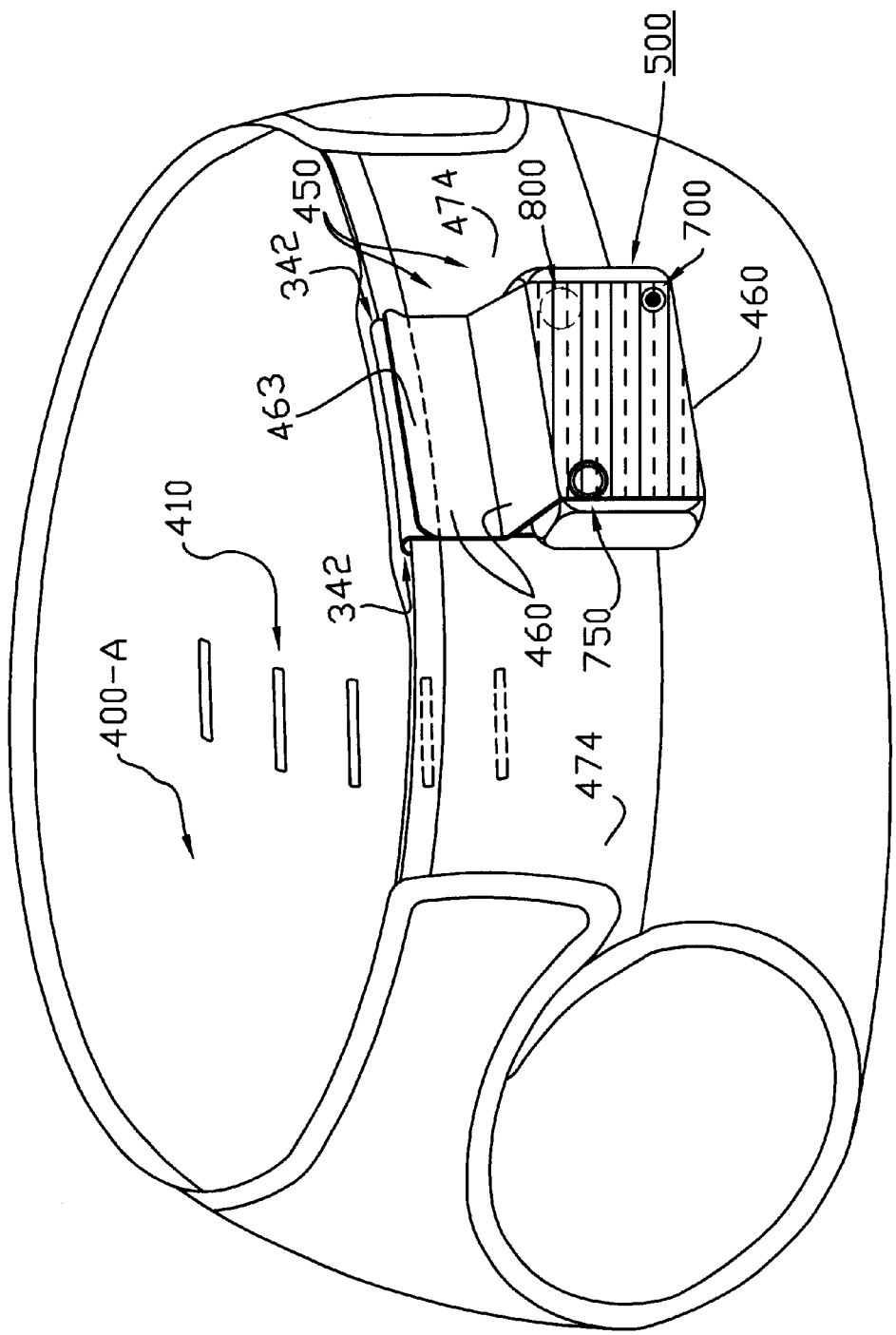

FIG. 22A is a perspective illustration of an embodiment of the system with the sensor incorporated directly into a disposable diaper. The monitor-retaining flap portion of the sensor is disposed on the front of the diaper, much like in the add-on embodiment illustrated in FIG. 2A and FIG. 2B. In FIG. 22A, however, the inner diaper surface is modified to replace the cover layer of the add-on embodiment, and the other layers of the in-diaper portion of the sensor are integrated under this surface. The tab connector portion and monitor-retaining flap portion of the sensor protrude from between the inner and outer diaper covers, over or near the diaper's top front edge.

Figure 22B:
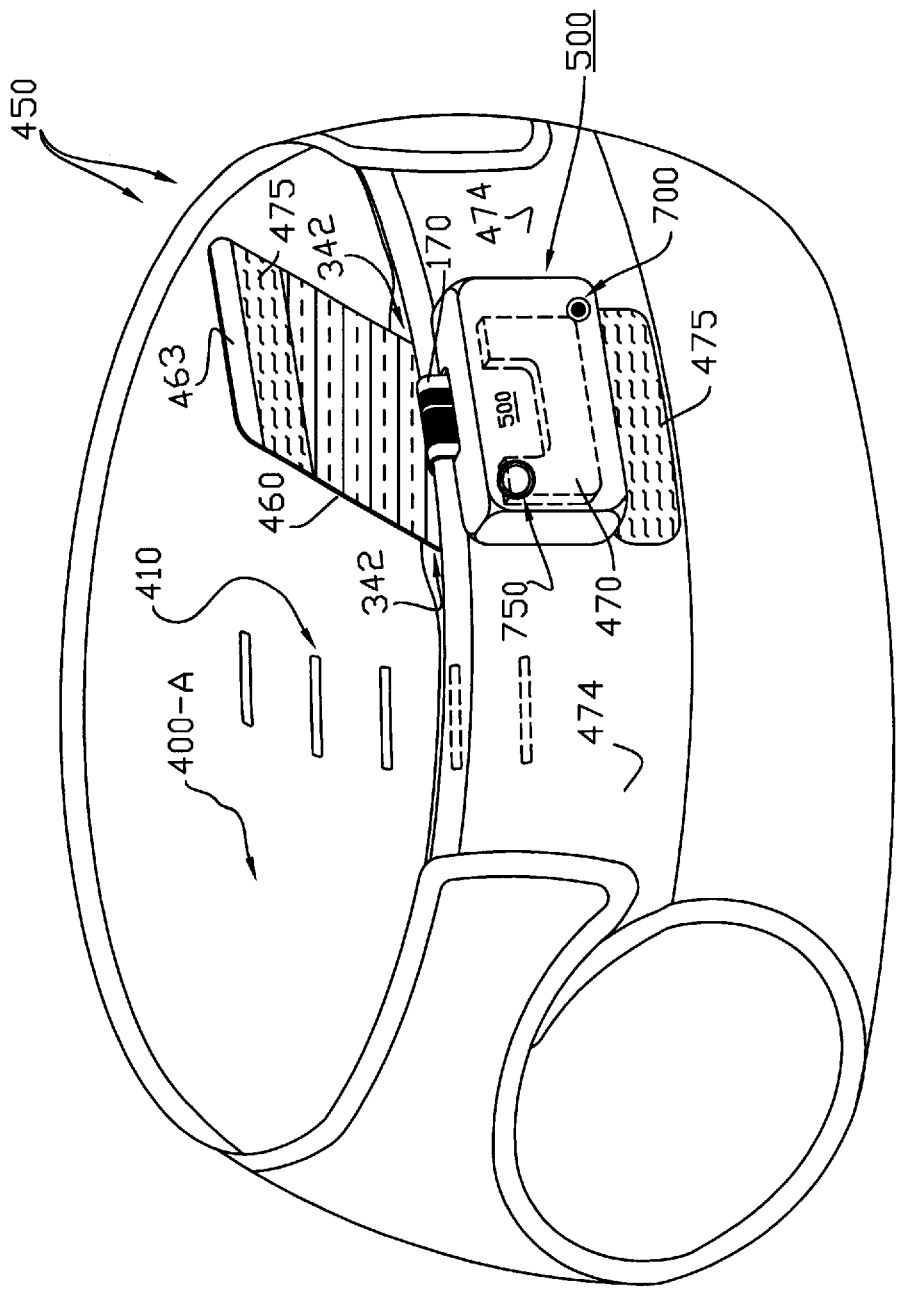

FIG. 22B is a perspective illustration of an alternate embodiment of the monitoring system with the sensor incorporated directly into a disposable diaper, where the sensor's monitor-retaining flap does not first pass under the back of the monitor unit before wrapping over its front (as in FIG. 22A), but instead wraps directly downward over the monitor, to be adhered or otherwise attached to the front of the diaper/sensor below the monitor.

Figure 22C:
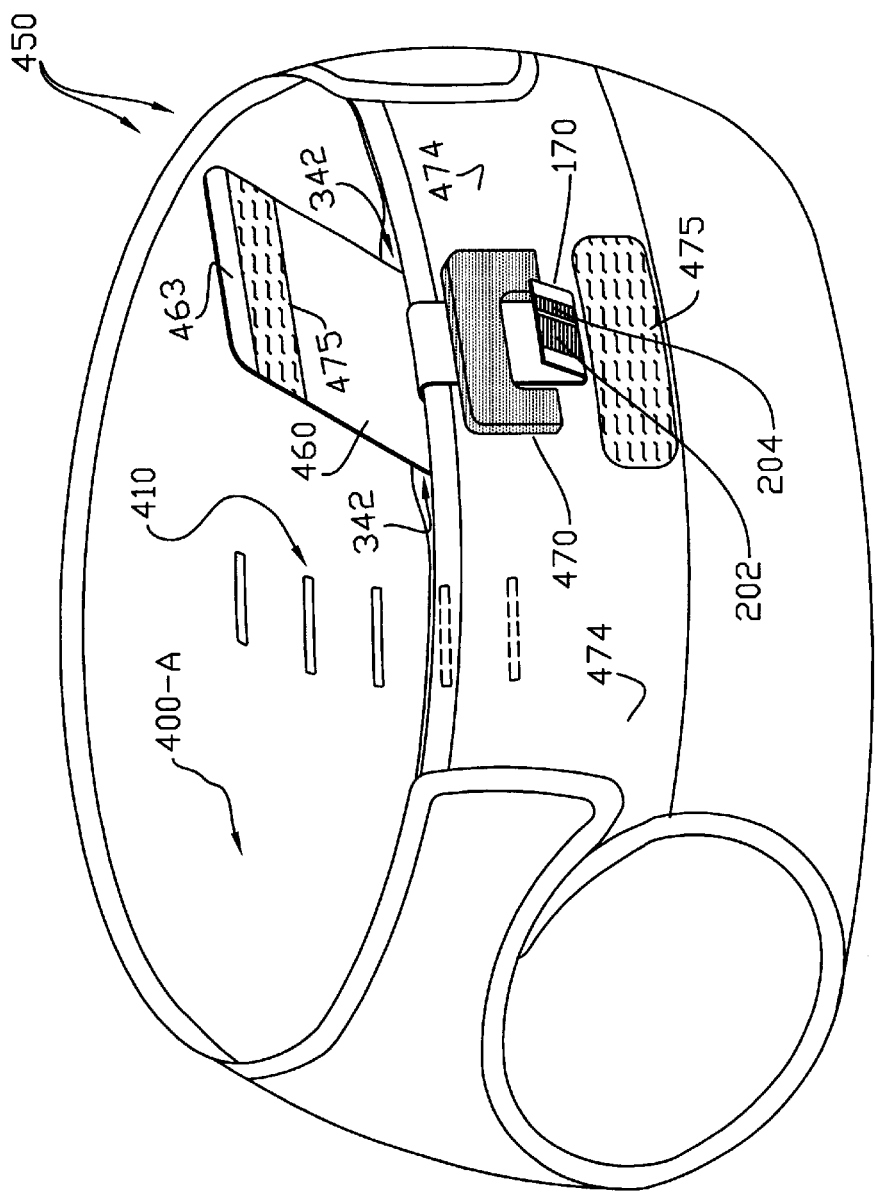

FIG. 22C is a perspective illustration of an alternate embodiment of the sensor, also incorporated directly into a disposable diaper similar to that of FIG. 22B, but where the tab-like connecting portion of the sensor is designed to enter the monitor unit from the opposite (bottom) end. For use with this embodiment, the monitor unit's receiving portion is located on the bottom edge, rather than as in FIG. 22B.

Figure 22D:
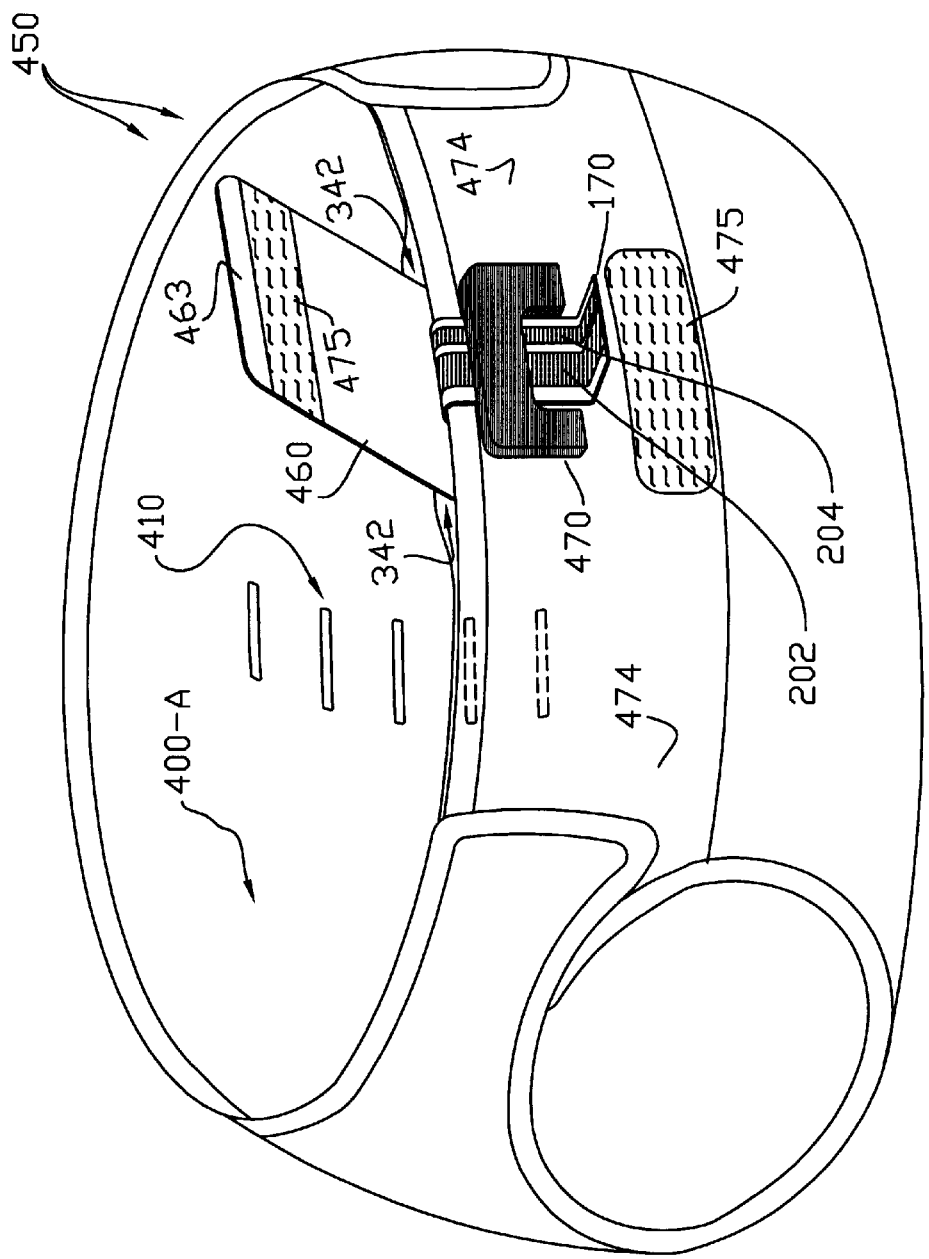

FIG. 22D is a perspective illustration of another alternate embodiment of the sensor, also incorporated directly into a disposable diaper similar to that of FIG. 22C, but where the tab-like connecting portion is designed to enter the monitor unit's receiving portion parallel to an edge of the monitor unit (as shown in FIG. 21 B) instead of parallel to the bottom of the unit (as shown in FIG. 21 A).

Figure 22E:
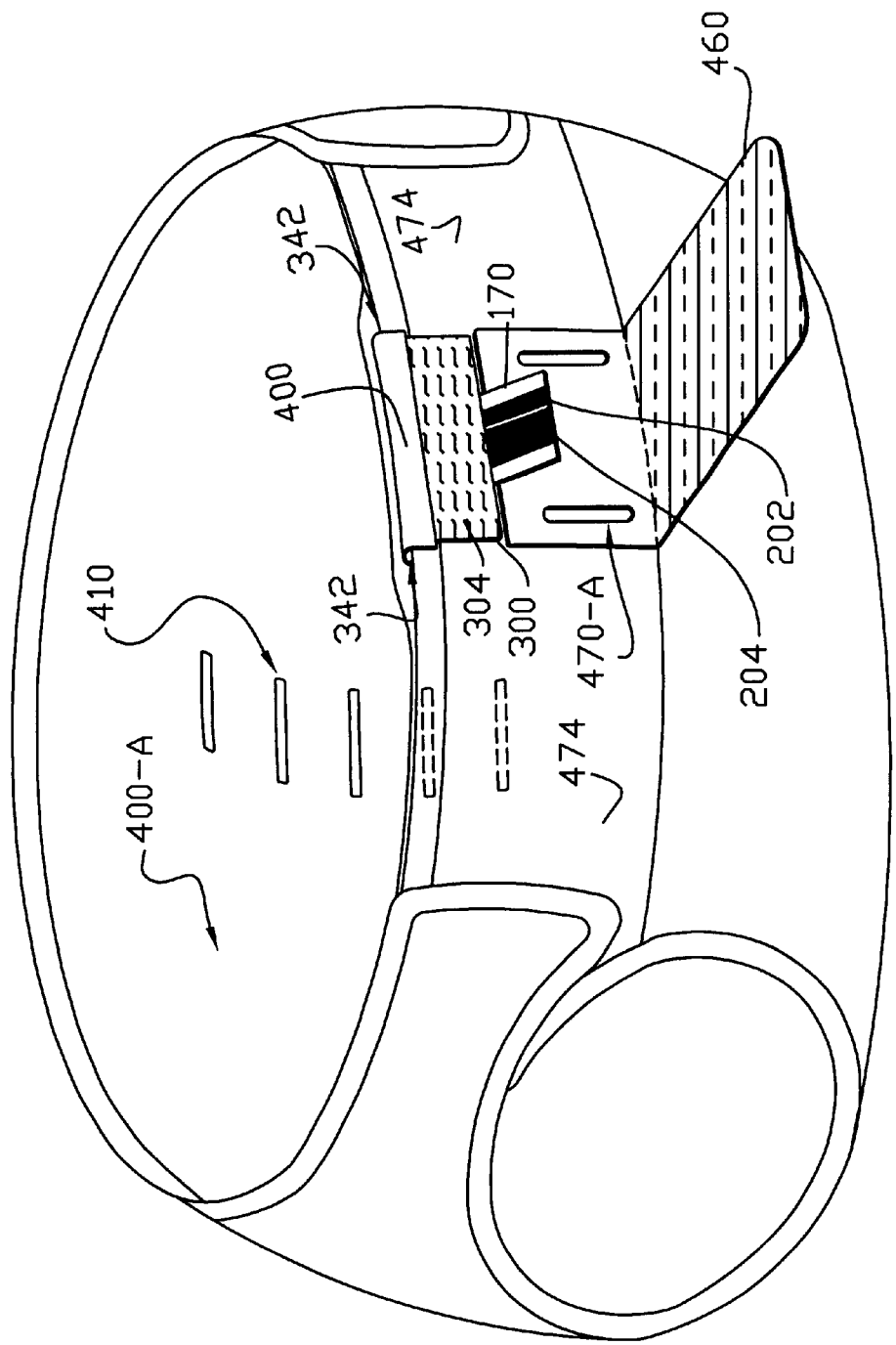

FIG. 22E is a perspective illustration of a preferred embodiment of the sensor as directly incorporated into a disposable diaper, similar to that of FIG. 22A, but where the flap portion of the sensor is disposed on the front of the diaper completely separate from the sensor portion inside the diaper. Also, instead of employing the locating block as shown entrapped under the monitor in FIG. 22B, slot-like openings in the flap portion are provided to receive mating ridges on the back surface of the monitor unit for locating purposes. The tab-like connector portion protrudes from the in-diaper portion at or near the top edge of the diaper.

Figure 23:
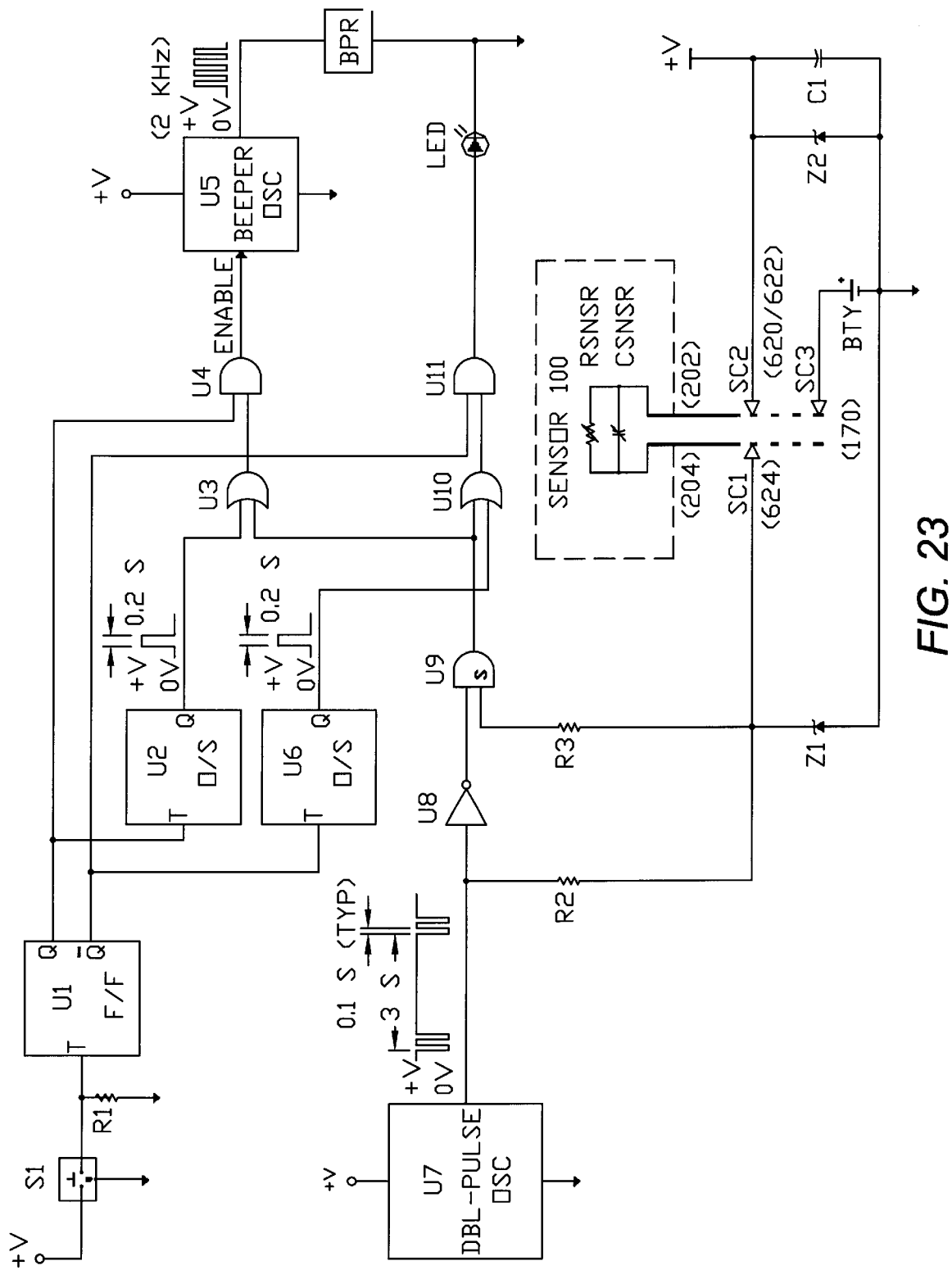

FIG. 23 is a schematic block diagram of a discrete logic circuit employed in the monitor/alarm unit.

Figure 24A:
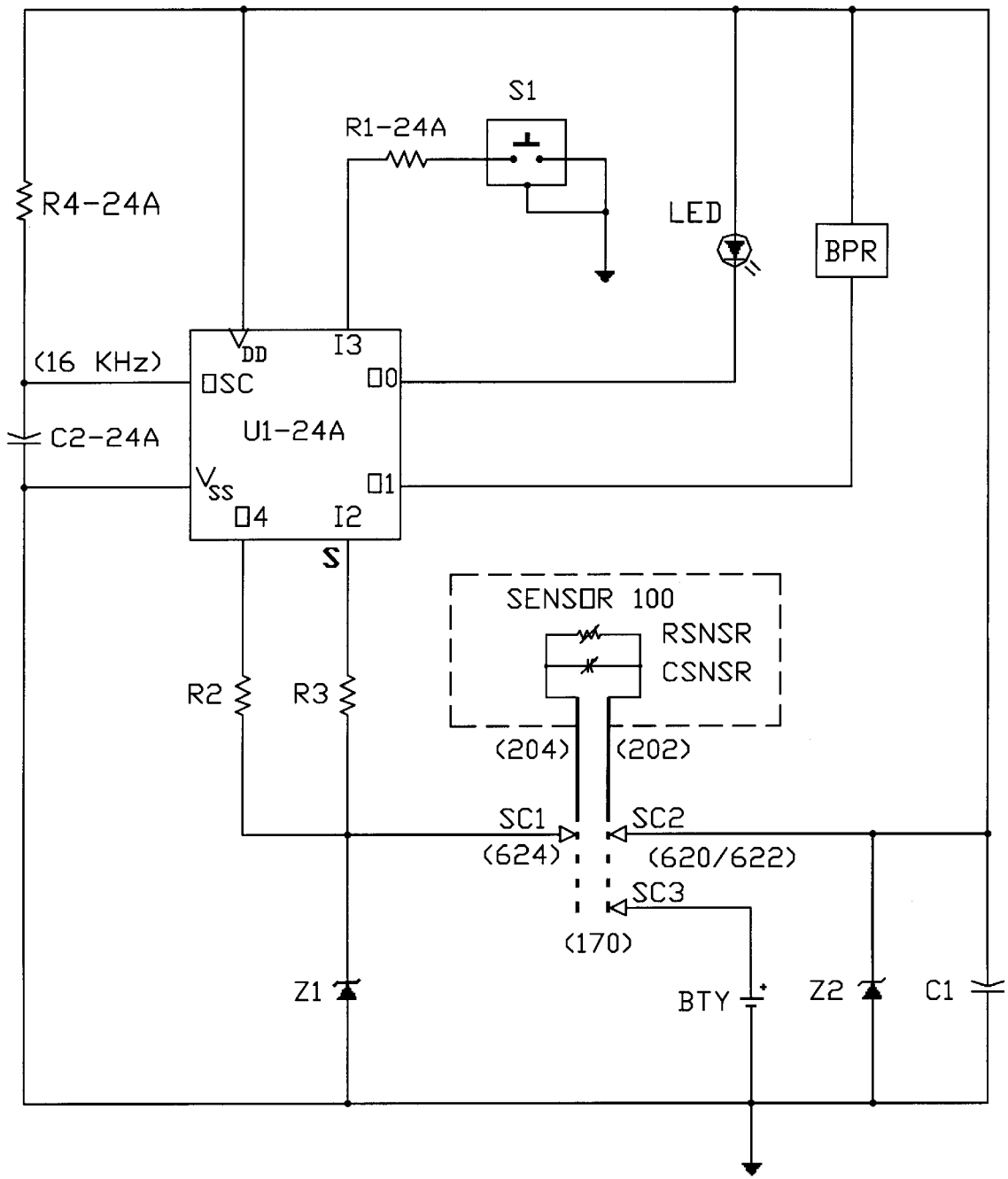

FIG. 24A is a schematic block diagram of a microcontroller-based circuit embodiment alternatively employed in the monitor/alarm unit.

Figure 24B:
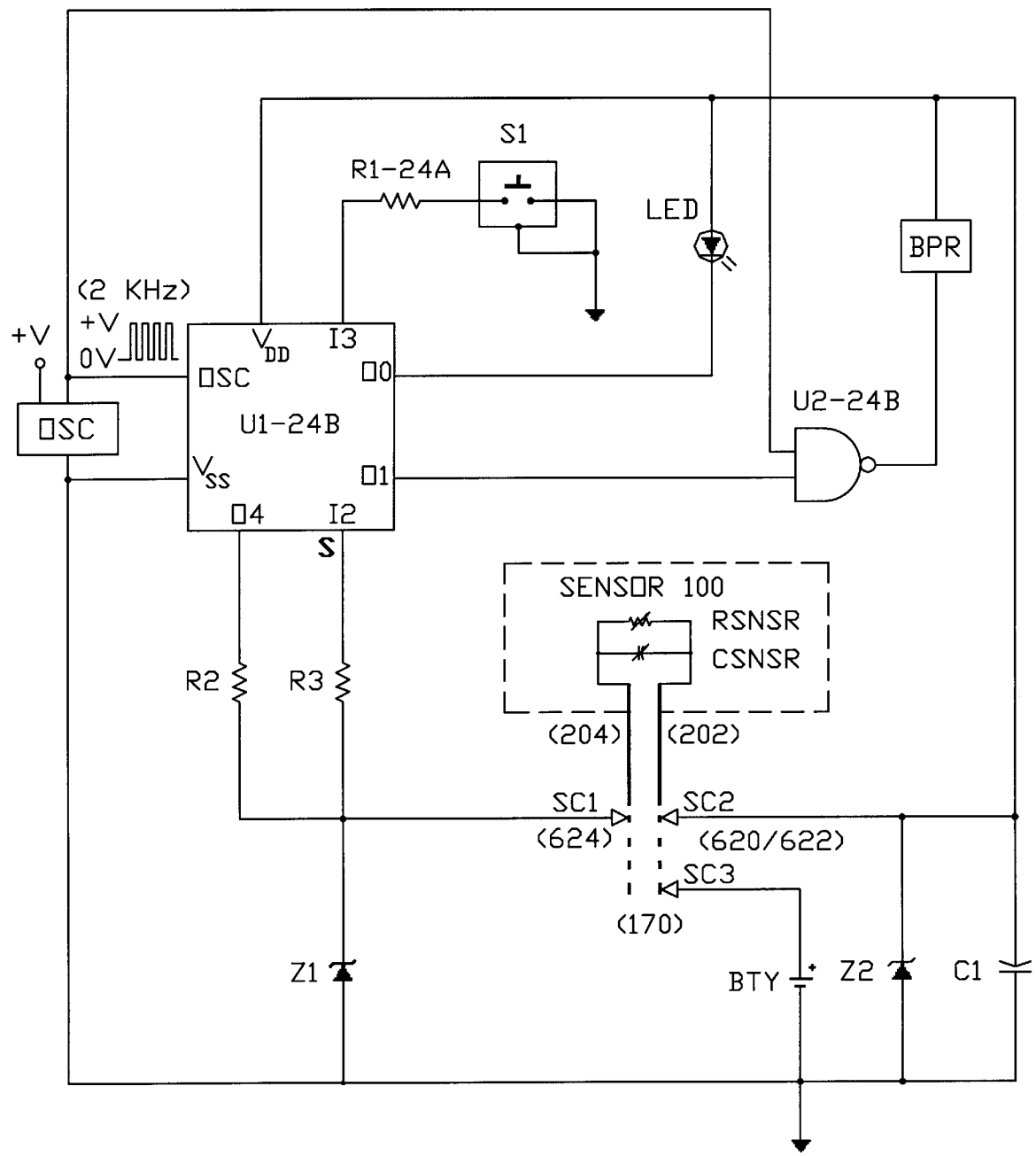

FIG. 24B is a schematic block diagram of a microcontroller-based circuit embodiment alternatively employed in the monitor/alarm unit.

Figure 24C:
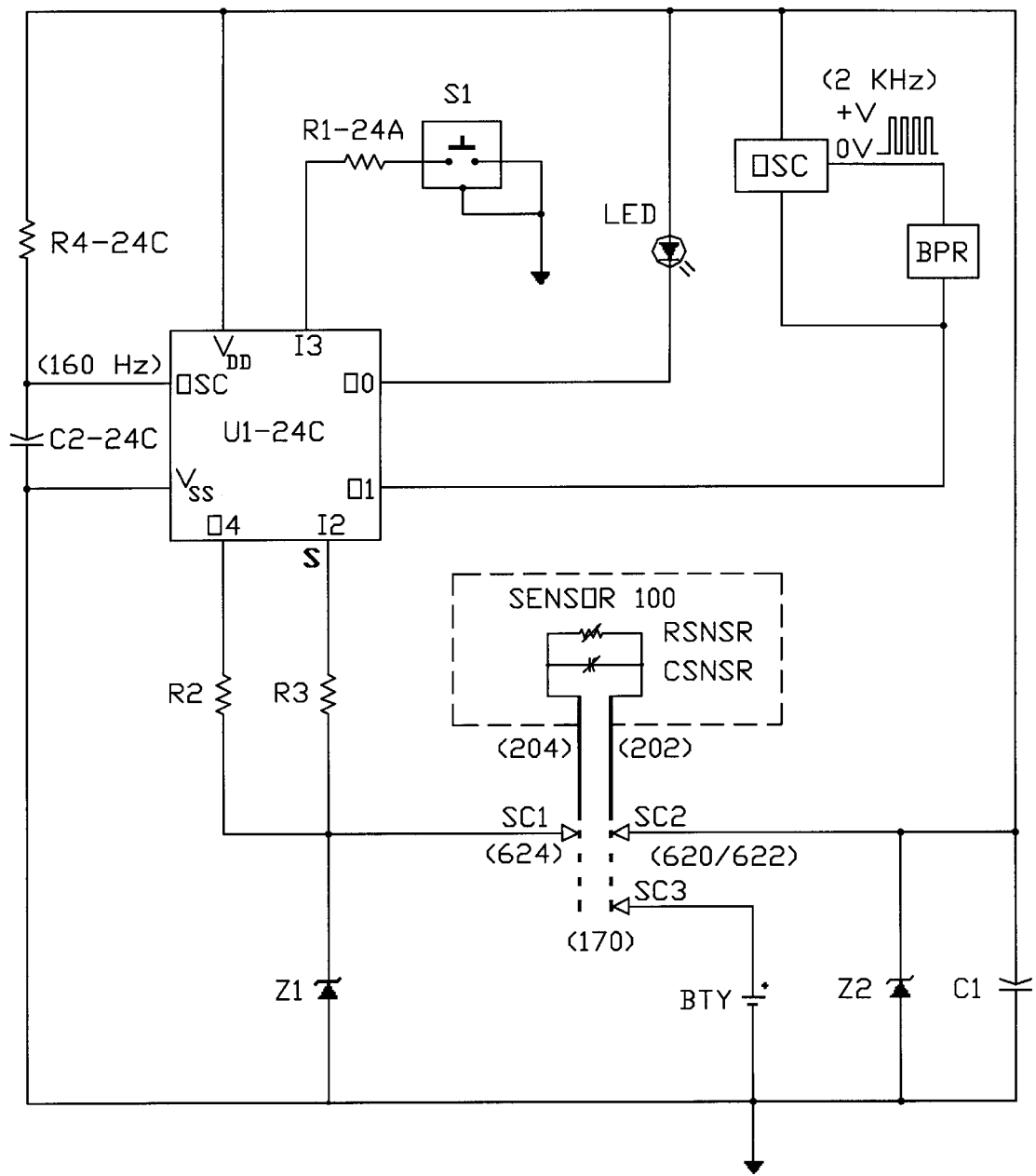

FIG. 24C is a schematic block diagram of a microcontroller-based circuit embodiment alternatively employed in the monitor/alarm unit.

Figure 24D:
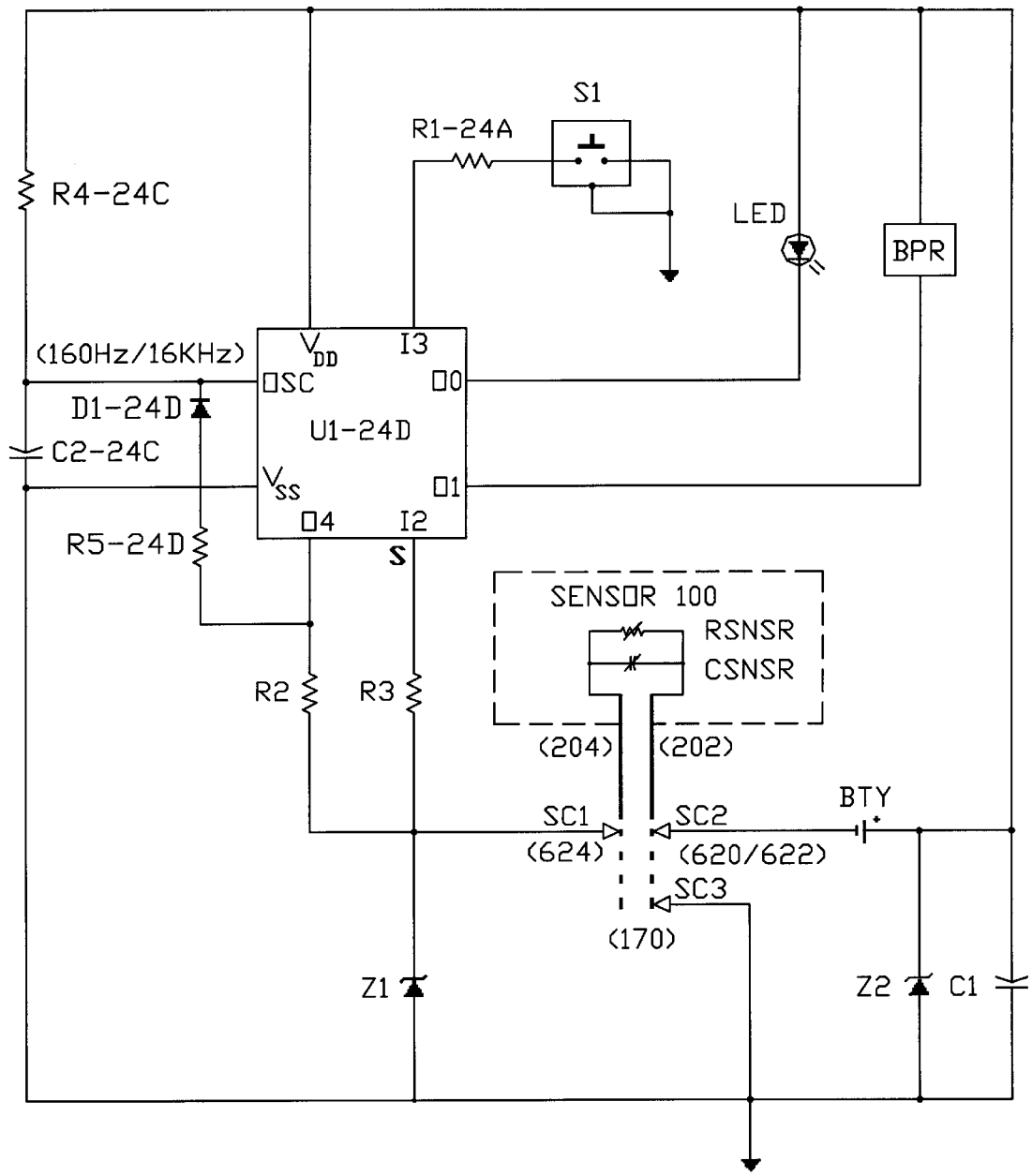

FIG. 24D is a schematic block diagram of a microcontroller-based circuit embodiment alternatively employed in the monitor/alarm unit.

Figure 25:
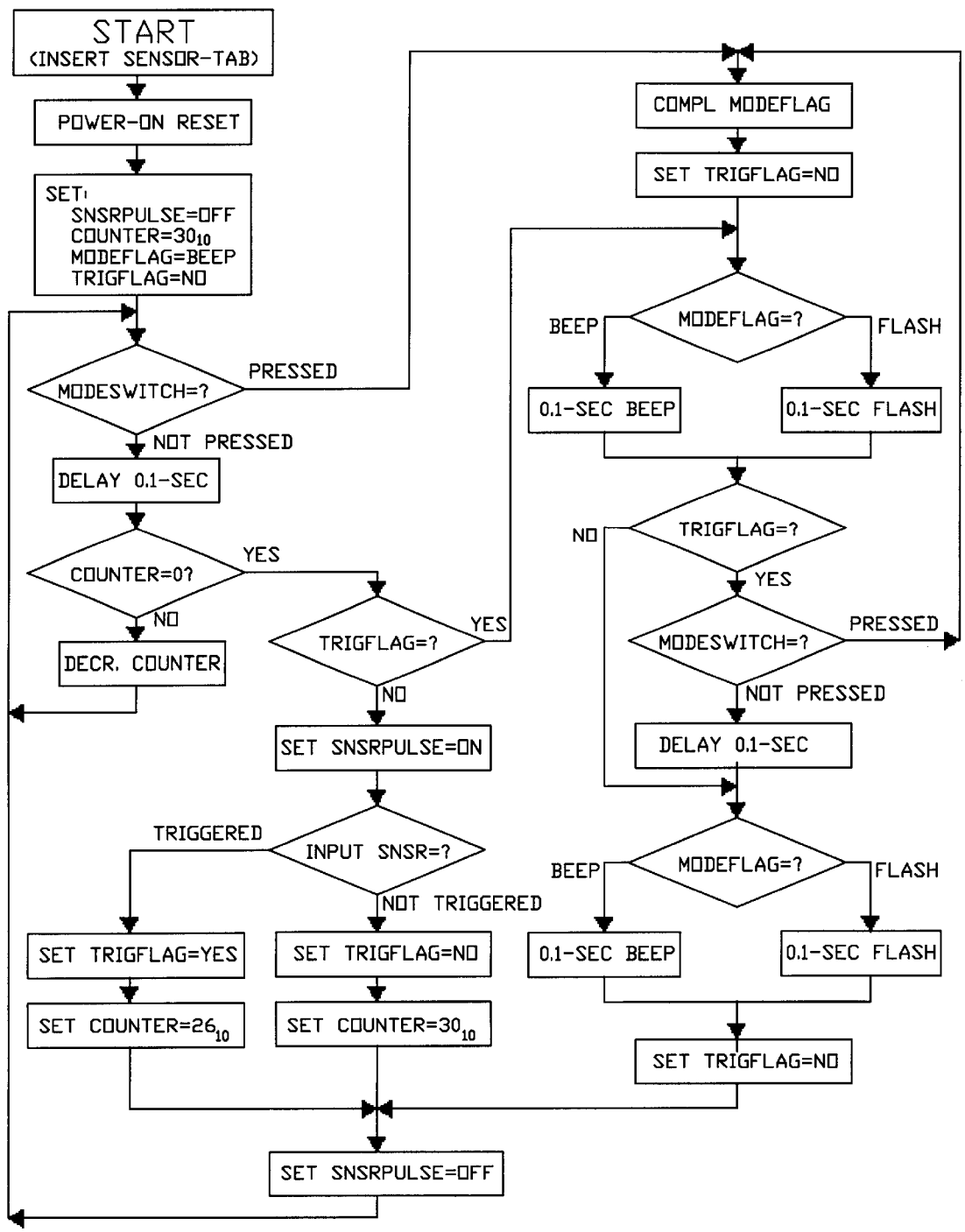

FIG. 25 is a flowchart of the firmware employed in conjunction with a microcontroller-based embodiment of the monitor/alarm unit (as in FIG. 24A).

Figure 26B:
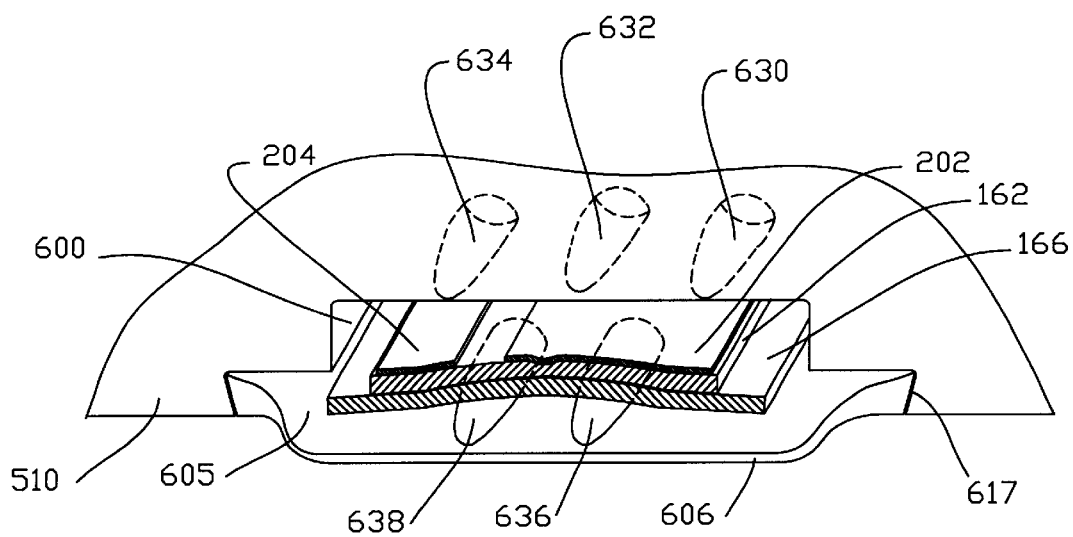
Figure 26A:
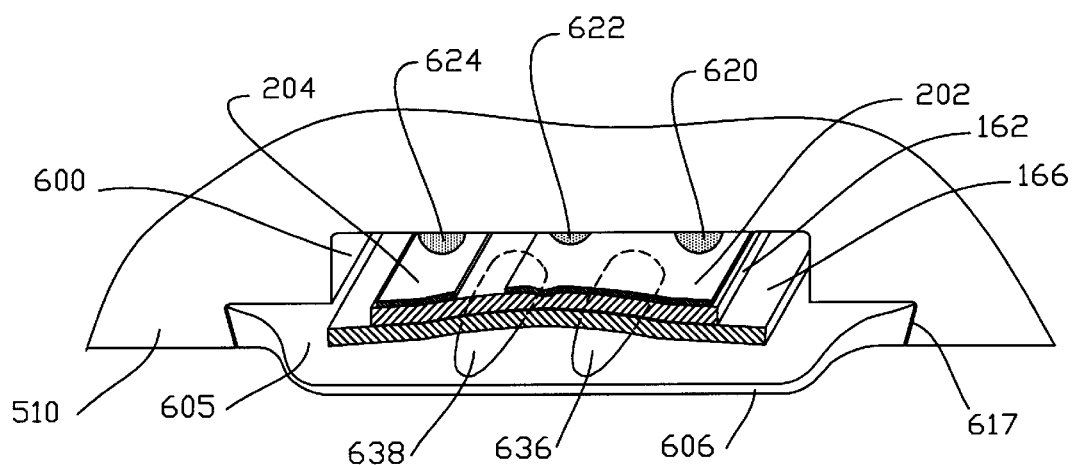

FIG. 26A depicts a close-up view of an alternate version of the connector embodiment shown in FIG. 20, where a short (sectioned) piece of the flexible, tab-like connector portion of the sensor is shown deformed between the monitor unit contact-pins (on one side) and fixed ramping projections (on the opposite side), instead of by the spring clip/plate used in FIG. 20.

FIG. 26B depicts a perspective view of another alternate embodiment of the flexible-tab connector means used in the monitor unit and the sensor; where the short (sectioned) flexible, tab-like connector portion of the sensor is shown deformed from both sides between alternating fixed ramping projections of the receiving connector portion, and where any number of projections can be employed, and where any of them can be conductive.

Figure 27:
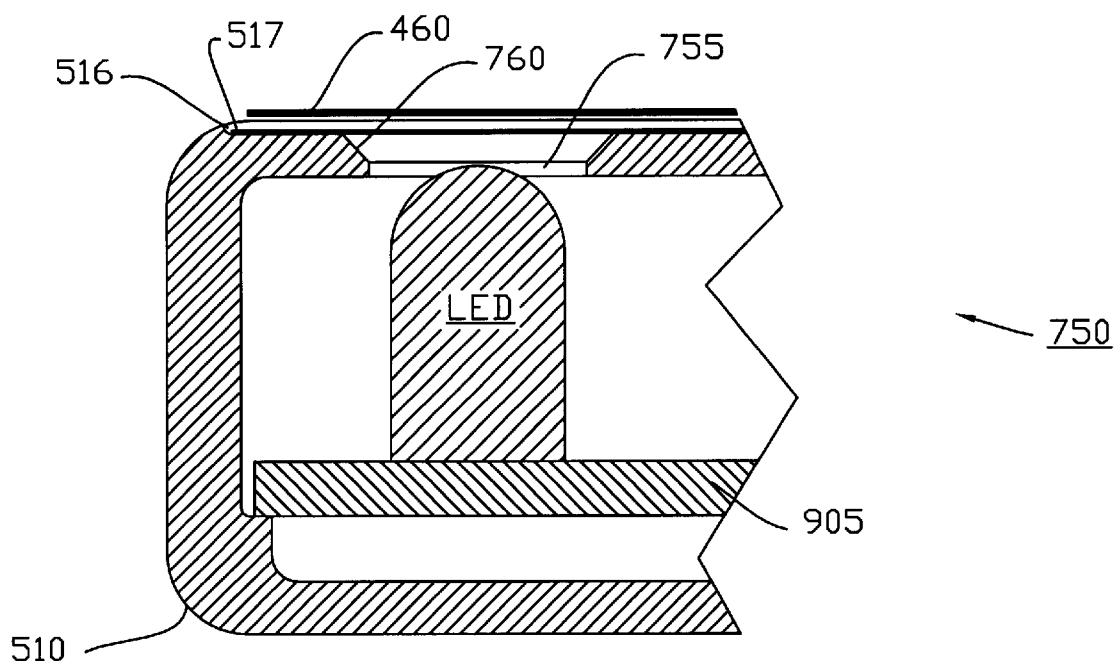

FIG. 27 is a close-up cross-section view of the high viewing-angle visible display means of the monitor unit.

Figure 28:
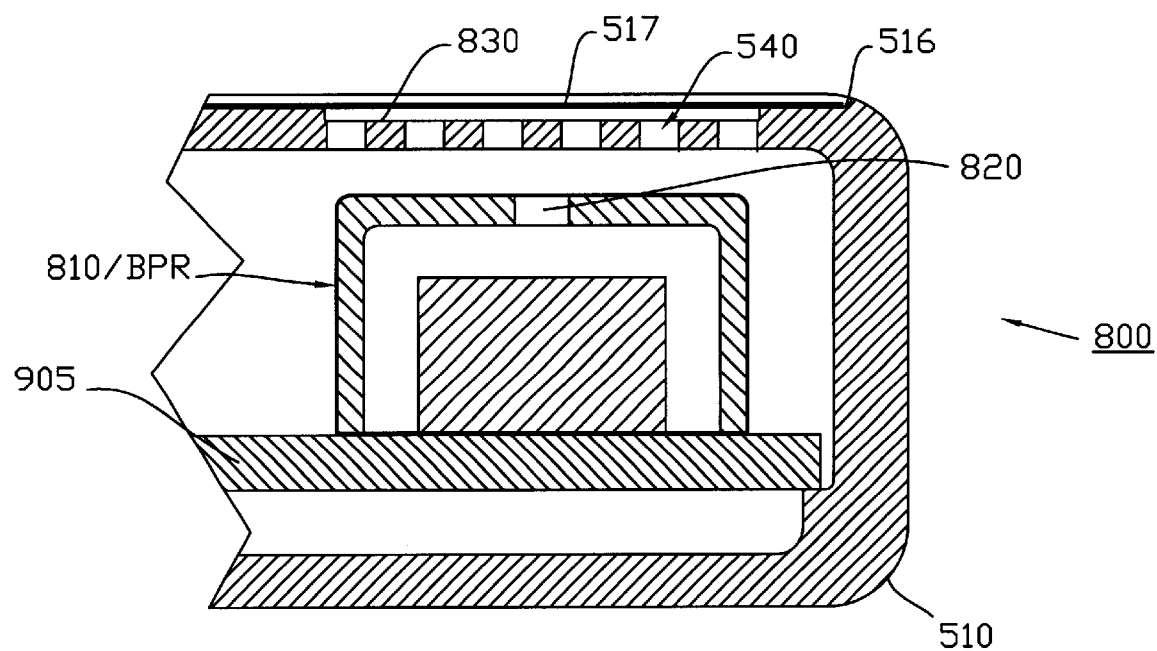

FIG. 28 is a close-up cross-section view of the sealed audible alarm means of the monitor unit.

Figure 29B:
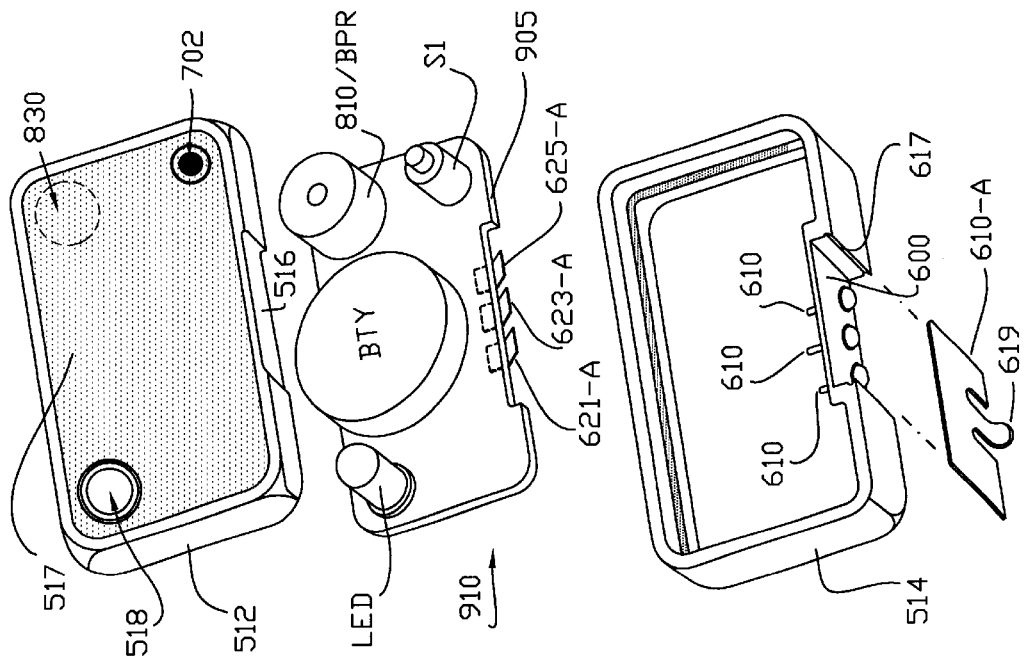
Figure 29A:
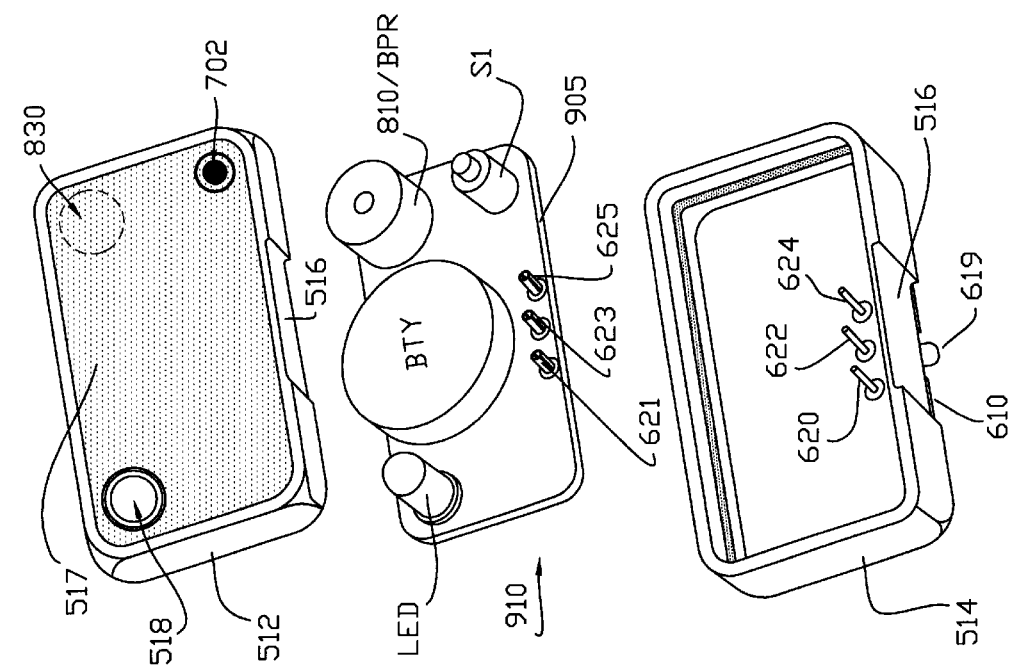

FIG. 29A is an "exploded-view" perspective illustration of a manufacturing assembly method employed with an embodiment of the monitor/alarm unit, as is shown in FIG. 21A.

FIG. 29B is an "exploded-view" perspective illustration of an alternate manufacturing assembly method employed with another embodiment of the monitor/alarm unit, as is shown in FIG. 21B.

Figure 30B:
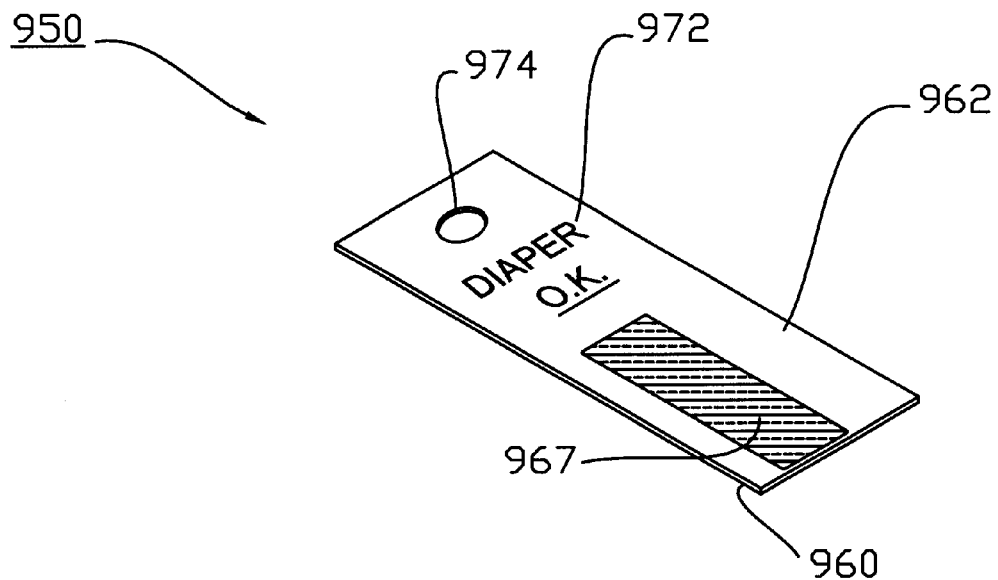
Figure 30A:
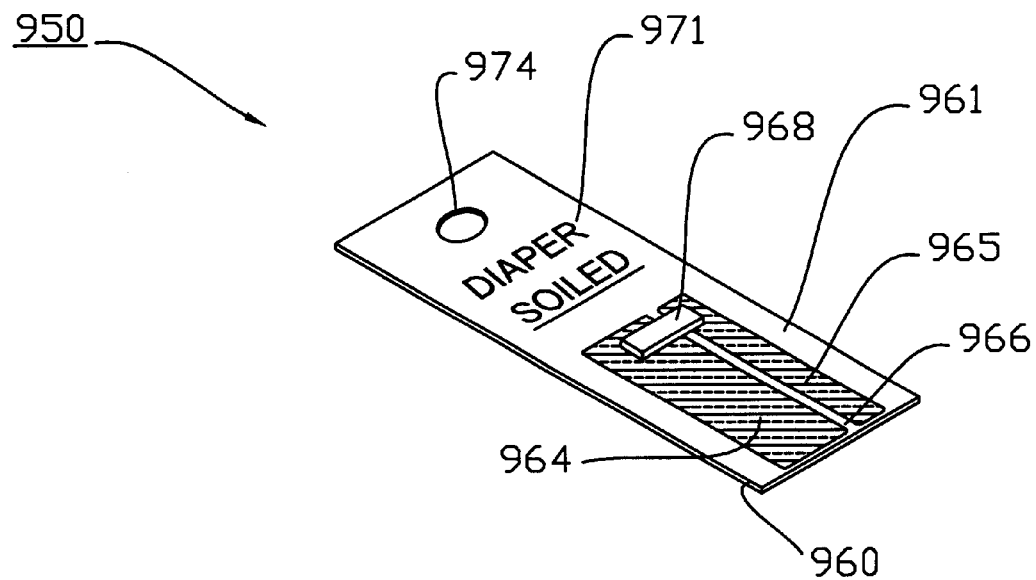

FIG. 30A is a perspective illustration of one side of a sensor-simulating test strip device for use with the monitor/alarm unit.

FIG. 30B is a perspective illustration of the opposite side (relative to FIG. 30A) of a sensor-simulating test strip device for use with the monitor/alarm unit.

REFERENCE NUMBERS IN THE DRAWING FIGURES

No. Description
100 Disposable sensor for elimination-absorber monitoring.
102 Top of sensor 100.
104 Bottom of sensor 100.
105 Side edges of sensor 100.
106 Distal end of sensor 100.
108 Proximal end of sensor 100.
110 Protective layer (covering bottom prior to installation) of sensor 100.
112 Strippable portion of protective layer 110.
114 Wrapping portion of 110.
116 Releasable adhesive fastening tape for wrapping portion 114.
150 Lower impermeable layer of sensor 100.
152 Center core of layer 150.
154 Upper adhesive of layer 150.
156 Lower adhesive of layer 150.
160 Channel between elements 202 and 204 of layer 200.
162 Optionally narrowed front portion of layer 150.
164 Front (proximal) end of layer 150.
166 Tab stiffener of assembly 170 of sensor 100.
170 Male connector tab assembly portion of sensor 100.
200 Electrically conductive elements layer of sensor 100.
202 First electrically conductive member of layer 200.
204 Second electrically conductive member of layer 200.
206 Outer edges of elements 202 and 204.
208 Inner edges of elements 202 and 204.
250 Lower porous/absorbent layer of sensor 100.
252 Elongated feces-detection openings in layer 250.
254 Distal end of absorbent layer 250.
256 Outer edge of absorbent layer 250.
300 Upper impermeable layer of sensor 100.
302 Center core of impermeable layer 300.
304 Upper adhesive of layer 300.
306 Lower adhesive of layer 300.
308 Outer edges of layer 300.
309 Portion of lower adhesive 306 alternatively fixing layer 400.
310 First (outer or "spillway") series of openings in layer 300.
312 Front-most edges of openings 310.
314 Rear-most edges of openings 310.
316 Outermost edges of openings 310.
318 Innermost edges of openings 310.
320 Second (inner or "flow-splitting") series of openings in layer 300.
322 Outermost edges of openings 320.
324 Innermost edges of openings 320.
330 Elongated feces-detection openings in layer 300.
332 Gap through layer 300, separating absorbent layer 250 from 350.
340 Proximal end of layer 300.
342 Fold line of sensor (where it folds over top front edge of diaper).

344 Optional opening through layer(s) 300/460 for passage of tab assembly 170.
350 Upper porous/absorbent layer of sensor 100.
352 Elongated feces-detection openings in layer 350.
354 Outer edges of layer 350.
400 Cover layer of sensor 100 (contacts the skin of a diaper wearer).
400-A Inner (skin-contacting) modified diaper lining of incorporated sensor 100.
402 Top surface of layer 400.
404 Bottom surface of layer 400.
406 Outer side edges of layer 400.
410 Elongated feces-detection openings in layer 400.
412 Line about which layer 400 is folded.
414 Line to which layer 400 is folded.
416 Side edge portions of cover 400 that are affixed to layer 300.
418 Floating soft edge of sensor 100 (layer 350 covered by layer 400).
450 Releasable electronic coupling and retention portion of sensor 100.
452 Connecting and attaching layer of portion 450.
453 Center core of connecting/attaching layer 452.
454 Top adhesive means of layer 452.
455 Strippable top protective layer of sensor 100.
456 Bottom adhesive means of layer 452.
460 Monitor/alarm retaining flap of sensor 100.
462 Most proximal end of flap 460.
463 Pull-tab portion near end 462 of flap 460.
470 Monitor/alarm locating block of sensor 100.
470-A Alternative monitor/alarm locating features of sensor 100.
472 Notch in locating block 470.
474 Top front diaper surface where monitor 500 is retained/connected to sensor.
475 Alternative adhesive/adhesion areas for securing flap 460.
500 Monitor/alarm unit.
510 Protective case of monitor/alarm unit 500.
512 Front portion of case 510.
514 Back portion of case 510.
516 Surface feature of case 510, emphasizing location of receiving portion 600.
517 Faceplate overlay on 512.
518 Balloon or other graphic symbol on faceplate 517 highlighting assembly 750.
520 Mating feature on back of 500 to engage locating block 470.
530 Top (edge) of case 510 (relative to position on the front of a diaper).
532 Bottom (edge) of case 510 (relative to position on the front of a diaper).
534 Left side of case 510 (as viewed from front or faceplate side).
536 Right side of case 510.
540 Acoustically transmissive opening(s) through case 510.
600 Sensor-connector receiving portion in the lower case half 514 of monitor 500.
605 Pressure-plate of alternative connector means in monitor unit 500.
606 Lead-in lip of pressure-plate 605 or recess 600.
610 Spring clip/plate of monitor unit 500.
610-A Alternative embodiment of 610.
612 First (e.g., plate-like outboard) prong of 610.
614 Second (e.g., center active spring clip) prong of 610.
616 Third (e.g., plate-like outboard) prong of 610.
617 Dovetail slots or other retention means.
618 Attachment means of clip/plate 610 to case 510.
619 Smooth rounded tip of prong 614 of clip/plate 610.
620 First contact pin of monitor unit 500.
621 First contact-pin socket of circuit board assembly 910.
621A Alternative first contact-pin pressure spring of circuit board assembly 910.
622 Second (center) contact pin of monitor unit 500.
623 Second (center) contact-pin socket of circuit board assembly 910.
623-A Alternative second contact-pin pressure spring of circuit board assembly 910.
624 Third contact pin of monitor unit 500.
625 Third contact-pin socket of circuit board assembly 910.
625-A Alternative third contact-pin pressure spring of circuit board assembly 910.
630 First contact pin of an alternate connector embodiment of monitor 500.
632 Second contact pin of an alternate connector embodiment of monitor 500.
634 Third contact pin of an alternate connector embodiment of monitor 500.
636 First opposed ramping protrusion of an alternate connector embodiment.
638 Second opposed ramping protrusion of an alternate connector embodiment.
700 Mode change assembly of monitor unit 500.
702 Dot or other graphic symbol indicating location of mode change assembly 700.
705 Hole through front case portion 512 for flush button of mode-change switch S1.
750 Visible signal transmission assembly of monitor unit 500.
755 Hole in face surface 516 of monitor 500 for visual signal transmission.
760 Chamfered edge of hole 755.
800 Audible signal assembly of monitor unit 500.
810/BPR Electro-acoustic transducer of monitor unit 500 (also referred to as "BPR").
820 Acoustic wave propagation hole in transducer 810.
830 Shallow recess behind overlay faceplate membrane 517 in case 510.
900 Electronic circuitry employed in monitor/alarm 500.5
905 Electronics printed circuit board of monitor unit 500.
910 Electronic circuit board assembly of monitor unit 500.
950 Diaper-simulating test-strip device for use with monitor 500.
960 Tab (substrate) of test strip device.
961 One side of system test strip device.
962 Opposite side (to 961) of system test strip device.
964 First area of conductive coating.
965 Second area of conductive coating.
966 Gap between conductive coating elements 964 and 965.
967 Area of conductive coating on side 962.
968 Chip resistor or other reference-valued device.
971 Indicative marking on side 961.
972 Indicative marking on side 962.
974 Hole or opening through 960.
Note: Other reference designators that appear only in the electronic schematic diagrams of FIG. 23, FIG. 24A, FIG. 24B, FIG. 24C and FIG. 24D, and in the text descriptions referencing those diagrams, are not listed above.

DETAILED DESCRIPTION OF THE INVENTION

The System

Figure 2A:
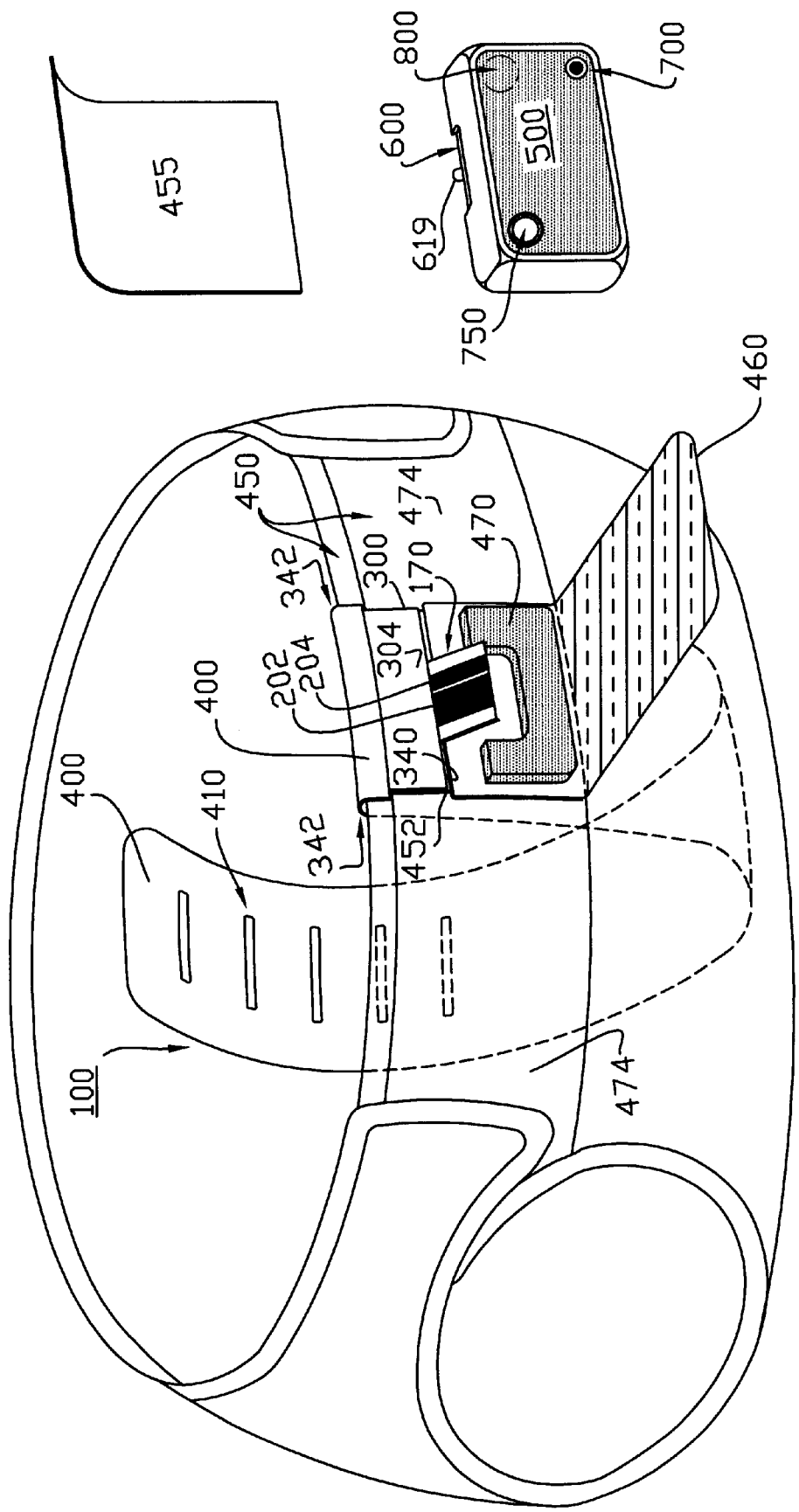
Figure 2B:
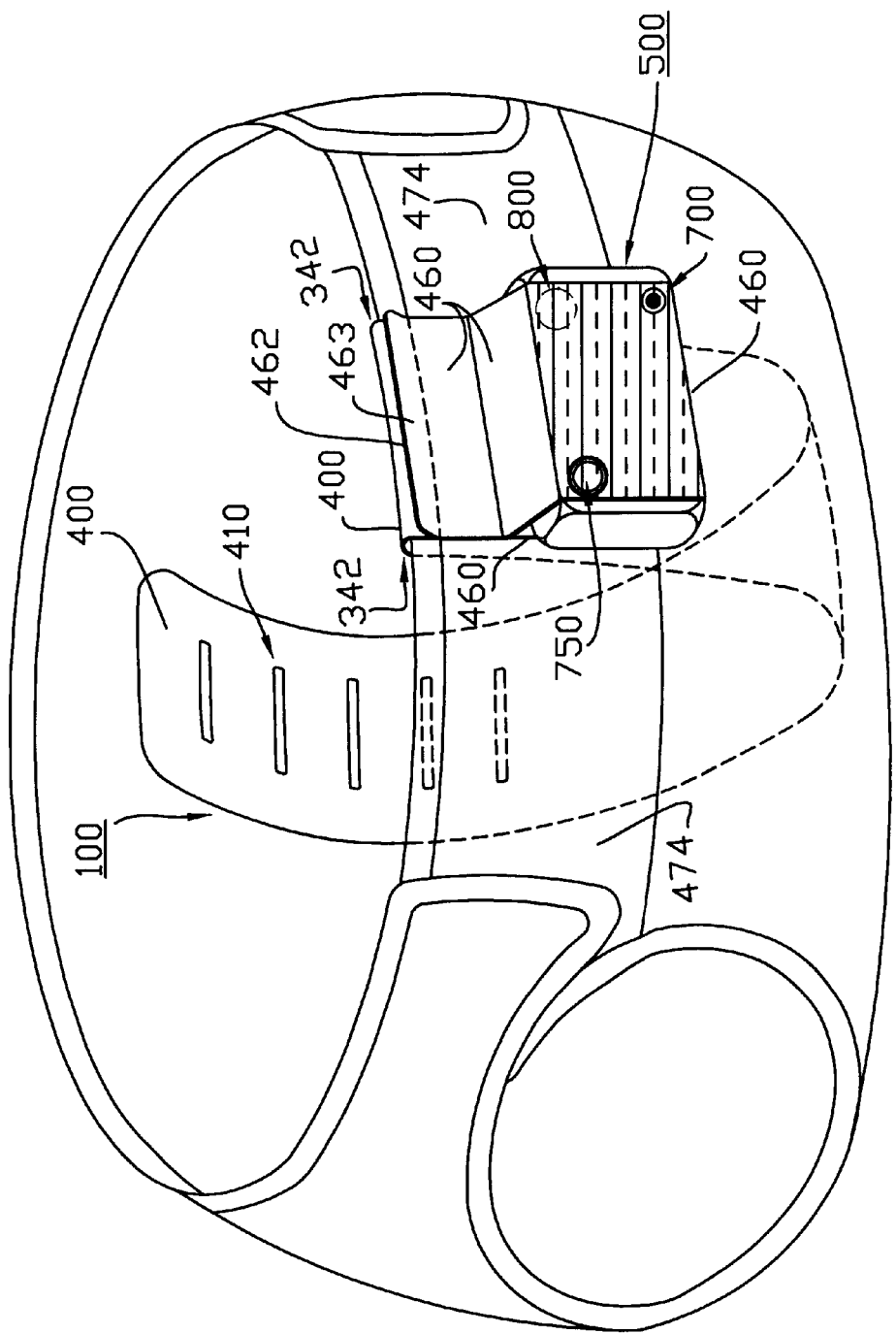

As illustrated in FIG. 1, a preferred embodiment of the elimination-absorber monitoring system includes a releaseably-interconnected, disposable sensor 100 and a reusable monitor/alarm unit 500. The system is suitable for use with various diapers (reusable-cloth and disposable), undergarments, bedding and the like. A preferred use, i.e., with the sensor provided as an add-on product to be applied to disposable diapers (illustrated in FIG. 1, FIG. 2A and FIG. 2B), is the primary basis for the invention description. Modifications necessary to adapt the system or its components for use in other environments are also described below. For example, FIG. 22A depicts the sensor, pre-incorporated as part of a disposable diaper. In such an incorporated embodiment, a removable bottom protective layer 110 of the add-on unit shown in FIG. 1, is not necessary. Also, a top cover layer 400 and a top absorbent layer 350 (underneath layer 400) of the add-on unit can be replaced, respectively, by the diaper inner surface 400-A (shown in FIG. 22A) and an underlying portion of the diaper's absorbent layer(s). As will be described, the novel underlying operative principles and means of sensor 100 can be applied in numerous ways, either to modify the sensor response characteristics, or to achieve other objectives such as manufacturing cost reduction. The sensor can be provided with an adhesive backing, or it can be otherwise affixed in the diaper. A releasable electronic coupling and monitor-retention portion 450 of the sensor can protrude from the diaper and be disposed on a top front diaper surface 474, either as in the add-on unit as shown in FIG. 2A and FIG. 2B, or by utilizing various additions or modifications to a diaper such as are shown in FIG. 22A, FIG. 22B, FIG. 22C, FIG. 22D and FIG. 22E.

The Sensor

Sensor 100 is typically a multi-layer assembly, resembling a pad or strip, that is applied directly to, or incorporated within a diaper or other article with which it is to be used. A preferred add-on embodiment of the sensor, shown in FIG. 1, has a top 102, a bottom 104, two side edges 105, a distal end 106 and a proximal end 108. Shown to the right of a dashed fold line 342 (indicating the line at which the sensor is designed to fold over the top front edge of a diaper as shown in FIG. 2A), is releasable electronic coupling and monitor-retention portion 450. Portion 450 of the sensor includes means for the attachment and retention of monitor/alarm 500, and is shown in the close-up perspective view of FIG. 5A. The preferred disposable add-on embodiment, as introduced above, is further illustrated in FIG. 3, showing the various superposed layers. For clarity, removable bottom protective layer 110 and a similarly strippable top protective cover 455 (shown in FIG. 5A), are omitted. The layers of the embodiment of FIG. 3 are presented in the magnified cross-section views of FIG. 3A, FIG. 3B and FIG. 3C. The relevant locations and orientations of these cross sections are indicated in FIG. 3. This embodiment of sensor 100 is also shown (including all layers) in the vertically-exaggerated side elevation view of FIG. 4. In FIG. 4, the layers include, from bottom to top: removable protective layer 110 (comprised of a releasable adhesive fastening tape 116, a wrapping portion 114, and a strippable portion 112), a lower connecting/attaching layer 452, a monitor/alarm retaining flap layer 460, an optional monitor/alarm locating block 470, a tab stiffener 166, a lower relatively impermeable layer 150, an electrically conductive elements layer 200, a lower porous/absorbent layer 250, an upper relatively impermeable layer 300, second porous/absorbent layer 350, cover layer 400, and strippable top protective layer 455. These layers, including the dimensions thereof, will be described in greater detail below, particularly so with regard to the same preferred embodiment. The layers are shown separately in FIG. 6, FIG. 7, FIG. 8, FIG. 9, FIG. 10, FIG. 11, FIG. 12, FIG. 13, FIG. 14, FIG. 15, FIG. 16 and FIG. 17, respectively.

Just as certain sensor modifications may be required to adjust for different embodiments and use environments, differing size diapers will require that at least some of the dimensions vary (preferably, only the lengths of certain layers), but not necessarily in direct proportion to the differences in diaper size. The detailed description of layers 452, 166, 150, 200, 300, 460, 470 and 455, comprising releasable electronic coupling and retention portion 450 of the sensor, will be addressed later in the specification. This is so that the layers comprising the "inside-the-diaper" portion of the sensor (as shown to the left of fold line 342 in FIG. 1, FIG. 3 and FIG. 4), can be first addressed as a key functional structure.

"Bounding" and the Effects of Adhesives, Coatings and Inter-Layer Attachments

In describing the various layers of sensor 100, the preferred disposition of adhesive means may optionally be indicated in the layer names, e.g., by calling layers 150 and 300 "double-sided adhesive layers." As will be apparent to those skilled in the art, adhesives can be disposed on appropriate portions and surfaces of various layers including others such as 200, 250, 350 and 400, in order to achieve the proper assembly of the sensor, or alternatively, processes such as heat bonding or ultrasonic or laser welding can be employed to eliminate the use of adhesives. The physical surface-to-surface attachment vs. simple juxtaposition of layers can be significant to the proper functioning of the sensor due to "bounding" effects on the liquid absorbency and flow properties of the porous/absorbent layers. Establishing a boundary, or "bounding" a surface of a thin absorbent layer, by sealing it with an adhesive or other impermeable coating, blocks off air contact across the surface that would otherwise break (reduce) the average magnitude of cross-sectional pore capillary tension that pulls a liquid transversely through the layer. Such bounding causes a liquid to spread more rapidly in the layer—while decreasing or eliminating the layer's surface absorption ability—in other words, its ability to "collect" through the surface that is bounded. For example, completely bounding both the top and bottom of a thin absorbent layer would tend to maximize the transverse or lateral spreading rate of a liquid, but would also eliminate its surface absorbent ability. (Note that the terms, "transverse" and "lateral" will be used interchangeably in this discussion to denote spreading flow in a layer of material, as opposed to "normal" or "through" which interchangeably denote flow "into" or "out of" a layer or layers relatively perpendicular to the approximate plane of the layer(s).) Surface absorbency and lateral spreading rate may be tailored by adjusting the "open area" or percentage of surface that is not bounded (e.g., by providing "pin-holes" or other interruptions in the bounding adhesive or coating, or by use of a dissolvable coating). Lateral spreading can also be accomplished by virtue of the relative permeability or absorbency of adjacent layers, such that the choice of materials employed can determine the primary direction of flow through and around the sensor. Thus, the term "relatively impermeable" is employed to describe layer 300 in order to stress its function of providing a baffle between the sensing means 200 and the origin of liquid to be sensed.

Figure 3A:
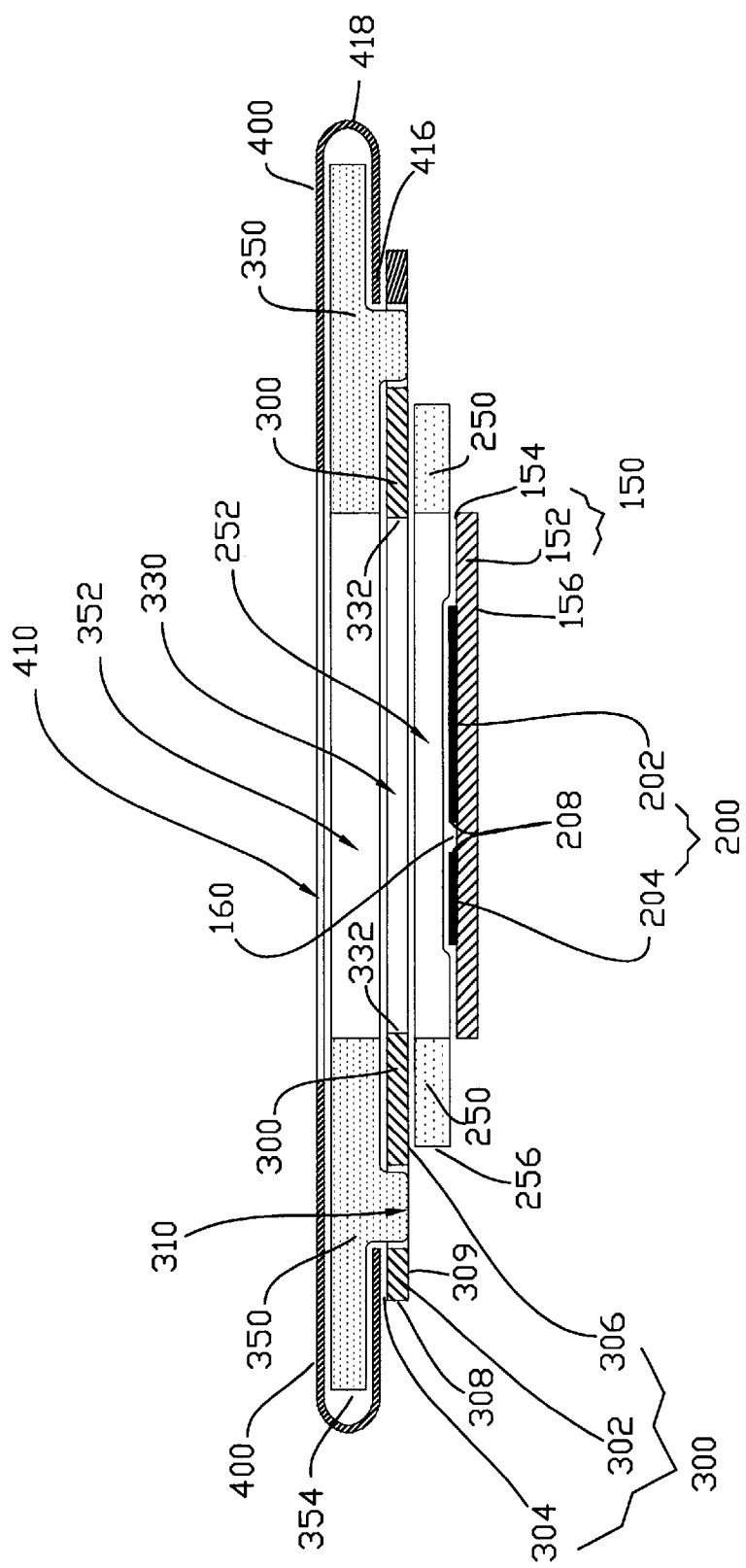
Figure 3B:
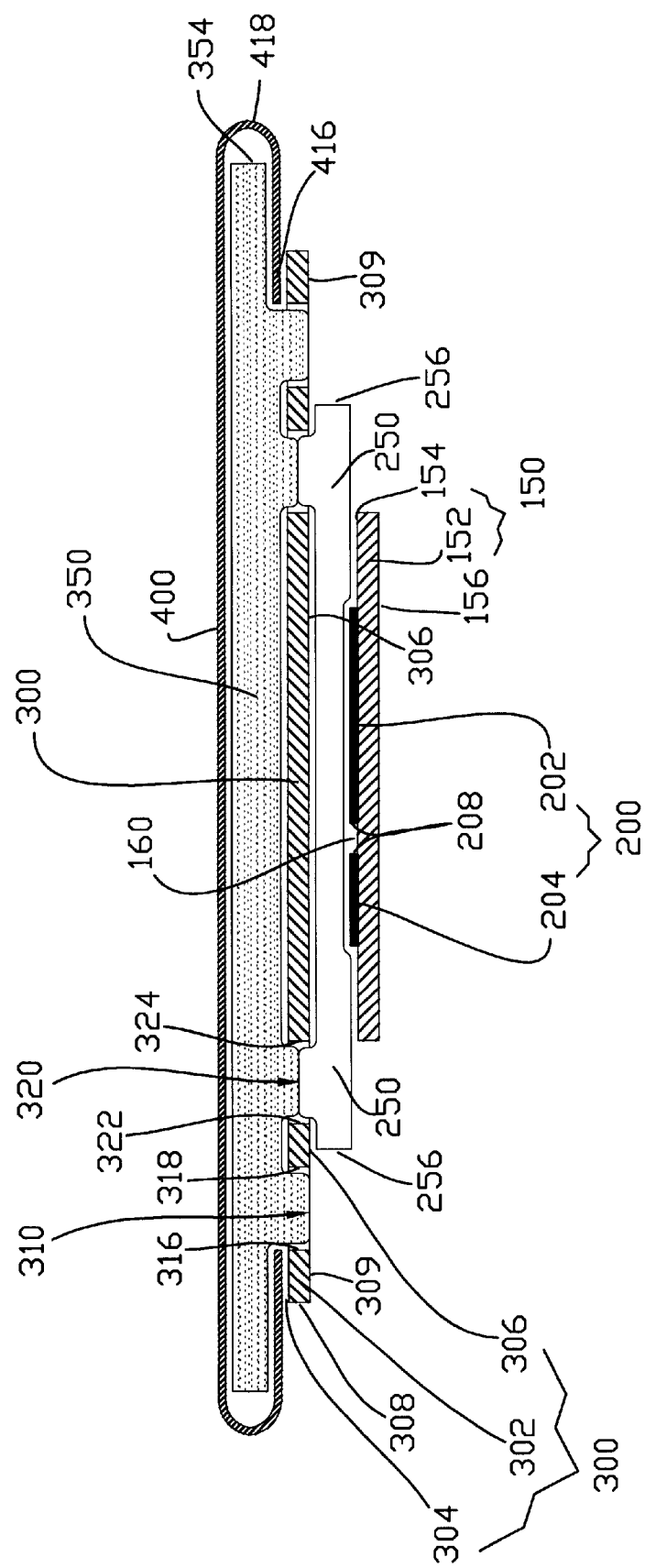

In some cases, as explained above, physical attachment via adhesive is preferable and can contribute to calibration of the sensor for desired alarm response. It also helps maximize through-flow into the diaper. For example, as shown in FIG. 3B, lower absorbent layer 250, upper impermeable layer 300, and upper absorbent layer 350 are preferably adhesively joined by double-sided adhesive on layer 300, placing the two absorbent layers 250 and 350 in constant, direct contact through the openings indicated by reference number 320. This constant and predictable contact is important to the "flow-splitting" characteristics of the sensor, whereby the urine that is initially absorbed through cover layer 400 into absorbent layer 350 wicks laterally across the central portion of impermeable barrier layer 300 and through openings 320, preferentially flowing "downward" into the diaper. This through-flow continues until the diaper's rate of surface absorption diminishes (with increasing saturation of its absorbent bulk and/or rapid flow into the surface) below that of absorbent layer 250, at which point at least a portion of the total flow through openings 320 does not go into the diaper, but instead laterally splits off from the main flow and goes through absorbent layer 250 and therethrough to the conductive layer 200. Another example of advantageous adhesion of absorbent layers is that the transfer efficiency of relatively high-volume flow through the sensor into the diaper via a series of "spillway" openings 310 is substantially increased by securely adhering the area surrounding the openings 310 to the diaper surface. This ensures that the upper absorbent layer 350 remains in constant direct contact with the diaper surface through holes 310, to provide capillary continuity through the otherwise impermeable layer 300.

In other cases, however, physical attachment is not preferable. For example, as can be seen in FIG. 3B, cover layer 400 can be "free floating" or affixed with respect to the top surface of upper absorbent layer 350. By leaving layers 350 and 400 juxtaposed but not adhered, they remain unbounded, thus enhancing the ability of layer 350 to quickly absorb an initial flow of urine, and preventing "splash-back" in the region of the diaper covered by the sensor. A lack of adhesion here also contributes to skin-contact comfort and the pliability of the sensor, and thus its conformance to the ever-changing shape of a diaper. This is because cover 400 can readily slide over layer 350, thereby increasing the flexibility of the entire sensor.

The Bottom Removable Protective Layer of Sensor 100

Removable protective layer 110 in a preferred add-on embodiment is typically employed as packaging to preserve the cleanliness of the sensor, while permitting it to be folded or rolled. Layer 110 also facilitates application and assembly of the system by providing strippable protection of certain preferably adhesive surfaces of the sensor. As illustrated in FIG. 4 and FIG. 6, layer 110 has strippable portion 112 that releaseably adheres to, and has approximately the same width as (or preferably slightly greater width than), double-sided adhesive layers 300 and 452. The material used for strippable portion 112 must be consistent with the characteristics of the adhesive to which it must releaseably adhere, such as a thin paper with a nonporous plastic or waxy coating having characteristically low bond strength with the adhesive to be covered. (Such covering material is typically specified for best compatibility with specific adhesive tapes from manufacturers such as 3-M.) Extending on either side of strippable portion 112 is an optional wrapping portion 114, which extends sufficiently to fold around the entire sensor means 100. The material used for wrapping portion 114 must be thin, light, foldable, and disposable; such as polyethylene or vinyl sheet, preferably about 0.001-inch in thickness or less. It can optionally be fabricated of the same material as strippable portion 112, with the attendant advantage of reducing the number of materials required and eliminating a lamination step in the manufacturing process. At one end of wrapping portion 1 14 is adhesive tape piece 116 for retaining the assembly in a clean folded or rolled condition prior to use. Wrapping portion 114/116 may not be needed if sensors are bulk-packaged (e.g., in a plastic bag of sensors stacked flat) and, as mentioned, entire protective layer 110 is not required in a pre-incorporated disposable diaper embodiment of the sensor.

The "Inside-the-Diaper" Portion of Sensor 100

Figure 3C:
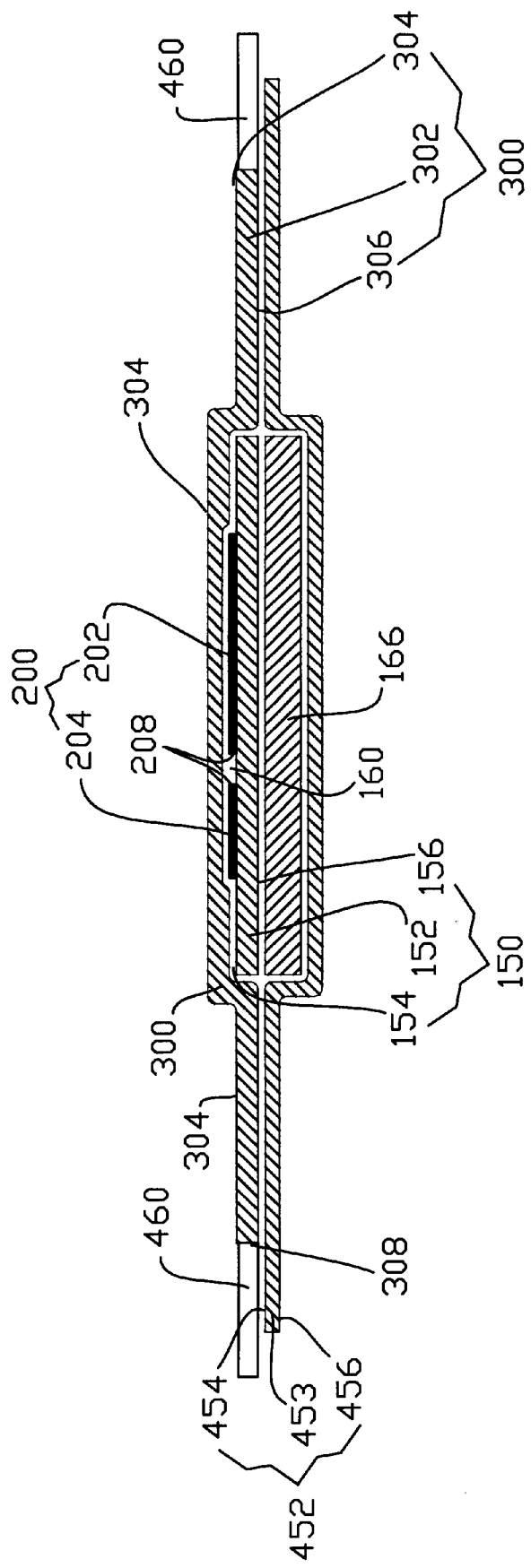

Lower relatively impermeable layer 150 shown in FIG. 3 and FIG. 11, can serve as means for affixing sensor 100 to the diaper or other environment of use. As illustrated in FIG. 3B, layer 150 has a center core 152, optionally but preferably provided with upper 154 and lower 156 adhesives. Layer 150 also provides structural support, holding electrically conductive layer 200 in place, maintaining elements 202 and 204 nominally parallel and a pre-determined distance apart and also defining a channel 160 therebetween. By being fabricated of liquid resistant or impermeable material(s), layer 150 also serves to trap moisture in channel 160. Layer 150 also adheres to portions of absorbent layer 250 and therethrough to the remainder of sensor means 100, which is thereby also affixed to the diaper. The material for impermeable layer 150 is typically a thin (approximately 0.001 inch thick), flexible but dimensionally stable tape of liquid impermeable paper or preferably plastic such as acetate, vinyl, polyethylene, polypropylene, polyester, or the like. Layer 150, and therefore core 152 is, with the exception of conductive layer 200, the narrowest layer of sensor means 100. In a preferred embodiment, as shown in FIG. 3 and FIG. 11, layer 150 is approximately 0.75 inches wide and 0.003 inch thick, with an optionally narrower portion 162 in the front (near end 164). This narrower portion approximately matches the overall width of electrically conductive elements 202 and 204 of layer 200 so that upper adhesive 154 of layer 150 is not exposed at the front connective end 162 of layer 150 above tab stiffener 166 as shown in FIG. 5A. Tab stiffener 166, shown in FIG. 3C and FIG. 10, is fabricated from a preferably thicker, stiffer material than core 152 (such as 0.010 inch thick polyester sheet) and is adhered to the lower adhesive 156 of layer 150. Tab stiffener 166 serves as structural support for layers 150 and 200 and preferably also as an active spring element for the releasable connection between sensor 100 and monitor 500 as shown in FIG. 5A and FIG. 5B. The combination of tab stiffener 166 with the front portions of layers 150 and 200 comprises male connector tab assembly 170 of sensor 100, as shown in FIG. 4 and FIG. 5A. As will be further described with respect to the releasable electronic coupling and retention portion 450 of the sensor, this tab assembly also helps locate and retain monitor unit 500 when it is connected to sensor 100 and installed on a diaper for use, as shown in the close-up side view of FIG. 5B. As shown in FIG. 11, portion 162 of impermeable layer 150 is, in a preferred embodiment, 0.5 inches in width and tab stiffener 166 is preferably 0.75 inches in width which is slightly less than the width of a recessed connector-receiving portion 600 of monitor/alarm unit 500 which receives tab portion 170 of the sensor for electrical and mechanical connection purposes as shown in FIG. 20. The material used for upper adhesive 154, as shown in FIG. 3A, FIG. 3B and FIG. 3C, is selected to form a strong, preferably permanent attachment to conductive layer 200 and absorbent layer 250. Adhesive 154 should be a non-absorbent, non-transmissive adhesive, like the pressure-sensitive adhesive on typical 3-M "Scotch" brand tapes. Alternatively, it can be a layer of heat melting adhesive, or one or more of the material surfaces themselves can be melted together for attachment. The material used for lower adhesive 156 is selected to releaseably adhere to protective layer 110; it can be the same as upper adhesive 154, depending on the nature of strippable portion 112 of protective layer 110. Layer 150 can be obtained with the adhesives 154 and 156 already applied or alternatively, the adhesives can be applied as part of the assembly process. Layer 150 may preferably be cut from 0.75-inch wide, double-sticky tape (such as 3-M type 665), which is readily available pre-spooled in the desired width.

In a pre-incorporated disposable diaper embodiment of the invention, lower adhesive 156 can optionally be replaced by alternative means (such as heat bonding or use of a sewn portion or a recessed channel or folds in the diaper's absorbent core material) for receiving/affixing the sensor means in place within the diaper, or the sensor can be instead attached to an inner cover layer or other part of the diaper, as proves most economical for manufacturing.

As illustrated in FIG. 12, conductive strips layer 200 has first 202 and second 204 conductive members. Members 202 and 204 each have an outer edge 206 and an inner edge 208. They are maintained substantially parallel to each other by top adhesive 154 of layer 150, and (most simply) a fixed distance apart (preferably about 0.010 to 0.125 inch and most preferably 0.045 inch). The materials used for conductive members 202 and 204, and their dimensions, taken together with those of channel 160 and the material of which they are made, in part determine the sensitivity of sensor 100 and the entire system. Conductive members 202 and 204 can be made of different materials, or preferably the same material, such as laminated thin metallic foil (e.g., 0.001 inch thick aluminum), or vacuum-deposited metal or semiconductor, or printed conductive ink, paint, ionic jell, dissolvable salt or other liquid-enabled conductor, or doped polymer material.

The spacing of conductive members 202 and 204 which defines the width of channel 160 may be set (or even vary) over a considerable range (e.g., about 0.010–0.5 inch), but with suitable compensation in the choice of certain electronic component values in monitor unit 500 to achieve the desired threshold of sensitivity. The conductivity of urine and feces varies over a wide range and careful compromise in the setting of design parameters is required to reliably detect both urine and feces. Even with appropriate component value selection, however, other factors tend to make the preferred range of spacing (as well as conductor width) more limited in practice. In general, too small spacing of channel 160 could cause production difficulty to ensure that the two conductive strips never touch or short (including at end 164 where the sensor attaches to a set of monitor unit connecting contacts 620, 622 and 624 as shown in FIG. 5B and FIG. 20). Also, too small spacing increases the susceptibility of the sensor to damage or to irrelevant contaminating particles which might accidentally bridge the conductors. Similarly, condensation from nearby perspiring skin or even high ambient humidity could be troublesome if the spacing is too small. Up to a point, the smaller the spacing, the more electronically noise-resistant the system can theoretically be made, but at the expense of more power consumption because the current flow between the conductors is greater in magnitude during sensing, especially when elimination material is bridging the conductors. On the other hand, too large a spacing necessitates unrealistically high reference impedance to detect the presence of relatively low-conductivity feces, particularly of the drier variety. Larger spacing also means that a series of feces-intrusion openings 252, 330, 352 and 410 (as shown in FIG. 13, FIG. 14, FIG. 15 and FIG. 16, respectively), need to be wider to span both conductors and relatively more feces would need to be present for reliable detection. Too large openings could also undesirably allow the diaper wearer's skin to press into the openings and possibly to touch or even bridge the conductive strips.

Members 202 and 204 can have different widths (about 0.305 and 0.130 inch, respectively, in a preferred embodiment) but preferably the same thickness (typically 0.001-inch or less), to minimize perceivable stiffness and destructive stress in repeated flexure of the sensor. In practicality, both the width and the spacing of the conductive strips may be chosen to coincide with the minimum practical connector spacing and contact overlap at the connector tab portion 170 (as shown in FIG. 20). Minimizing the total area of layer 200 is desirable, because the total exposed conductor area, divided by the average conductor gap, is proportional to the total electrical capacitance of the sensor. The higher the sensor capacitance, the greater the electronic and electrical noise susceptibility of the system, and also the greater the required power to operate the sensor. Finally, relatively larger active sensor area (defined by the outer "footprint" of conductive elements 200) would undesirably result in greater obstruction of flow from source (the diaper wearer) to bulk absorber (the diaper), because lower impermeable layer 150 (which separates conductive strips 202 and 204 from the diaper layers below) allows no direct downward (through) flow anywhere in this lengthwise central area of the sensor.

As previously described, either member 202 or 204 can be the larger or smaller without affecting the function of the sensor means. In a preferred embodiment, the wider conductive strip 202 is preferably used to bridge the pair of contacts 620 and 622 in monitor unit 500 where the ends of the strips are brought out into either a flexible or rigid connector tab configuration (as shown in FIG. 20.). This allows the simple insertion of the connector tab portion of the sensor into the monitor unit (as also shown in FIG. 5B) to conveniently serve as the only power-on/off control needed in the system. Constant-width over the entire length of the strips is desirable for manufacturing with roll-fed metal foil conductive materials, but is obviously not necessary for either deposited or printed-on conductive strips, in which case the width of one strip could easily be made larger than the other only at the connector end, or the elements of layer 200 could take various other shapes.

As will be further discussed with respect to monitor/alarm unit 500, the conductive strips are subjected, via releasable connection to the monitor unit circuit, to time-spaced (approximately every 3-seconds) brief (approximately 0.1-sec duration) low-voltage (under 3v) fast rise-time (preferably less than 1 u-sec) square-wave pulses which are variably conducted by any material in "trap" channel 160 between the conductor strips, to allow a proportional average electrical current (ranging from zero to approximately 1 micro-ampere) to flow between the strips during the duration of each pulse. The magnitude of current depends on the "bulk ionic" and "skin" conductivity of the material bridging the conductor strips as well as the geometry and spacing of the effective current path. A level of resulting current flow during any of these pulses that exceed a preset threshold level preferably causes the monitor unit to either "beep" audibly or flash a visible alarm to signal the caregiver that the diaper or other absorber needs changing. As previously mentioned, double or multiple pulses are preferred over single ones—for more effective alarm communication to the caregiver.

As illustrated in FIG. 3, and FIG. 13, porous, absorbent layer 250 is generally rectangular in shape, somewhat wider than double-sided adhesive layer 150, and has a series of elongated openings 252 disposed toward its distal end 254. (These openings can alternatively be described as conduits, channels, passageways, perforations, holes or the like, and are provided for feces-specific detection purposes—as shall be fully explained as the other layers of sensor 100 are described.) The length of layer 250 nominally extends from just over fold line 342, when installed at the front rim of a diaper, down and throughout the full length of the portion of the sensor that goes inside a diaper. Layer 250 is made of a typically cellulose-based, highly absorbent paper or cloth, or similar natural or synthetic, hydrophilic material of either woven or non-woven composition, the choice of which will depend on manufacturing economics and the purposes to be accomplished by the layer. Its thickness, in a preferred embodiment, is about 0.01–0.06 inch (uncompressed) but may be selected from a considerable range, the choice of which primarily affects the response delay time of the sensor to urination events. Greater thickness increases the relative liquid buffering and volume carrying abilities of the layer, as opposed to the transverse spreading rate of liquid through the layer. The relative width, and particularly the material and composition of absorbent layer 250 also contributes to determine its characteristics, as described below.

A significant characteristic of liquid-porous (absorbent) media in general, is the average pore size or channel dimension of the material, which, along with the surface tension between the material and a given liquid, determines its average "capillary tension" or relative ability to draw liquid from an adjacent absorbent porous material. A material with relatively smaller average pore or channel size is able to draw liquid from an adjoining volume of similar material having relatively larger average pore or channel size. Moreover, for low viscosity liquids, the smaller the average pore size, the faster a material will absorb liquid because absorption rate is proportional to average capillary tension (measured in units of vacuum), which in turn depends on the average empty-pore surface-to-volume ratio as well as the % of empty pore capacity currently available to hold more liquid (i.e., the available "absorbent capacity", usually expressed as a % by either volume or weight).

The instantaneous absorption rate across a surface (such as the inside of a diaper) changes, depending on the balance between how rapidly liquid is arriving at the exposed surface (to be absorbed) and how fast it can be wicked away into the bulk of the material's volume. As available absorbent capacity diminishes over time, due to accumulation of liquid throughout its bulk, the maximum (usually initial) absorption rate into the surface is reduced because the average capillary tension is reduced. If liquid arrives at the junction of two materials having substantially different capillary tension, such as the interface of a diaper surface and porous layer 250 of sensor 100, relatively more (or even virtually all) of the flow will go into the material with the higher tension (initially the diaper), until the tension of the diaper material eventually drops (due to liquid urine accumulation) to a lower value than that of layer 250. This "splitting" of the flow may also happen at any time, if the incoming flow is so fast as to "overwhelm" the maximum absorbent rate capacity of the diaper surface, regardless of whether the diaper's total absorbent capacity has become saturated.

As illustrated in FIG. 3, FIG. 3A, FIG. 3B and FIG. 14, second relatively impermeable layer 300 is the backbone (and for certain processes the manufacturing substrate) of sensor 100. As with layer 150, layer 300 has a center core 302, optionally but preferably provided with an upper 304 and a lower 306 adhesive, each made of materials similar to, or as described with reference to layer 150, except that in a preferred embodiment as illustrated, layer 300 is approximately 1.5 inches in width. Also in this embodiment, layer 300 is preferably approximately 0.001–0.003 inch thick, and can be punched from 1.50-inch wide, pre-spooled, double-sticky paper or plastic tape, preferably being relatively liquid impermeable and hydrophobic (i.e., tending to not be "wettable" by aqueous solutions such as urine), and having good dimensional stability, high torsional flexibility and suitably aggressive adhesive (such as type DT-42, manufactured by Manco, Inc. of Westlake, Ohio). Layer 300 is provided with a plurality of openings, each preferably extending through core 302 and both adhesives 304 and 306, primarily disposed toward the outer edges 308. In addition to flow-related functions, this plurality of openings contributes to the mechanical flexibility and compliance of sensor 100, by reducing the overall stiffness of its combined layers.

Referring again to FIG. 3, FIG. 3B and FIG. 14, a first series of openings 310, is preferably symmetrically disposed towards outer edges 308 of layer 300. While most shapes will serve the function, rectangular or elongated outer openings are preferred. This provides the best balance in the use of available surface area for the impermeable adhesion of layer 400 to layer 300 (along edges 308 as shown in FIG. 3B), without compromising either the structural integrity of layer 300 or the sensor's capability to permit rapid liquid flow into a diaper. As shown in FIG. 14, each of openings 310 have a front-most edge 312, rear-most edge 314, outermost edge 316 and innermost edge 318.

A second series of openings 320 (also shown as being preferably rectangular for similar reasons, although most other shapes could be employed) is preferably symmetrically disposed inward of openings 310 (towards the center of layer 300), with the centers of the openings approximately co-linear with the midpoints between each front-most 312 and rear-most 314 edge of openings 310. This relatively staggered disposition of openings 310 and 320 serves to maximize the structural integrity of layer 300 without impeding through-flow. It also helps ensure that, regardless of the path taken by any outward flow across the top of impermeable layer 300, the flow distance to reach the diaper through openings 310 and over edges 308 will be minimized, while at least some of the flow will be practically certain to enter openings 320 and thereby be conducted into absorbent layer 250. As illustrated in FIG. 3B, the outermost edges 322 of second series 320 is positioned closely adjacent the outer edge 256 of absorbent layer 250 and the innermost edge 318 of openings 310, most preferably with outermost edge 256 directly aligned midway between edges 318 and 322. Through this arrangement, the first series 310 acts as a "spillway" to conduct liquid rapidly and directly to the diaper, while the second series of "flow-splitting" openings 320 conducts liquid into the absorbent layer 250. The capillary absorbent characteristics of the material employed for layer 250, relative to the material of the diaper surface, will determine if, and at what rate, such liquid is wicked transversely inward through layer 250 towards channel 160—as opposed to such liquid being absorbed either completely or partially downward into the diaper through the bottom surface portion of layer 250 (outward of the side edges of shielding/trapping impermeable layer 150). The arrival of such liquid, wicking laterally inward through layer 250 and thus to channel 160, will increase the measurable conductivity between members 202 and 204. Upon reaching an appropriately pre-determined threshold level of conductivity (or change, or rate-of-change of conductivity, or similar change in any other suitable property resulting from the arrival of such liquid), the circuit of monitor/alarm unit 500, releaseably connected to conductive members 202 and 204, is effectively triggered. This condition then initiates an alarm indication by the monitor unit that the diaper needs changing.

A third series of openings 330 in layer 300 is preferably shaped like and disposed directly above and in communication with elongated openings 252, and therethrough to conductive members 202 and 204. As shown in FIG. 3, FIG. 13 and FIG. 14, openings 330 and 252 are preferably disposed along the central portion of sensor 100, towards the distal end, approximately midway between some of openings 320 and extend laterally outward approximately to a line connecting the innermost portions 324 of openings 320. It is further preferred to have a matching number of elongated openings 330 and 252. In FIG. 3A it can be seen that, while other shapes will serve the function, the laterally elongated shapes are particularly suited to efficiently conducting semi-solid and liquid fecal matter to channel 160, thereby directly contacting conductive members 202 and 204 to facilitate the detection of feces, which had heretofore presented considerable difficulties. The location and concentration of openings 330 and 252 only towards the rear, or distal end, of sensor 100 disposes these conduits towards the most likely concentration of feces, and posterior to the most likely origin of urine, and particularly away from directly-impinging streams of urine. This arrangement prevents erroneous pre-triggering of the system, by eliminating the likelihood that directly-impinging urine streams will enter through the feces-selective detection openings to contact conductive layer 200.

As shown in FIG. 3B, absorbent layer 250 is bounded by means of adhesive contact on the bottom side with layer 150 (except those portions in direct contact with conductive elements 202 and 204), and also by adhesive contact on the top side with layer 300. This bounding causes the lateral spreading rate within layer 250 to be increased and the "capillary trap" nature of channel 160 (defined by the inner edges 208 of members 202 and 204, the upper adhesive surface of layer 150, and the lower surface of layer 250) to be enhanced. Also, because channel 160 is filled with the somewhat resilient porous media 250 (except in the locations of feces-selective detection openings 330 and 252), a sufficiently strong capillary nature is imparted to channel 160 for retaining the liquid material to be sensed. This "capillary trap" is capable of retaining enough relatively conductive elimination material, long after it initially arrives into the trap, to eliminate the need for any functional "latching" of an over-threshold level of conductivity condition (as measured across conductive elements 202 and 204) on the part of monitor unit 500. This feature of the sensor is important because it enables the monitor to have very high electronic sensitivity to the very low typical conductivity produced by bridging the conductive strips 202 and 204 with fecal matter—and yet to operate in a repetitively self-correcting (i.e., "self-resetting" as opposed to "latching") mode in the presence of electrical noise or interference, or any momentary bridging (relative shorting) of the conductor strips for any reason. As mentioned previously, a common problem with electronic sensing devices that "latch" on the momentary attainment of a preset threshold level of any measurable quantity is that they can, particularly if operating at high sensitivity, be inappropriately and permanently triggered by insignificant conditions.

Considering other design aspects involving the interrelationships of layers, layer 150 has to be wider than the overall "footprint" of conductive strips 202 and 204 because otherwise, unless the strips were made of conductive adhesive, there would be no exposed adhesive area to stick to absorbent layer 250 other than in the narrow gap between the strips. If conductive adhesive is used, a non-adhesive portion should be provided at the connector end of strips 202 and 204 (where the strips themselves also function as the sliding connective elements for releasable communication with electronic monitor unit 500 as shown in FIG. 5A and FIG. 5B). Layer 150 is also preferably sticky on its bottom to adhere the whole sensor to the diaper along the lengthwise centerline. As previously mentioned, this is desirable for secure attachment—and also for adequate conformance by the sensor to the diaper's varying shape. This also helps maintain good capillary contact of the exposed areas of the bottom of absorbent layer 250 (at edges 256 outboard of layer 150) with the diaper surface—thereby facilitating both maximum urine through-flow and appropriate monitor system response (see FIG. 3B).

In still other interrelating aspects, impermeable layer 150 "protects" the capillary well or trap of channel 160 and also the lateral flow (coming from around impermeable layer 300 and through flow-splitting holes 320 and continuing inward through absorbent layer 250) from being uncontrollably "robbed", or depleted of urine, by the diaper surface from below. The more exposed surface area of absorbent layer 250 that is in contact with the diaper between flow splitting holes 320 and the outer edges of impermeable layer 150, the less sensitive the response of the sensor becomes (relative to the diaper surface absorbency), because the lateral flow that would otherwise cause triggering of the monitor unit is relatively more likely to be absorbed into the diaper before it can get to capillary trap 160 between conductive elements 202 and 204. Conversely, if flow-splitting holes 320 are laterally repositioned relatively inward, to be partially or even completely above impermeable layer 150, the sensor response can thereby be changed, if desired, to allow triggering of an alarm after a certain minimum volume of urine has been discharged, with less or even practically no dependence on the remaining absorbent capability of the diaper below.

Again referring to FIG. 3B, the relative width of layer 150 vis-à-vis the lateral positioning of flow-splitting holes 320 is thus one means usable to easily "fine-tune" the urination-response of sensor 100 to reflect the desired traditional criteria (and to adjust for diaper material properties). "Coarse tuning" can be done by selecting, relative to the diaper materials, the average pore size or other appropriate properties of absorbent layers 250 and 350. (These layers are made of materials normally available "off-the-shelf" with only stepwise-varying and limited range of absorbency properties.) A preferred combination of parameters must produce the desired response sensitivity and also have sufficient areas for adhesion (or other means of attachment) on layer 150, with the narrowest possible core 152. This narrowness is important because the smaller the overall "footprint" of impermeable layer 150, the more "transparent" the whole sensor can be made to the rapid flow of urine into a diaper—and also, the more flexible and compliant the sensor can be made.

As previously explained, the difference in respective capillary or absorbent tension at the junction of layer 250 and the diaper surface is a key means of "flow-splitting" for the purpose of monitoring diaper condition during and after urination events. However, triggering of the sensor does not necessarily depend on what the overall "degree of saturation" or "filled percentage" of layer 250 itself is at any given time—either as compared to the diaper surface, or absolutely. This is true, because only part of layer 250 needs to reach saturation in a cross-sectional "conduit", of even very small dimensions. This conduit can become gradually filled with sufficient liquid volume, in response to urination events, to reach and trigger the detector means (by bridging members 202 and 204 in channel 160). Therefore, in an alternate sensor embodiment, even a non-absorbent capillary layer or other liquid transport device could serve the function of layer 250 in conducting liquid to a sensing means, leaving the surface-condition discrimination function to a separate element, or even eliminating it entirely. Because "flow-splitting" in conjunction with liquid transit delay can be employed to somewhat proportionally track the total volume of flow into a diaper (as opposed to, or in addition to, monitoring the diaper's remaining surface absorbent properties), this mechanism can also be exploited to modify the sensor response. For example, if lower absorbent layer 250 is made thicker, relative to its area, it will tend to act more like a "time delay" element, and less like a "tension discrimination" element, because at greater distance away from the diaper surface (vertically), the lateral flow is less affected by the diaper. This is particularly true at the top surface of layer 250 that is bounded by upper impermeable layer 300. Alternate embodiments of sensor 100 could be configured with materials and dimensions chosen such that the delay in triggering of the sensor after one or more elimination event(s) depends primarily or even completely on the time-delay of lateral propagation as described above (instead of primarily on relative capillary tension of the contacting surfaces). Such arrangement would achieve substantially the same purpose of allowing the diaper to function effectively (i.e., by allowing it to absorb some quantity and/or relatively low flow rate of elimination material during a delay period) before causing monitor/alarm unit 500 to produce an on-going "ready-for-diaper-change" indication. For example, larger portions or even the entire lower surface of absorbent layer 250 can be bounded by an impermeable layer, such that elimination material can enter layer 250 from either above (such as through holes in baffle layer 300) or alternatively from around a baffle layer. Such material would then travel laterally, over a period of time, to the sensing point, triggering a detector. Holes through the impermeable baffle can also extend through layer 250 and/or the lower bounding layer to allow more of the elimination material to flow through the sensor into the absorber.

In a variation of the preferred embodiment, as suggested above, it is also possible for an upper layer or layers of the diaper itself to serve the purpose of absorbent layer 250, relative to the rest of the diaper beneath it. In this case, the detector means, such as the conductive strips 202 and 204 in the preferred embodiment, could be disposed on the bottom of impermeable layer 300. A portion of the same layer 300 could also be adapted to form a relatively narrower tab-like connector structure at its proximal end (either with or without additional laminated layers) to connect with a monitor unit. Such configuration could thereby also eliminate the need for layer 150. This approach is shown with reference to connector tab assembly portion 170 of the pre-incorporated sensor embodiment in FIG. 22C. Such arrangement would not, of course, benefit from the liquid-trapping and shielding effects provided by layer 150 in the preferred embodiment, but it could offer even lower sensor cost. It would also be possible to dispose a material having absorbent properties that are different from the rest of a diaper, under an impermeable layer and in contact with the sensing means (such as conductive elements 202 and 204), to effectively trap moisture or liquid, thereby serving the function of capillary trap portion 160 and facilitating an appropriate sensor response.

In still other alternate embodiments, any appropriate detector means could be located under (or shielded by) the effective baffle of a relatively impermeable element (such as layer 300) to receive elimination flow presented through openings in (or around the edges of) such a baffle. This flow would appropriately affect the detector means by causing a change in a suitable measured quantity due to the combination of sufficient liquid accumulation and/or flow. The detector means would then cause an alarm signal or indication to be produced, reflecting a desired set of criteria for appropriately determining the need for elimination-absorber changing.

As illustrated in FIG. 3, FIG. 3A, FIG. 3B, FIG. 4 and FIG. 15, porous, absorbent, collecting/spreading layer 350 is generally rectangular in shape, approximately the same width as layer 300, but preferably slightly wider to provide a floating soft edge. Absorbent layer 350 also has a series of elongated openings 352, preferably shaped like and disposed directly above and in communication with an equal number of elongated openings 252 and openings 330 for feces-specific detection purposes, as will be further explained below. The materials for absorbent layer 350 may be approximately the same thickness and selected from the same types as used for layer 250. In a preferred embodiment, however, layer 250 may be designed to have somewhat lower initial absorbency relative to the contacting diaper layers for the purpose of directing urine flow preferentially into the diaper until the diaper's absorbency is significantly reduced. On the other hand, the absorbency of layer 350 is chosen to be as high as is practical, to prevent urine "splash-back" and to readily collect urine flow impinging anywhere on its upper surface. Layer 350 also assists in preventing premature triggering of the sensor by absorbing and buffering a significant volume of urine, and having the capillary or wicking characteristics to rapidly conduct fluid towards the outer edges 354. Preferably, by bounding absorbent layer 350 by directly adhering it to impermeable layer 300, or by otherwise coating it with impermeable material, the lateral liquid capturing and/or spreading characteristic of layer 350 is enhanced. Such direct adherence of both absorbent layers 250 and 350 to the bottom and top surfaces, respectively, of impermeable layer 300 also facilitates rapid and predictable flow of liquid through "low-splitting" holes 320 in layer 300, by maintaining the mutual capillary contact of absorbent layers 250 and 350 through these holes, as can be seen in FIG. 3B.

As shown in FIG. 3A, urine is prevented from flowing indirectly to the conductive elements 202 and 204 via seepage (i.e., capillary flow) from porous layer 350 through the feces-specific detection openings 352, 330 and 252, because these openings in both absorbent layers 350 and 250 are aligned with, (and in some embodiments slightly larger than) openings 330 in layer 300 such that the two absorbent layers do not touch each other through impermeable (and preferably hydrophobic) layer 300. This capillary gap, as indicated by reference number 332, eliminates any seepage path for urine through the effectively selective feces-specific detection openings. As will be apparent to those skilled in the art, the manufacturing method used to punch or otherwise create feces detection openings 352, 330 and 252, must cut cleanly—so as to not allow capillary fragments of layers 350 and 250 to remain in the area of openings 330 in layer 300.

It is possible, in an alternate embodiment, for layer 350 to have suitable openings in its surface and to be made wide enough to wrap completely around impermeable layer 300, and thus also function as absorbent layer 250. In this case, adhesive could be applied to the bottom outer edges of combined layer 250/350, or some other means could be used to hold sensor 100 to the diaper.

In yet another alternate embodiment, impermeable layer 300 can be made narrower, similar to or the same width as impermeable layer 150, so that there is no need for punching either "spillway holes" 310 or "flow-splitting holes" 320 through layer 300. In this case, suitable adhesive or other means (such as heat-bonding) could be employed to keep the absorbent layers together (at least in places) and also optionally to hold the sensor in good contact with the diaper surface. In an embodiment wherein the sensor is incorporated into a diaper, the surrounding layers of the diaper could serve this purpose. If layer 300 is made narrower to eliminate holes 310 and 320, layer 300 can still be wider at the proximal end of the sensor forward of some point near fold-line 342, or it can be affixed to a separate wider assembly for the various purposes of attachment to, location of, and retention of monitor unit 500 at the top front of a diaper. As previously stated, various aspects of the proximal ("outside the diaper") portion of the sensor structure shall be further described later in the specification, with respect to the releasable electronic coupling and retention portion 450.

As illustrated in FIG. 1, FIG. 2A, FIG. 2B, FIG. 3, FIG. 3A, FIG. 3B, FIG. 4 and FIG. 16, cover layer 400 is the top most layer (when the sensor is installed on a diaper for use). It contacts the wearer's skin and is designed to provide comfort and protection from contact with the other layers. It has a top surface 402, a bottom surface 404 and outer side edges 406. Layer 400 must be soft, non-absorbent, and preferably highly porous or liquid transmissive, so as to be minimally obstructive to urine flow, while maintaining a relatively dry surface in contact with the skin. In a preferred embodiment, layer 400 can be made from a hydrophobic material, so that although urine can still be rapidly absorbed through its mesh of openings by layer 350, the top surface otherwise remains particularly dry. Suitable materials can include, for example, thin (preferably about 0.001 inch thick) webs or meshes of polyethylene, polyester, polypropylene, nylon or other heat-bondable fibers, as well as other polyolefins such as copolymers of polypropylene and polyethylene, or of linear low-density polyethylene. Webs are typically composed of micro-perforated film sheet or may be spun, woven, blown, foamed or otherwise fabricated. Composite materials combining, for example, thin non-woven fabric underlying a micro-perforated polymer film sheet or spun net or web can be employed to provide a comfortable, cushioned surface for skin contact. In an alternate embodiment, it is possible for such a composite form of layer 400 to effectively also serve as absorbent layer 350, thereby reducing the number of component layers.

As illustrated in FIG. 16, FIG. 3A and FIG. 3B, cover layer 400 is preferably somewhat wider than layer 350, in order to be folded around the outside of that layer. In this preferred embodiment, cover 400 (when folded) effectively defines the overall width of the sensor portion that is to be disposed inside a diaper. Edges 406 of layer 400 are folded over at the locations of outer phantom lines 412, encompassing the outer edges 354 of layer 350, and continue to the locations of inner phantom lines 414. As shown in FIG. 3B, a portion 416 of the folded edges of layer 400, somewhat smaller than the dimension between phantom lines 412 and 414 (shown in FIG. 16) ultimately covers (by being adhered to) the portion of upper adhesive 304 of impermeable layer 300 that extends outward from edges 316 of openings 310. As previously mentioned, the portions of layer 400 and layer 350 that extend outward beyond edges 308 of layer 300 provide a pair of floating soft edges 418 for the sensor. Portion 416 must not cover the outer-most row of openings 310 in layer 300, so that cover layer 400 does not interfere with or provide additional material through which urine must pass in flowing from collecting/spreading layer 350 through "spillway" openings 310 into the diaper.

The lower adhesive 306 on the bottom of layer 300 helps to maintain the direct capillary contact of absorbent layer 350 with the diaper surface below the sensor through holes 310, thus facilitating the flow of urine from layer 350 directly into the bulk absorbent layers of the diaper. As can be inferred from FIG. 1 and the side view of the layers in FIG. 4, the exposed portions of bottom adhesive 306 (not indicated explicitly in FIG. 4) of layer 300 are covered by strippable protective portion 112 of layer 110, which is intended to be removed prior to installation of sensor 100 on a diaper. In an alternate embodiment (as can be inferred from FIG. 3B), edges 406 can be folded to encompass layer 300 as well as layer 350, and thus to be adhered instead to portions 309 (outboard of edges 316) on the bottom of layer 300. In such case, portions 309 of lower adhesive 306 would not be available to stick the outer edges of sensor 100 to a diaper, as in the preferred embodiment. As will be apparent to those skilled in the art, the method chosen for combining or attaching cover 400 and layer 350 to layer 300 will depend on the manufacturing economics and relative advantages of using pre-adhesive tape materials versus selectively applying adhesives or of additionally employing other means such as heat bonding. In order to minimize high-volume manufacturing cost, it may well prove generally preferable to employ heat bonding or other means, instead of adhesives, for assembly of sensor 100, and to use adhesives primarily for the user-performed attachment and retention applications. In any case, however, it is desirable that the outermost portions of the sensor (except for any floating edges such as 418) be maintained in constant contact with the diaper surface. This effectively prevents the sensor from becoming uncomfortably bunched or creased inside the diaper. As described previously, it also improves efficient liquid conduction through the sensor. Edge adhesion additionally helps maintain good contact of the exposed portions of the bottom of layer 250 with the diaper surface, thus increasing the sensor's responsiveness to diaper condition.

As illustrated in FIG. 1, FIG. 3, FIG. 3A, and FIG. 16, layer 400 also has a series of elongated openings 410, preferably shaped like and disposed directly above and in communication with elongated openings 252, 330, and 352. These aligned openings offer direct conduits to the upper surfaces of electrically conductive members 202 and 204 for feces-specific detection purposes. In one embodiment, openings 410 are slightly narrower than openings 252, 330 and 352, or can be merely slits pre-cut through the material of layer 400 in order to provide additional protection against either urine-splash entrance, or direct contact between conductive layer 200 and the skin. The material of layer 400 is preferably sufficiently thin and flexible for openings 410 to be readily moved apart by the presence of feces, thus facilitating the efficient collection and intrusion of such material first through layer 400, and then through aligned openings 352, 330 and 252 and therethrough directly into contact with layer 200 upon elimination. In various embodiments, slits 410 can be adapted into flaps that remain nominally closed when feces are not present. In still other embodiments, somewhat wider openings can be used, or a series of small, possibly non-elongated openings of any shape could serve the function described. Regardless of the number, shape, or width of openings 410, each such opening must have at least one areal dimension sufficiently narrow with respect to (e.g., very roughly equal to) the overall depth of the aligned series of openings beneath it (as is determined by measurement of the minimum compressible assembled thickness of layers 400, 350 and 250). Such aspect ratio of the aligned openings effectively eliminates the possibility of a diaper wearer's skin ever being pressed into openings 410 deeply enough to touch members 202 and 204, and thereby compromise sensor performance—although such occurrence would not, in any case, be harmful to the wearer.

Functional Summary: Urination-Response in a Preferred-Embodiment Sensor 100

As discussed above (and referring to FIG. 2B and FIG. 3B), urine that is produced by the wearer of a sensor-equipped diaper is most likely to impinge on, and can readily pass through, cover layer 400 into absorbent layer 350. Layer 350's permeable, flow-collecting and lateral spreading material, preferably bounded at its bottom by adhesive contact with impermeable layer 300, can itself absorb small discharges of urine, while the top surface of cover layer 400 remains essentially dry. Higher volumes of urine rapidly spread throughout layer 350, and inevitably outward, where "spillway" openings 310 facilitate direct passage into the diaper. (Still higher rates of flow are easily accommodated over side edges 354 and 105.) Second series of "flow-splitting" openings 320 through layer 300 provides direct capillary contact for liquid transfer between absorbent layers 350 and 250, which also facilitate through-flow of urine into the diaper until such time as the diaper surface's absorbent properties become significantly degraded, relative to those of lower absorbent layer 250. When this occurs (or, in an alternate embodiment, after sufficient delay), urine can also be conducted towards channel 160 between conductive members 202 and 204, to bridge the gap therebetween, thus triggering releaseably connected monitor/alarm 500 at a time when the diaper's surface absorbent capabilities becomes significantly reduced, either due to total accumulation of urine, or to significantly high rate of urine flow (or optionally after a desired delay time). The capillary trap nature of channel 160 serves to "latch" such a triggered condition for an extended period (up to many hours).

Functional Summary: Defecation-Response in a Preferred-Embodiment Sensor 100

As discussed previously (and referring to FIG. 2B and FIG. 3A), sensor 100 responds selectively, yet immediately, to the presence of virtually any significant deposition of feces into a diaper. This response is distinctly different from the sensor's urination-related response as described above. Fecal matter deposited on the top surface of the sensor-equipped diaper is collected by means of the inevitable intrusion of such material into and through the sensor's aligned series of shallow, strategically disposed, elongated feces-specific detection openings 410, 352, 330 and 252, to directly contact and bridge conductive elements 202 and 204, which are connected to monitor unit 500. The diaper wearer's skin cannot penetrate these openings, because of the narrow gaps or nominally-closed slit-like elongated openings employed, relative to their depth. (Details of the electronic methods employed in monitor/alarm unit 500, to reliably detect even small quantities of low-conductivity fecal matter, shall be fully described with respect to the monitor unit later in the specification.) The described feces-specific detection structure and means employed by sensor 10 are specific to fecal matter, i.e., they do not compromise the previously-described urination-response, for two main reasons. Firstly, as previously described, the capillary flow properties of these aligned feces openings in the sensor effectively preclude the indirect seepage of urine from the upper absorbent layer 350 and through these openings to reach elements 202 and 204. Secondly, direct streams of urine are physically unlikely to target these openings, due to inherent physiological limitations on the origin and direction of such streams emanating from the wearer, relative to the disposition of the feces openings of the sensor. The relative location of these openings are disposed advantageously near or posterior to the most likely position of the diaper-wearer's perineal mid-line, to function as intended with both males and females.

Adjustment of the Composite Response of Sensor 100 to Reflect User Criteria

As previously described, adjustment of sensor response to correctly reflect traditional criteria for diaper-changing may be easily accomplished by means of altering the absolute and/or relative dimensions of the components, and/or selecting materials with varying absorbency and flow properties, and/or by selectively using adhesives or other bounding coatings on appropriate surfaces (or portions of surfaces) of the various layers to control the relative rate of liquid surface absorbency or liquid loss out of a layer vs. lateral spreading flow rate within that layer, or to control the time delay of flow to a detecting means as will be appreciated by those skilled in the art, particularly in view of the present specification.

The Releasable Electronic Coupling and Retention Portion

As shown in FIG. 2A, sensor 100 extends forward, inside a correspondingly-sized diaper, from a point somewhat below the back "rim" up and over the front rim, where the layer structure is different from the "in-diaper" portion previously described. A proximal end 340 of layer 300 extends beyond fold-line 342 (also shown in FIG. 3, FIG. 4 and FIG. 5A). As previously defined, this line indicates approximately where the sensor is to be folded over and affixed to the outside diaper portion 474. Once applied to portion 474, the sensor is designed to conveniently align with, connect to, and securely retain electronic monitor/alarm 500 (as shown in FIG. 2B). The unique attachment of the monitor unit by portion 450 ensures that, in the use environment, it is typically difficult (and therefore unlikely) for the monitor to be removed or have its operation compromised by the diaper-wearer. It is also designed, however, to facilitate easy removal of the monitor by a caregiver after the diaper is soiled, so it can be applied to the next diaper.

As illustrated in FIG. 5A, the proximal ends of conductive members 202 and 204, supported on portion 162 of layer 150 and tab 166 (and thereby comprising connector tab 170), are accessible where they extend past proximal end 340 of layer 300. At end 340, tab 170 preferably protrudes upward at an angle away from connecting and attaching layer 452 (shown in FIG. 3, FIG. 3C, FIG. 4, FIG. 5A, FIG. 5B and FIG. 7).

Layer 452 is made of thin, preferably impermeable material, and functions to connect layer 300 to monitor-retaining flap 460. This flap is essentially an extension of layer 300, which is provided for purposes of wrapping and retaining the monitor unit. Layer 452 is provided with top 454 and bottom 456 adhesive means. Bottom adhesive 456 is covered (before installation on a diaper) by the proximal part of removable strip 112 of protective packaging layer 110. (Layer 110 is not shown in FIG. 3 or FIG. 5A, but it is shown in FIG. 1 and FIG. 4.) Layer 452 can preferably be a double-sticky tape with a center core 453 of thin (approximately 0.001 to 0.003 inch thick) sheet paper or plastic like polyethylene, polyester or other suitable substrate material such as used for layer 300. The adhesive means can similarly include brushed, rolled or printed-on adhesives, heat melting, or ultrasonic, laser or other bonding processes to eliminate possible cost and other issues related to the use of pre-sticky tapes. Bottom adhesive 456 is provided to affix sensor 100 (and also indirectly, monitor unit 500) to portion 474 of a diaper. (This area is typically already plastic-coated on most brands of diapers for adhesion of the side-closure tapes, flaps or tabs, etc.)

Flap 460 is formed of a thin, preferably somewhat elastically stretchable, and transparent or translucent material. This combination of properties facilitates wrapping, and thereby retaining, monitor/alarm 500 on diaper portion 474, while permitting transmission of visual and/or audible alarm signals. Flap 460 is preferably made from clear, or translucent vinyl (about 0.001–0.003 inch thick), although other plastics like polyethylene or irradiated PVC (such as "shrink-wrap"), or even materials such as woven or non-woven natural or synthetic fabric could be used, provided the selected material has the necessary optical, acoustic and elastic properties, and is compatible with the adhesive means employed. In use, flap 460 is ultimately wrapped completely around monitor unit 500 from under its back side, over the front and top of the unit, and is then affixed to the exposed upper adhesive 304 of layer 300 (as can be inferred from FIG. 2B and FIG. 5A and is shown in FIG. 5B). Thus, flap 460 is adhered to layer 452, which is in turn adhered as an extension of impermeable layer 300 for affixing portion 450 to the outside front of a diaper (as previously mentioned). The location of layer 460, vis-à-vis impermeable layer 300 and connective/adhesive layer 452, can be adjusted to facilitate production assembly of the sensor, depending upon whether adhesive is selectively applied to components during the manufacturing process, or if pre-adhesive tape materials are used in conjunction with the application of a non-adhesive layer to create flap 460. Preferably, as shown in FIG. 3 and FIG. 4, the lengths of layers 300 and 460 are adjusted to allow tab portion 170 to protrude through a minimal gap in the otherwise end-to-end junction of these two layers. Disposing flap layer 460 between tab assembly 170 and layer 452 offers the additional advantage of shielding assembly 170 (and also the bottom of the monitor unit when installed) from layer 452's top adhesive 454. In alternate embodiments of the sensor, flap 460 can be fabricated as a continuous extension of layer 300, provided that layer 300 has the necessary properties, as previously mentioned. Also, upper and lower adhesives 304 and 306 of layer 300 would then need to be selectively applied from the distal end, to somewhat beyond fold line 342, so the flap end portion would not be sticky. If layer 300 and flap 460 are combined as the same continuous piece, a suitable opening 344 in layer 300, as shown at location "(344)" in FIG. 5A, can be punched to provide the necessary path to make connector tab portion 170 accessible for connection with monitor 500.

As shown in FIG. 5B, the most proximal end 462 of flap 460 preferably protrudes beyond the proximal (and non-sticky) end of layer 400 to serve as a small pull-tab portion 463 for releasing monitor/alarm 500 from sensor 100 when changing the diaper. The proximal end of layer 400 is fastened to upper adhesive 304 of layer 300, creating a smooth transition. The location and size of portion 463, vis-à-vis the preferably strong adhesive bonds that hold flap 460 to exposed top adhesive 304 of layer 300, and also that hold bottom adhesive 456 of layer 452 to diaper portion 474, ensure that tab 463 is, as mentioned previously, particularly awkward and difficult for a diaper-wearer to remove, yet is easily manageable by a caregiver. In various embodiments of sensor 100, either of lower 250 or upper 350 porous layers can also protrude proximally over fold line 342, to provide a more cushioned and comfortable edge (to the diaper-wearer), and to minimize bending stresses on the conductive layer 200. Any such protrusion should be slightly less than that of layer 400, so that the proximal edge of layer 400 is still fastened to upper adhesive 304 of layer 300.

A locating block 470 of foam or other light, rigid material (e.g., 0.125 inch thick urethane foam as shown in FIG. 5A and FIG. 9), corresponds in size to a mating "ridge-like" feature 520 on the bottom of monitor alarm 500 (as is shown in FIG. 18C and FIG. 20) Locating block 470 is optionally disposed on the surface of flap 460, where it is affixed by any suitable means such as adhesive, or by other means like solvent, ultrasonic or heat-bonding. The locating block can be provided with a notch 472, which allows connector tab portion 170 to more freely protrude from the rest of the sensor, and thus facilitates insertion of the tab portion by a caregiver into receiving portion 600 of monitor 500. Locating block 470 and mating feature 520 on the back of the monitor unit serve to keep the unit from sliding around on surface 474, and particularly from sliding out of the open sides of the loop created by wrapping retainer flap 460.

The above described locating features can also be replaced by other mating, interlocking, friction-increasing or relative movement-minimizing means. Such means can include a friction pad, or one or more short post-like or ridge-like, preferably rounded or tapered projections on the back surface of the monitor case. These projections can be designed to fit into suitable holes or openings through flap 460 and layer 452. Such projections can be more easily engaged with the sensor if they have tapered or rounded profiles. They can then easily be aligned with the openings and pressed slightly through the sensor into front surface 474 of the diaper. Such appropriately slight indentations are typically unnoticeable to the diaper-wearer. This alternative offers the advantages of eliminating the cost of locating block 470 and also of reducing the total installed height of the retained monitor on the front of a diaper (which is slightly increased by the thickness of the block). In use by a caregiver, the full insertion of connector tab assembly 170 into monitor 500 automatically aligns the monitor properly to be gently pressed down into or onto the provided locating features, as flap 460 is stretched around the monitor and affixed to the front of the diaper/sensor.

The functions of the locating features previously described can instead be served solely by the mating of sensor connector tab portion 170 with corresponding connector receiving portion 600 of monitor 500. In various embodiments, the proximal end of connector tab 170 can be designed to "bottom out" in the end of portion 600, rather than to remain "free-floating" as flap 460 is stretched over monitor 500 and adhered in place, thus locating and, vis-à-vis the flap portion, retaining the monitor on the front of the diaper. Particularly if tab 170 is the only locating feature employed, the side walls of receiving portion 600 must have sufficiently small clearance (preferably about 0.025" or less) with the edges of connector tab 170. Also, the tab must have enough rigidity to effectively stop the longitudinal movement of the monitor (when flap 460 is stretched over it)—as well as to locate and securely retain the monitor laterally. This is particularly practical if the nominal widths of the receiving portion 600 and the tab assembly 170 are made wide enough (such as about 0.75-inch, in the preferred embodiments shown). In such case where the connector tab also serves to solely locate and help retain the monitor unit, the receiving portion of the monitor case and/or the tab portion can preferably have tapering width, so that the sensor tab portion can be readily inserted into the monitor, yet guides itself into place with minimal side clearances as the tab is fully engaged. This arrangement, while eliminating the cost of the locating block, could tend to increase the scrubbing of the conductive elements 202 and 204 against contacts 620, 622 and 624 in the monitor unit receiving portion, due to greater relative movement of the monitor case and sensor tab in the use environment. Some such movement is likely advantageous for at least some choices of conductive elements 202 and 204. With metallic foil conductors, this would tend to promote increased self-cleaning of the contact surfaces. Such movement should be minimized, however, if more fragile printed-on conductive materials are used, to avoid possible loss of electrical contact. Printed conductive materials offer the potential advantage of allowing the contact spacing of layer 200 to easily be made wider only at the connector end, thereby eliminating the need for proximal-end narrowing 162 of double-sticky layer 150. (As previously mentioned, the narrowed portion 162 is employed in the embodiment shown in FIG. 3, to prevent adhesive exposure on either side of conductors 202 and 204 on the top of tab 170.)

As described, tab assembly 170 is designed to protrude either through or, in the preferred embodiment as shown in FIG. 5A, around end 340 of layer 300. This design serves to get conductive strips 202 and 204 from their flow-baffled, capillary-trap functional position (under layer 300 inside the diaper) through the substrate layer to the top side of the sensor portion outside the diaper for connection to the monitor. With this arrangement (as shown in FIG. 5B and FIG. 20), tab assembly 170 (with its conductive strips on top) can be simply inserted into monitor receiving portion 600, where it is pressed upward by a preferably removable spring clip/plate 610 (or other pressure-producing means) against fixed, smooth connector contacts in the monitor case. This simplifies the liquid-sealed connection of these contacts to electronic circuit 900 inside the monitor, and it also facilitates the ruggedness and cleanability of the monitor unit. As will be apparent to those skilled in the art, this arrangement is preferable to having monitor unit contacts address conductors on the outside of a tab assembly (i.e., facing away from the monitor). As previously discussed, alternate embodiments of the sensor could attach the conductive strips to (or make them part of) the bottom of layer 300 or 250, with either feed-through connections to the top surface (for contact pads on the top)—or a half-twist could be employed in layer 300 or other substrate, to get the front end of the strips on the top surface of a connector tab assembly. Any such alternatives would, however, likely increase cost and add other manufacturing and reliability problems. Another solution, with sensor configurations where the conductors exit the diaper on the back side of a contact tab assembly, is to have this assembly enter the monitor from the bottom, as will be further illustrated in the section, "Alternate Embodiments of Portion 450," later in the specification.

Stiffening tab 166 is preferably laminated on the bottom of the sandwich of layers comprising connector tab 170, so that the pressure-spring 610 or other means of the monitor connector slides smoothly and safely against this relatively hard, slippery surface, without risk of scratching or tearing the connector conductive strips (which may be very thin or simply printed-on). This feature also facilitates easy insertion of tab 170 into the monitor, as will be further described with reference to unit 500. On the top side of assembly 170, the contact strips are preferably separated from tab 166 by the top adhesive 154 and/or somewhat soft, compressible material of layer 150, as is shown in FIG. 20. This allows the contact areas of conductive strips 202 and 204 to "pocket" themselves or "cold-flow" over the smooth (preferably rounded) bumps or heads of contacts 620, 622 and 624 in the monitor unit, thereby increasing the reliability of the respective connections.

Alternate Embodiments of Portion 450

FIG. 22A shows an alternate embodiment of the monitoring system, wherein the sensor is incorporated directly into a diaper, and where connecting, locating, and retaining means 450 are implemented very similarly to the add-on embodiment of FIG. 2B. In this case, however, flap portion 460 (and/or optionally other layers like 300 or components such as tab assembly 170) emerge from within the top edge seam of the diaper layers (instead of being folded over from the inside surface) as shown at fold line 342. Just as in FIG. 2B, portion 450 continues down the front of the diaper under the monitor unit 500, in which area part of flap 460 is preferably adhered to diaper portion 474, or affixed by other means. The flap is then wrapped or stretched out and over the front of the monitor to be preferably adhered (by means of suitable strippable adhesive, or affixed by other means) to the top front sensor portion (or to the diaper itself, in still other embodiments where a diaper surface may be suitably exposed).

In the above, or other variations of portion 450, connector tab 170, and also optional locating features (such as block 470, not visible in FIG. 22A under the monitor and flap) position the monitor on the front surface of the diaper, while the somewhat elastic flap actually retains it. Elasticity in flap 460 is not absolutely necessary, as a shallow channel or flap-guiding ridges or other locating features can be added to the front or other surfaces of monitor 500 to prevent lateral slippage out the side of the flap. Elasticity, however, provides a smoother covering and more motion-tolerant, and hence secure, retention of the monitor. Moreover, additional projections disposed on the monitor could result in reduced cleanability and may be less comfortable to a wearer. An elastic flap also makes application of the monitor easier and more convenient for a caregiver. The flap is simply pulled over the monitor to quickly secure it to the diaper.

It is also possible, in various alternate embodiments of portion 450, for tab 170 or components to exit from the front of a diaper, instead of from the top front diaper seam. Such arrangement may prove desirable for manufacturing, but would appear relatively complex and possibly also prone to leakage. The alternative disposition of a diaper-monitoring unit on the back side of a diaper, while possible, is undesirable for ease of monitor attachment, caregiver convenience, and diaper-wearer comfort and health reasons, including those related to preferred sleeping positions. Various authorities recommend that, for prevention of S.I.D.S. ("sudden infant death syndrome") infants not be encouraged to sleep in a "face-down" position.

FIG. 22B, FIG. 22C and FIG. 22D show various alternate embodiments of connecting, locating and retaining means 450 that can be employed where the sensor is pre-incorporated directly into a diaper, and where flap-like front portion 460 is shorter than in FIG. 22A, because it does not wrap entirely around monitor/alarm 500 on the front of the diaper. Instead, locating block 470, which helps position the monitor, is separately disposed on the front of the diaper, and the flap wraps in a downward direction over the monitor unit, to retain it over the locating block. In order to avoid the tendency for tab 170 to be pulled out of the monitor by the action of stretching the retaining flap over the unit (as can occur with the arrangement shown in FIG. 22B, particularly if a locating block is not used), the sensor tab can preferably enter the monitor from the opposite, or bottom end, relative to the embodiments of FIG. 22A and FIG. 22B, as shown in FIG. 22C. Note, however, that in this case the proximal ends of conductive contacting elements 202 and 204 of tab 170 must be on the opposite (or bottom) side of the tab to mate with a different monitor configuration (shown in FIG. 21 A) wherein connector opening 600 is at the bottom of the monitor unit. This requirement for the conductive contacts to be on the bottom of tab 170 may be satisfied by the use of certain alternate sensor embodiments as previously discussed with reference to eliminating layer 150. Alternatively, it can be satisfied by a half-twist in the connector tab assembly or by other means, as will be apparent to those skilled in the art. An entirely different approach can employ an alternative "edge-clip" monitor connector embodiment as shown in FIG. 21B, so that strips 202 and 204 can be on the top side of tab 170, even with the connector assembly disposed on the bottom end of the monitor. Such monitor configuration would then be used in conjunction with the sensor shown in FIG. 22D, where the proximal end portion of tab 170 may preferably be bent to project relatively more sharply outward from portion 474. As will be appreciated by those skilled in the art, the above the methods illustrated in FIG. 22B, FIG. 22C and FIG. 22D, for the implementation of portion 450, can be applied in various combinations and also used with diaper add-on embodiments as well as incorporated ones.

FIG. 22E shows how, in embodiments where the sensor is built-in to a diaper, flap 460 and any monitor-locating features (other than tab 170) can be entirely separate from the rest of the added sensor components and can be either affixed to, or integrated with the front of the diaper as shown at 474. Such an alternate embodiment may well be most advantageous for manufacturing when the sensor is built-in to diapers, because it eliminates the complexity of getting tab 170 from the bottom through or between other layers of the sensor. Moreover, this method eliminates the need to join sensor-substrate layer 300 to flap 460 in the manufacturing process, thus facilitating the use of different materials (such as "double-sticky" tape for 300 but not 460) in separate continuous-strip processes, and/or simplifying the disposition of adhesives on only the appropriate portions of a single component. This approach (FIG. 22E) also avoids extending tab 170 as shown in FIG. 22C and FIG. 22D.

The embodiment shown in FIG. 22E also retains the most preferred "upward-wrapping" direction of flap 460 over the monitor unit, as shown in FIG. 2 and FIG. 22A, which arrangement offers the best caregiver visibility when attaching the monitor to a diaper/sensor, as well as making the removal of flap 460 (at the time of diaper changing) more convenient. As shown in FIG. 22E, only tab 170, as well as optionally a short extension of layer 300 and cover 400 (to provide a smoothly finished fold-line edge), need continue forward from the "in-diaper" sensing portion, to emerge from the top edge of the diaper (where they most easily exit the laminated diaper layers) to reach the front monitor location without creating a possible leakage path. Retaining flap 460 and optional locating block 470 can likely be more easily fabricated and affixed to (or integrated with) the front of the diaper if they are not part of the in-diaper portion of the sensor assembly. Flap 460 can thus be wrapped (preferably stretched) around unit 500, to then be adhered to the exposed adhesive on the proximal extension of layer 300 (or otherwise attached).

In any of the previously described embodiments of portion 450, suitable releasable attaching means (such as adhesive) can alternatively be disposed on the proximal portion of flap 460, near end 462, for the purpose of securing the flap after it is stretched over the monitor. In those cases where the flap wraps downward over the front of the monitor, adhesive can be used at the bottom of portion 474, as indicated on both flap 460 and the diaper in FIG. 22B, FIG. 22C and FIG. 22D. In any of these cases, a variation of strippable, top cover sheet 455 (as shown in FIG. 2A and FIG. 17) can protect the exposed adhesive prior to the attachment of monitor 500.

Monitor/Alarm Unit 500

As illustrated in FIG. 18A, FIG. 18B, FIG. 18C and FIG. 18D, monitor/alarm 500 includes a protective case 510 having an upper portion 512 and a lower portion 514. Lower portion 514 has raised ridge or collar portion 520 that serves as a receptacle for locating block 470. As was previously described with respect to sensor 100, various other forms of mating, interlocking or friction-producing features or materials could be employed in the sensor and/or monitor unit to accomplish the purpose of positioning and laterally retaining the monitor unit with respect to the surface of the disposable sensor and diaper. Lower portion 514 has a preferably recessed receiving portion 600. Together with spring clip/plate 610 and contact pins 620, 622 and 624, portion 600 helps provides monitor 500 with reliable electrical connection to the sensor, and also contributes to the proper location and secure retention of the monitor. Upper portion 512 provides a top, relatively smooth surface for the location of a faceplate overlay 517, which optionally includes design graphics 518 such as a "balloon" or other design. Overlay 517 comprises a functionally integral part of a mode change assembly 700, a visible signal transmission assembly 750, and an audible signal assembly 800. Upper and lower portions 512 and 514 each also provide their respective halves of a top 530, a bottom 532, a left side 534 and a right side 536 of case 510. Disposed within case 510 are a circuit board assembly 910 with a lithium coin-cell type battery (BTY), an audible transducer BPR (elsewhere referred to as 810), a visible display LED, a mode-change switch S1 and sensor-tab contacts 620, 622 and 624, altogether comprising the monitor/alarm portion of electronic circuit 900 as depicted in the block schematic diagram of FIG. 23. The upper and lower portions of case 510 are preferably joined to form a permanently-waterproof sealed case, which is designed to require no opening for repair or battery replacement during its intended useful life.

Sensor-Connector Receiving Portion 600

Receiving portion 600, as illustrated in FIG. 18B, FIG. 20 and FIG. 21A, receives tab 170, when inserted between a first 612, a second 614 and a third 616 set of prongs of spring clip/plate 610, and contact pins 620, 622 and 624, respectively. Contact pin 624 receives narrower conductive member 204. Contact pins 620 and 622 both receive wider conductive member 202, thereby completing the monitor circuit between pins 620 and 622. This action switches-on monitor 500 automatically, upon insertion of tab 170 (as will be further discussed with respect to monitor circuit 900). In a preferred embodiment (as shown in FIG. 20), there is provided a greater protrusion of contact pins 620 and 624, relative to center pin 622, from the upper surface of portion 600. The pressure of spring prong 614, in directly forcing the center of tab 170 against pin 622, acts in conjunction with the difference in protrusion of the contact pins, to gradually cause flexion of the resilient tab/conductive strip assembly as it is inserted. This arrangement thereby ensures the constant pressure of conductive strips 202 and 204, on tab 170, against each of the contact pins. This flexion of tab 170 also increase the frictional force by which the tab is retained in recess 600. A smooth rounded tip 619 of spring prong 614 preferably protrudes slightly (at an angle away from portion 600) beyond case top surface 530. Tab 170 is initially guided into place by tip 619, the edges 612 and 616 of plate 610, and also is centered and aligned by the sides of recess 600 in the monitor case.

In other words, to create a reliable connection for all monitor contacts, the preferably narrow cantilever spring prong 614 presses the axial mid-line of the tab directly against the center of three spaced contacts (or the top of the recess in the monitor case if only two sensing contacts are used). Because two outboard contact "bumps" 620 and 624 protrude relatively farther than does center contact bump 622 (or the monitor-case surface if only two contacts are used) the spring clip also causes the resilient contact tab itself to flex and act as a flat-spring element. This second spring force acts to securely press the conductive elements of the tab assembly against the outer contacts. (The relative protrusion of contacts could alternatively be reversed or mirrored, i.e., center-high and sides-low to achieve substantially the same purpose.) Because any subsequent relative motion of the connector tab and monitor simply "scrubs" the conductive strips over the smooth surface of the contact bumps while the contacting surfaces are under continuous pressure, self-cleaning and reliable electrical connection is assured.

With the preferred three-contact arrangement as described above, the monitor unit's operation is automatically turned-on (from a zero power-consumption state) at the same time and by the same means that connection is made between a disposable sensor and the reusable monitor unit—by simply inserting tab 170 into slot 600.

The retaining and contacting forces described above can optionally be made "field-adjustable" by the variable tightening of an attachment means 618 (preferably a screw), which can be employed to hold spring clip/plate 610 in place on lower portion 514 as shown in FIG. 18C. Whether adjustable or not, the use of a screw or other removable attachment of spring clip/plate 610 readily allows its replacement, should it become weakened or damaged. It also facilitates the occasional cleaning of recess 600 and its connector contacts, as may become necessary in the use environment, by making this otherwise enclosed area of the monitor readily accessible. Alternatively, spring clip/plate 610 can be slid into molded-in "dovetail" or other type slots in the monitor unit case and further located and retained by friction, or by a molded tab/detent or other means. Spring clip/plate 610 is preferably made of thin, corrosion-resistant sheet material (e.g. 0.015 inch thick, stainless steel or a likely thicker, suitable engineering polymer or composite).

Spring clip/plate 610 covers and thereby physically protects the contact area of the monitor, and also ensures that the connector tab of the sensor remains aligned with respect to the contact pins. The narrow (e.g., 0.125-inch wide), cantilever spring prong 614 preferably has no electrical function, but initially guides the tab as it is inserted into the slot between plate 610 and recess 600.

Tab 170 and mating slot recess 610/600 in the monitor unit are sized such that, when inserted, the end of the tab reaches lengthwise well past the contact bumps, but preferably does not reach the end of the slot (thus ensuring that the monitor unit will be positioned by locating block 470, or other locating feature, regardless of the exact end position of the tab). This arrangement (as previously mentioned with respect to sensor 100) minimizes the relative scrubbing of the sensor tab conductive elements against the connector pins which could otherwise compromise the electrical reliability of the connector during use. The width of slot 600 is only slightly wider (preferably about 0.050 inch) than connector tab 170, to ensure continuous alignment of the conductive strips and contact bumps, while still allowing easy insertion. The three entrance edges of slot recess 600 in the case are smoothly radiused, and the contact bumps are rounded and slightly countersunk into their respective locations in the monitor unit case. These features allow the connector tab a smooth ramping entry into the slot (without encountering edges of the contact bumps) as it is flexed by the spring and bumps. To make the initial engagement of tab 170 into slot 600 as easy as possible for a caregiver (and as previously mentioned), tip 619 protrudes a short distance beyond top edge 530 of the case, so as to automatically "catch" or capture the end of the tab into slot 610/600 as the monitor is applied to a sensor. Top edge 530 of the monitor case may preferably have contrasting marking or may be slightly recessed or ridged (as shown at 516 in FIG. 18A and FIG. 18B), to highlight (to a caregiver, viewing from above) exactly where tab 170 should be inserted. As previously described with reference to sensor 100, the material properties and order of the layers comprising tab 170 enhance both the ease of tab insertion/removal and also the contact-retention and reliability achieved by the connector means of the system.

The sensor-connection and monitor-retention means as described above employs fully liquid-sealed electrical connection directly through monitor case portion 514 at the bottom of recess 600 (and therethrough to an electronic circuit board assembly 910 inside), by contact bumps 620, 622 and 624. These bumps, in a preferred embodiment, are corrosion-resistant metal pins (e.g., stainless steel or gold or nickel plated brass) with smoothly rounded heads.

An alternative embodiment of receiving portion 600, shown in FIG. 26A, employs a preferably molded channel 600 in back case portion 514, the channel having three smooth-headed contact pins or bumps 620, 622 and 624, disposed on its surface, with a pair of smooth, preferably tapered or ramping protrusions 636 and 638, disposed on the opposing surface of a pressure-plate 605, which is preferably removable, but rigidly located in relation to channel 600. Plate 605 can be molded as a single piece of plastic and fixed in place by having beveled side edges that slide into dovetail slots in case portion 514 (such as shown at 617), or be held to case portion 514 by a screw, or by other means. Protrusions 636 and 638 are each disposed approximately between middle 622 and outer 620 and 624 contact pins, respectively, to form tab assembly 170 into a waveform, thus insuring contact with each of the contact pins and retention of the tab within the recess 600/605. Pressure plate 605 (with its protrusions 636 and 638) thus effectively replaces spring clip/plate 610 (of the previously described embodiment) and can preferably have a molded lead-in lip 606 to capture tab 170. Other embodiments include employing different contact members on alternate sides of recess 600 (such as having the equivalents of contacts 620, 622 and 624, but rather with them disposed alternately to address both top and bottom surfaces of a connector tab, such that a circuit therebetween is bridged upon insertion of the assembly for on/off operation without employing wider and narrower contact members, thereby reducing the width of the connector assembly), the attendant modifications of the sensor connection being apparent to those skilled in the art, in light of this specification.

The flexible-tab connector means of the elimination-absorber monitoring system is intended to provide high reliability in this demanding use environment with maximum caregiver convenience—at minimum cost. It may well find other uses, where low cost, high reliability, ruggedness, flexibility and convenience are paramount. For example, many products, systems and devices have need for making motion-tolerant electrical connections between a flexible-circuit element and some other element. The approach employed in monitor 500 eliminates much of the cost and other drawbacks of any add-on connector device which would otherwise need to be attached to a termination-end of a flex-circuit such as tab 170. A small, inexpensive plastic stiffener tab can be bonded to the back of a flex-circuit (e.g., 0.010-inch thick polyester in the case of tab stiffener 166 in sensor 100) to provide the desired contact pressure when used with a suitable spring clip or pressure-producing means. (Alternatively, with appropriate choices of material and dimensions, the flex-circuit substrate itself may be resilient enough for this purpose.) The conductive strips of the flex-circuit can be exposed a short distance back from end of the tab by selectively eliminating the top insulating lamination or coating of the flex-circuit in this region, where the conductive strips may optionally be plated or coated with a contact and reliability-enhancing material (such as gold). The whole connector system can easily be made water-resistant and is very simple to clean and maintain. It also has the major advantage of providing reliable, positive, automatic alignment—and extreme ease of repeated connection and disconnection.

The concept of this flex-circuit tab connector can easily be extended to multiple-circuit connections (i.e., more than two or three conductive circuits as used in diaper-monitor 500) by means of simply alternating the relative protrusion-height of the spaced contact bumps in the slot of the "female" part of the connector (such as slot 600 in case portion 532 of monitor 500). As in the two or three-circuit situations, the flexible, resilient, "male" tab which carries the flex-circuit conductors is then "rippled" slightly as it is inserted into the slot, where it assumes a slight "wavy" cross-section where it passes over, and springs against the multiplicity of contact bumps, as further explained below.

Further Discussion Of Alternate Connector Embodiments

As may be inferred from FIG. 26B, regardless of the number of conductors provided, pressure spring 610 of the connector employed in an elimination-absorber monitoring system or in other applications can alternatively be replaced entirely by a series of fixed (preferably molded-in) ramping protrusions or tapered-height pressure bumps (e.g., 636 and 638 shown) rising from the inside of a slot surface opposite to the surface with contact bumps (such as 630, 632 and 634 shown). One embodiment of such bumps can be visualized as lengthwise-bisected ice-cream cones lying on their sliced sides. These bumps are located such that each pressure-bump is spaced midway between an opposing pair of contact bumps (i.e., equally-spaced along their centerline) to gradually force the resilient connector tab into a lengthwise slightly wavy shape as it is inserted into the slot. These pressure bumps are tapered or ramped from zero-height (at the entry of the slot) to a their maximum height at the centerline of the contact bumps.

As shown in FIG. 26B, the contact bumps may themselves also be tapered in height, to minimize insertion force and to aid in deforming the tab. In this configuration (without a pressure spring), all the contact-maintaining force is supplied by the inherent resilience of the male connector tab itself. The surface of either or both the connector bumps and the pressure bumps may preferably be extended into a smooth angled lip 606 (on any of the opening edges of slot 600/605) to make capture and insertion of the male tab easier. With pressure bumps rising out of a (preferably molded) plate (instead of formed pressure spring and integral plate), the contact bumps need be the only conductive (and hence, likely the only metallic) portion of the entire female part of the connector. As previously mentioned, pressure plate 605 which covers recess 600 in the female portion of the connector can easily be made to slide into "dove-tail" slots, or be retained by use of one or more fasteners, detents or by any other appropriate means.

A "double sided" form of the connector can be made by changing the "pressure bumps" into conductive "contact bumps" and simply staggering the conductive strips of the flex-circuit tab (i.e., shift the pattern of strips on top and bottom of tab so they are perfectly "mis-registered" top-to-bottom). Either or both sets of connector bumps can be the ends of flex-circuits (or two halves of the same two-layer flex-circuit) leading out of the "female half of the connector. This makes it particularly easy to create "in-line" connections for various other applications, or to bring the connections into another circuit (board) assembly. It is also possible to employ an alternative method, where the conductive strips enter into the female connector to slide and ripple "sideways" over smooth contact bumps, but this has the disadvantage, for some applications, that momentary "wrong" connections can occur as the conductive strips approach their final (intended) registration with the contact bumps. It is also possible to create a "zero-insertion force" connector with either of the orientations by using a cam or other simple mechanical device to separate the contact bumps and pressure bumps (or contacts) for insertion of the connector tab, after which the process is reversed to "clamp" down on and deform the tab into a "wavy shape" as with the ramp-in method above.

The Control and Indication Interface

Monitor unit 500 utilizes a novel, simple control and indication interface with highly intuitive operating procedures. Diaper-monitoring units must be operable by very young baby-sitters, elderly or handicapped caregivers, and in general, any person that may at the time be acting under considerable stress or distraction in virtually any location or situation. For this reason, the present invention provides that the only required caregiver actions (for control purposes during operation of the elimination monitor) consist of "one-handedly" pressing a single switch (as described below with reference to a mode-change assembly 700) to both test and verify proper operation, and also to change alternately between the audible and visual alarm modes. Each pressing of the switch causes the unit to alternately emit either a momentary audible or visual alarm indication, but only if the unit is properly connected to the sensor and the system is ready to monitor a diaper. Each indication (either audible or visual) also clearly confirms the current mode (audible or visual) the monitor is set to operate in. The monitor unit operates continuously, in whichever mode it is set to, as long as a sensor is connected to it, thereby eliminating the possibility of it being accidentally left off or turned off. (The unit consumes no power when a sensor is not connected and conversely, connecting a sensor automatically switches the unit on.) As will be apparent to those skilled in the art, an alternate embodiment of monitor/alarm 500 could provide for both audible and visual alarms to be used together, with the likely consequence of increased power consumption.

The Mode-Change Assembly

Mode-change assembly 700, as shown in FIG. 18A and FIG. 21A, consists of a single waterproof, momentary-type flat-panel switch (S1 shown in the schematic diagram of FIG. 23), covered by a sealed faceplate overlay 517 on front case portion 512 of monitor unit 500 and is located near a lower corner of the faceplate to make it relatively less accessible to the diaper wearer than to a caregiver. The switch can be of any suitable type (such as the typical miniature dome-type keyboard switch which is used in the preferred embodiment) mounted on the top of the unit's circuit board, at such relative height and position that the end of its moveable push-button or other such activating button protrudes through a slightly larger hole 705 in the monitor unit front case portion 512. The switch button is nominally flush with the case top surface where it touches the bottom surface of flexible, waterproof, graphic overlay sheet 517, which seals hole 705. (In an alternate embodiment, an activating button protrusion can be molded into the top case surface along with a surrounding annular flexible feature for the purpose of reaching down to a relatively flat type switch below, either with or without the use of a separate flexible overlay.) Overlay 517 is somewhat smaller than the face surface of the monitor and is permanently (and preferably adhesively) affixed to a shallow locating recess in the front case portion 512 during its manufacture. This overlay is preferably a thin (typically 0.001–0.010 inch thick; 0.003 inch thick in the preferred embodiment) flexible rubber or plastic sheet such as vinyl, polyester, or polycarbonate (polyester is used in the preferred embodiment). The properties of the overlay must be selected to provide rugged protection of the switch in the use environment while still allowing the firm, targeted pressure of a caregiver's finger to conveniently and reliably actuate the switch. The pressure required can be preferably tailored by selection of the switch, adjustment of the case through-hole clearance or the end-gap (or preload force on the activating button) between the switch and overlay to make it relatively more difficult for a baby to actuate it. A graphic design on the overlay location (such as a "dot" 702, shown in FIG. 18A on overlay 517, directly over hole 705) can also provide indication of the switch's location—which would otherwise not be apparent—and can thus be made as obvious or not, as desired. The preferred position of the mode-change switch, when monitor 500 is installed on a diaper for use, is relatively inaccessible to the wearer, and can be made more so.

The top edge of hole 705 in the monitor case should be chamfered or rounded, so that repeated switch activation will not excessively stress overlay 517. The overlay is as thin as possible, consistent with the considerations discussed above, both to prevent flexure-induced fatigue failure, and also to avoid unnecessary attenuation of the audible alarm means of monitor 500 (which communicates via acoustic vibration through the same waterproof overlay). Mode-change switch S1 is connected, via the circuit board on which it is mounted, to the monitor units electronic circuitry wherein it actuates a suitable logic input to effect the changes between the monitor unit's audible and its visual alarm modes.

The Visible Signal Transmission Assembly

A visible signal transmission assembly 750, as shown in FIG. 18A, FIG. 21A, and FIG. 27, is designed to work in conjunction with flap 460 of sensor 100 in order to achieve sufficiently high brightness and useful viewing angle, with sufficiently low power consumption in the use environment. A high-efficiency, high-intensity LED (light-emitting diode) as shown in the schematic diagram of FIG. 23 is selected to be a "super high brightness" type, typically having a focusing lens with a relatively narrow "viewing" or beam "exit-angle" (such as a Mouser Electronics type 351-5200, a T-1¾ size red device having specified luminous intensity of 1,200–2,000 mcd at 10 mA, and a 20-degree exit-angle). Such devices having impressively high brightness, but narrow exit-angle output are readily available, but in typical applications they are very hard to see "off-axis", particularly in bright (or direct sunlight, or outdoor) ambient light. The LED is mounted inside monitor unit 500 at such position and relative height that it can project virtually all its light output through a hole 755 in monitor case front portion 512 and then through an aligned, relatively transparent window in any graphic design or other opacity of the unit's thin, adhesively-sealed permanent faceplate overlay 517 (as shown in FIG. 27). The through-hole in the case is provided with a chamfered edge 760 and is suitably dimensioned so that the emerging light cone or exit angle is not obstructed, but the unit's interior is otherwise shielded from view. The emerging focused light cone passes through the transparent window and then impinges on the bottom surface of the preferably translucent portion of sensor flap 460 which is designed to wrap over and to secure the monitor unit in place, while also acting as a light diffusing, rear-projection screen for the LED light cone. The described arrangement ensures that virtually all the LED chip's light output is efficiently transferred to, and suitably diffused over, the desired indicator area of the viewable outer flap surface of the sensor, and also results in practically 180 degrees of viewing angle when the monitor is in use. This arrangement also eliminates the need for any openings in, or accurate alignment of, the covering flap with the monitor unit to avoid obstructing the visual display. In an alternate embodiment, the monitor unit faceplate overlay may have light diffusing properties as well, thereby providing (when shining through the flap) additional angular diffusion or scattering of light, at the expense of some brightness. Faceplate overlay 517 may preferably have graphics integrated with the LED window such as balloon 518 or other attractive icon or design which can be seen through the sensor flap when the monitor unit is attached to diaper. Even if the sensor flap is a strong diffuser of light, the front panel overlay of the monitor unit is still clearly visible through it because the flap is stretched tightly over the unit, holding it in place. In use, the wearer's outer clothing can also act as a rear-projection screen for the LED, through which, rather surprisingly, the visual indications can be easily seen, even in relatively bright light (except in cases of thick, multi-layered, dense or dark-colored clothing materials).

The effective and convenient use of a diaper-monitoring system through clothing worn over the diaper is a significant advantage of the present invention over prior devices—and particularly over various non-electronic approaches that have all required that such clothing be repeatedly removed, and the outside of the diaper visually inspected—to determine when the sensor had been activated. The mode change assembly 700 of monitor unit 500 (as previously described) is easily operable, even "one-handed", through clothing. The unit's audible-mode indications can be easily heard from across a room, or even from a distant location via an ordinary remote baby monitor and, as explained above, both the audible and the silent visual-mode indications are effective through outer clothing.

The Audible Signal Transmission Assembly

An audible signal assembly 800 shown in FIG. 18A and FIG. 28, utilizes sealed faceplate overlay 517 of monitor unit 500 as a passive resonator membrane so that alarm signals (and particularly desirably low frequency ones) can be efficiently transmitted from a low-power, electro-acoustic transducer 810 ("BTY" in the schematic diagrams) to caregivers without compromising the waterproof seal of the unit's case (see FIG. 28). This overlay membrane is uniquely supported (but not normally touched) by features in the unit's case (disposed under the membrane) so that it is protected from damage due to excessive flexure, but its damping is not increased. Moreover, effective transmission of audible alerts through the sealed monitor case is accomplished at minimum cost and visual impact because no additional or noticeable, sealed, acoustically transmissive component is needed.

Prior electronic devices, and products of many kinds, have used audible transducers in conjunction with small openings in the respective units' cases to allow sound to emanate—and have thus not been capable of waterproof integrity. Other devices (particularly waterproof "alarm watches") have relied on conduction of sound through the unit case itself or through a relatively rigid component, such as a watch-face crystal, to address this problem. Because relatively rigid materials do not effectively conduct and then transmit to the air relatively low frequencies of acoustic or mechanical vibrations, this approach limits the usable sound frequencies to rather high pitches which are not desirable in many applications. For example, many people suffer from high frequency hearing loss that prevents them from effectively using such devices. Moreover, higher frequency audible alarm indications can be harder to notice over environmental background noise than are lower frequency sounds. If they are made loud enough—they can often become annoying in other circumstances. For years, engineers have employed the common prior-art strategy of simply (and often greatly) increasing the signal output power that drives an audible transducer, to overcome the rather severe attenuation of sealed electronic-device enclosures. Unfortunately, this practice has generally significantly limited battery life, by worsening what is inherently one of the most power-consumptive operating aspects of many devices.

In the present invention, a suitable transducer is selected from any of several types including (but not limited to) electromagnetic buzzers, piezoelectric beepers and loudspeakers. In the preferred embodiment, the transducer is selected to be a relatively small, very low power, electro-acoustic beeper with a desirably low resonant frequency of 2,048 Hz (such as an International Components type BRT-101). It is capable of producing sound pressure levels of about 80 dB(A) at 10 cm. range (in free air), while consuming less than 30 mW (rms) of power. This device itself incorporates a Helmholtz-type resonant enclosure with a small hole 820 at its top (approximately 0.125 inch in diameter). In typical electronic products, this hole is positioned behind, and in alignment with, a similar sized through-hole in the product's case. In the present invention, this transducer is driven by the monitor unit circuit which, at suitable times, produces "square-wave" signals having approximately 2.5–3.0 volt amplitude and having frequency approximately equal to the resonant frequency of the transducer (when sealed in the monitor unit's case).

In order to achieve the highest possible transfer-efficiency of acoustic energy from transducer device 810, through the sealed faceplate overlay membrane 517 of monitor unit 500, it is desirable to maximize a relatively undamped, free-flexing "drum head" area of the membrane, relative to its thickness. This is done by providing a relatively large but very shallow recess 830 in the monitor unit's case directly behind the acoustic "passive radiator" or drum head portion of the faceplate overlay (approximately 0.375-inch in diameter and 0.015 deep in the preferred embodiment). The bottom of this recess is preferably molded directly into the upper case section 512 and is perforated with one or more (but preferably a plurality of) openings 540 for relatively unobstructed acoustic transmission, but is still relatively rigid and strong in order to limit the maximum deflection of the membrane to just slightly more than its greatest amplitude when it is vibrated by acoustic compression waves from transducer device 810 inside the unit. This arrangement serves to prevent the overlay membrane from being pushed into the case during handling (or by "probing" on the part of a child or infant) and thus acts to prevent its damage, by limiting the deflection of the overlay material to well within its elastic range. Because the overlay seamlessly covers the recess, the location of the recess can be made visually unnoticeable, further reducing the likelihood of damage to the membrane.

In variations of the preferred embodiment shown in FIG. 28 with overlay 517 having uniform overlay cross-section, the overlay may instead be laminated from two or more layers so that the acoustically-active portion lying above the shallow recess (as described above) can be thinner than other areas of the overlay, thus providing an optimal balance of durability and sound transmission. Similarly, as described previously, part or parts of the overlay can be relatively transparent for visual display purposes, or have other desirable properties where switches or other devices are located under the overlay.

The enclosure of a transducer device into a relatively small sealed volume, as in the present invention, inherently raises the resonant frequency of the transducer. This fact necessitates that the driving signal have appropriately adjusted frequency for maximum acoustic volume. A transducer's own enclosure (if used) is generally tuned for maximum transfer of acoustic energy to the relatively "infinite" volume of a room or outdoors. In the case of the present invention, however, the case design of the monitor may be modified to provide additionally optimized acoustic impedance matching (i.e., coupling) to the overlay membrane. The transducer device or its own resonant enclosure may also be suitably modified to achieve the same purposes as will be readily apparent to those skilled in the art. Moreover, the monitor case can be partially evacuated of air, and/or filled with a suitable gas to reduce the cavity resonant frequency or the acoustic damping produced by the small internal volume of the case to enhance the efficiency of acoustic transfer. The partial evacuation or filling of the monitor unit case with relatively inert gas can also be used either with or without solid or jell-type potting or conformal coating to prevent deterioration of the monitor's internal components due to corrosion or other chemical effects.

Other Applications of the Audible 800 and Visible 750 Signal Transmission Means It will be apparent to those skilled in the relevant arts that the basic elements of both this invention's audible and visible signal assemblies are also applicable to other diverse applications using non-audible or non-visible wavelengths (such as ultrasonic/infrasonic or infrared/ultraviolet waves, respectively). It will also be apparent that these methods are symmetrically applicable to situations wherein the respective transducer is either alternatively or additionally a detector of the signals, with a given "acceptance-angle" instead of purely a source with a given "exit-angle". Most, if not all the respective advantages cited for these methods clearly apply to such other applications.

The Electronic Methods Employed by Monitor 500

As illustrated in FIG. 23, the monitor/alarm circuitry 900 preferably employs narrow, relatively fast transition-time pulses generated by an oscillator circuit for conductivity measurement, instead of either the DC or sinusoidal AC methods employed by previous systems. The pulses can have a duration of about 0.1 second and a repetition rate of about one pulse every 3 seconds. This rate is chosen as a compromise between the "see-it-at-one-glance" user preference (as determined by subjective testing with selected caregivers who typically did not like to wait more than 3-seconds while watching for an alarm flash to occur) and excessive power consumption caused by more frequent alarm indications (assuming that the same pulse widths and repetition rates are used for both sensing and alarm indication). Alternatively, as discussed below, the pulses can preferably be doubled, i.e., each burst comprising two pulses, each having a duration of about 0.1 second, separated by about 0.1 second off-time and such bursts occurring about every 3 seconds. This relatively low duty-cycle offers the advantage of allowing the ions in the matter being monitored to recover their normal, random distribution between pulses, so that the average measured conductivity does not radically change over time. As may be appreciated by those skilled in the electronics art, different embodiments of monitor circuit 900 could instead apply pulses to the sensor that alternate in polarity, or the pulses could be applied through (i.e., in series with) a capacitor to achieve a true zero time-average of applied voltage. Such alternative methods are, however, more component-intensive and complicate, if not preclude, the integral automatic power-switching via connection of sensor 100. The high-frequency harmonic-content of the pulse waveform, due to the fast transition-time of the pulses, also exploits a phenomenon commonly referred to as "skin conductivity" of solids, whereby relatively higher frequency electrical signals often travel much more easily over the surface of solids and semi-solids than do lower-frequency or DC signals. This phenomena is particularly useful for reliable feces-sensing. Moreover, digital switching in the oscillator circuit that generates the pulses is much more energy efficient than can be achieved with AC sinusoidal oscillators, resulting in longer battery life for monitor/alarm 500.

The same pulse widths that are generated for sensing are, in one preferred embodiment (as shown in the schematic diagram FIG. 23), also used for the beeps or flashes produced by the monitor unit to indicate the "diaper needs changing" state, permitting the combination of electronic functions and facilitating further energy savings. In various microcontroller-based embodiments (as shown in FIG. 24A, FIG. 24B, FIG. 24C and FIG. 24D), it is alternatively feasible to have different pulse widths and/or repetition rates for sensing as are used for alarm indications, without increasing the component count. Such an embodiment can use very narrow pulses for sensing (typically a few milliseconds wide) to minimize both power consumption and ionic dissociation. As mentioned previously, in order to optimize the observability of the alarm signals (particularly in the face of competing background noise or ambient light) it is preferred to use double (or multiple) pulses rather than single pulses for alarm indication. Alternatively, other types of audible and visual signals can be employed, such as musical tunes, simulated animal noises or other sounds, as well as voice or displayed messages. Such alternatives, however, are likely to result in more complex circuitry, increased power consumption and potentially greater size and weight.

Preferred Discrete-Logic Embodiment of Electronic Circuit 900

Referring to the electronic circuit diagram (FIG. 23) of a preferred discrete-logic implementation of monitor unit 500 and connected disposable sensor 100, a combination of CMOS logic gates (such as the 4000-series or 74HC-series devices) and other standard components provides all the necessary electronic functions. Several functional blocks which can be implemented using common methods are shown simplified for clarity. For example, a low-frequency CMOS "double-pulse oscillator" block (U7) generates a continuous waveform, as shown, whenever the unit is connected to a disposable sensor, thereby providing the primary timebase and conductivity-measurement pulses for the monitor circuit as well as pulses for audible or visual alarm activation. As will be readily apparent to those skilled in the electronics art, this type of oscillator block can be implemented using a number of common techniques, including simple R/C relaxation oscillator configurations with suitable standard gates. Although various types of crystal or ceramic resonator oscillators could alternatively be used, timing accuracy greater than about +−10% is not necessary in this application and the simple R/C oscillator approach is generally the most economical. Typical CMOS gates with negligible output loading provide output swings essentially from 0-V to +V as well as having relatively fast switching transition times in the microsecond range or faster, which are desirable both for power minimization and for effective measurement of feces-related conductivity.

The double pulses produced by U7 are applied through sensing reference resistor R2 (preferably about 2 megOhm in a preferred embodiment) to sensor-connector SC1 (same as contact pin 624) and thereby to conductive strip 204 of disposable sensor 100. As shown in FIG. 20, this conductive strip is, in the preferred embodiment, the narrower of the two strips 202 and 204 running along sensor connector tab 170 and leading to "capillary trap" measurement gap portion 160 of sensor 100 inside a diaper. Upon insertion of tab 170 of the sensor into receiving portion 600 of monitor unit 500, both these strips are connected to the monitor circuit 900 as shown by the dashed lines in FIG. 23, with wider conductive strip 202 bridging sensor-connector contacts SC2 and SC3 so as to connect the anode (in this embodiment) of the monitor's internal lithium "coin-cell" battery BTY to the 3-Volt "+V" supply bus of the circuit, and thus serving as the circuit's only power on/off switch. This advantageous arrangement, by which one "end" of the conductivity measuring circuit is common to the power supply bus of entire circuit 900, allows just one "extra" (third) contact SC3 (which can be either 620 or 622) in the monitor connector to provide (in conjunction with wider conductive strip 202) fully automatic master on/off control of the system. It is important that the voltage applied to SC1 and thereby to conductive strip 204 of the sensor is essentially equal to the constant +V (battery voltage) applied to SC2 and SC3 (and thus conductive strip 202) during all but the relatively brief (approximately 0.1-second) low-going pulses from U7 (occurring about every 3 seconds). As previously described, this low duty-cycle of applied voltage across the sensor minimizes ionic dissociation of the material to be sensed as well as the power consumption of the circuit due to current conduction through the sensor. As also previously described, the relatively fast transition-times of the pulses exploit the advantageous high-frequency skin-conductivity effect.

The low-going pulses from U7 are inverted by UB and then applied to one input of AND gate U9. The other (preferably Schmitt trigger type) input of U9 is connected through a protective current-limiting resistor R3 (about 100 k-Ohms) to the sensor via sensor connector SC1, which is, in a preferred embodiment, the same as contact pin 624 of monitor 500. Resistor R3 and transient absorption devices Z1 and Z2 are used to protect the monitor circuitry from possible electrostatic-discharge (ESD) events during handling of the monitor unit or during operation in the use environment. Z1 and Z2 can be any suitable zener diode or other preferably fast response, high current semiconductor transient suppression device (such as General Instrument SA10A "Tranzorb" devices) with a rated breakdown voltage of about 10-Volts. These devices must also have maximum room-temperature reverse leakage below about 1 uAmp at +V (3-Volts). Capacitor C1 is preferably a 0.1-uF stacked-film type transient bypass device connected across the +V bus and circuit Common (−V). Because the CMOS devices in the monitor circuit are all lightly loaded, relative to the equivalent series resistance of lithium cell BTY, a single small power supply bypass capacitor is all that is necessary for the entire circuit. Neither the type, or value of C1 is particularly critical, but it should have good high frequency characteristics and low leakage (preferably well below 1 uAmp at +V).

The effective electrical impedance of disposable sensor 100 (RSNSR in parallel with CSNSR, connected between SC1 and SC2) acts, in conjunction with reference resistor R2, to divide the voltage pulses applied to one (preferably Schmitt-type) input of U9, such that the output of U9 will go high only during U7's relatively brief double output pulses, and only at such times that the sensor impedance falls from its initial value (typically at least several megOhms), to below about 500 kOhms due to the presence of either urine or feces bridging the conductive elements of the sensor within its capillary trap, as previously described. The simple "over-threshold" voltage determination of the "triggered" condition of the sensor by use of a Schmitt-trigger gate input of U9 is made feasible by the decisive, and relatively long-lived conductivity-change produced by the structure of sensor 100 in response to either urine acting on the elimination-absorber, or due to the presence of fecal matter, as detected by monitor 500 with low duty-cycle, fast transition-time pulses. The lack of any requirement for relatively more power-consumptive and expensive precision comparator devices, as well as for any electronic latching function in the detection circuitry, are significant advantages of the elimination-absorber monitoring system.

The hysteresis effect provided by the typical CMOS Schmitt-trigger input gate employed for U9 desirably prevents excessive current drain due to linear-region biasing of the gate, which would otherwise be produced by slowly-changing sensor conductivity. This hysteresis also prevents unstable or intermittent alarm activation when the sensor is marginally "triggered". As will be apparent to those skilled in the art, the illustrated Schmitt-trigger input configuration of U9 (simplified for clarity) is not actually available as a single standard part, but the preferred Schmitt-trigger input capability can be readily provided by use of a separate Schmitt-type inverter (such as the 74HC14) in series with a standard AND gate (such as the 74HC08) or instead, the output of a standard Schmitt NAND (such as the 74HC 132) can be inverted to accomplish the same purpose. In fact, additional gate-delay in the sensor input (through R3) to U9 is desirable to ensure that narrow (and energy wasting) output "glitches" are not generated by U9 synchronous with the leading edge of each high-going input pulse arriving from U8, during the time periods when the sensor is being monitored, but is not yet triggered. This "gate-delay" method is more efficient than the alternative of inserting an additional delay capacitor (connected to a supply rail) at the R3 input to U9.

In addition to acting as the detection threshold reference, resistor R2 also serves to limit the absolute maximum possible (short-circuit) current across SC1 and SC2/SC3 to about 1.5 uA during sensing pulses (and zero otherwise). R2, in conjunction with the rest of the low duty-cycle sensing pulse circuitry, also severely minimizes discharge of the battery (which is sealed inside the monitor) in the unlikely event that all three of the unit's sensor-connector pins 620, 622 and 624, are somehow shorted together, even for lengthy periods. Because of the single-cell battery's relatively high equivalent series resistance and low (approximately 3 Volt) output, the monitor circuit pose no potential for harm to users even if it were hypothetically applied directly across exposed wet skin bridging the connector contacts after a (worst-case) hypothetical short-circuit failure had somehow previously bridged Z2 and C1.

At any time that the attached sensor has become "triggered" as described above, the output of AND gate U9 continually produces short, double, positive-going pulses that are approximately the logical complement of the original output of U7. These pulses are applied through a combination of steering-logic gates U3,U4,U10 and U11 to activate either an audible or a visible alarm, depending on the existing output state of "toggle flip-flop" U1. As shown in FIG. 23, when the sensor is "triggered" and output Q of U1 is high, the double pulses from U9 are allowed by OR gate U3 and AND gate U4 to enable U5 (a simple CMOS-gate R/C relaxation oscillator, shown as the box labeled "U5 BEEPER OSC" in FIG. 23), which generates a suitable "square-wave" output only during the duration of the double enabling pulses to drive a low-power electro-acoustic beeper BPR (i.e., transducer 810 of monitor unit 500) at near its resonant frequency (preferably approximately 2 kHz) thereby producing a "double-beep", which preferably repeats approximately every 3 seconds. As will be apparent to those skilled in the electronic art, BEEPER OSC U5 can be implemented in a number of common ways, and it is also possible for U5 to be directly powered by the output of U4 instead of enabled by it. The use of a separate oscillator which remains either quiescent or is alternatively powered-off except during the brief alarm pulses is important to conserve battery energy. Transducer BPR (same as transducer 810 in a preferred embodiment) can be any suitable piezoelectric or electromechanical transducer, preferably with average drive current requirements in the 10 mA range at 1.5 to 3-Volts, and sound output level of about 80 dB(A) at 10 cm (such as the transducer previously described with respect to audible signal assembly 800). Similarly, when the sensor is "triggered" and output Q of U1 is alternatively low, the double pulses from U9 are allowed by OR gate U10 and AND gate U11 to turn-on (i.e., double flash) visible alarm device LED at current level of about 5–10 mA. The LED can be any high-brightness, low current type as previously described with respect to visual signal assembly 750.

As described above, the state of toggle flip-flop U1 controls which alarm mode (audible or visible) is activated after the attached sensor is triggered. U1 can be toggled by user operation of mode switch S1 (as previously described with respect to the mode change assembly 700), which acts to pull the "T" input of U1 logically high from the normally low state maintained by pull-down resistor R1 (approximately 100 kOhms) which is connected to circuit common (−V). This toggling of U1 can only occur, however, while the monitor circuit is switched on by the proper insertion of connector tab assembly 170 of sensor 100 into monitor 500. As previously described, the properly inserted sensor switches power to the monitor circuit by connecting contact 620 to contact 622 through the wider (202) of the sensor's two conductive strips 202 and 204. At any time that MODE SWITCH S1 is activated (while the monitor unit is properly connected to a sensor) and U1 is thereby toggled, either of ONE-SHOTs U2 or U6 is alternatively triggered. If output Q of U1 is asserted, this in turn activates ONE-SHOT U2 (which, like U6, can be any suitable standard low power monostable circuit). U2 then produces a brief (approximately 0.2 second) output pulse. This pulse then causes a similarly brief audible "BEEP" of transducer BPR by enabling BEEPER OSC U5 through gates U3 and U4. If alternatively, output Q-bar of U1 is asserted, visible alarm device LED is instead similarly activated via ONE-SHOT U6 and gates U10 and U11. Typical CMOS gates, as shown in FIG. 23, are capable of driving either of the alarm devices directly up to currents of a few milliamps. As will be appreciated by those skilled in the electronics art, either BPR or LED can optionally have suitable current-limiting resistors connected in series with these devices, to alter the trade-off between power consumption during alarm activation and either volume or brightness, respectively.

As previously discussed, a truly convenient and reliable elimination-absorber monitoring system must have user interface and operating sequences that are exceptionally simple and intuitive. The present invention achieves this objective by means of its single mode switch and coupled alarm devices circuit combined with the automatic power switching of the system as described above, to provide all necessary operator interface functions for the monitoring system—including both the convenient changeover from audible to visible alarm mode, as well as the inherent and unmistakable demonstration of which mode is currently selected. Activation of the mode switch also clearly verifies the proper connection of a disposable sensor to the monitor unit. As will be appreciated by those skilled in the electronics art, at the expense of likely greater complexity, cost and energy consumption, additional circuitry could easily be provided to expand the scope of the self-test function that is initiated by connection of a sensor and subsequent activation of the mode switch to test any other aspects of the monitor circuitry and/or the connected sensor, while still using the same alarm devices to indicate a "ready" or "OK" status. It is similarly possible to link the initiation of any other useful indications such as the time of day, etc., or even purely amusing sounds, etc. to activation of the mode switch by simply cascading these various events into a sequence and/or by employing additional indication devices. Those skilled in the electronics art will also recognize that numerous alternative arrangements or choices of oscillator types, logic chips and/or combinations of discrete components (including one or more custom or semi-custom integrated circuits) could possibly be used to implement various embodiments of the present invention without departing from this invention's basic elements and methods.

Microcontroller-Based Alternate Embodiments of Circuit 900

As examples of alternative embodiments of monitor circuit 900, FIG. 24A, FIG. 24B, FIG. 24C and FIG. 24D show four variations of alternative programmable microcontroller-based embodiments. As is well known by those involved with the electronics industry, several families of "low-end" CMOS microcontroller chips (such as a Microchip Technology PIC12CXX device shown in these diagrams), having various attractive specifications and capabilities, are available from a number of manufacturers at relatively low cost. The use of a microcontroller chip, instead of the discrete logic of FIG. 23, offers the advantage of lower component-count on the monitor unit's circuit board and as a result, also likely lower assembly cost. A microcontroller-based embodiment may also minimize the range of observed variations in the time-based functions of the monitor system from unit to unit, by reducing the number of separate resistor/capacitor time-constant combinations needed, although this is not really a critical issue, given the low timing precision required (probably no better than about +/−10%, in general). Another possible advantage would be the relative ease of changing timing values or other aspects of the monitor system's operation, if desired, by revising the firmware programmed into the microcontroller chip—instead of by changing component values or other hardware. Also, the different functions can easily have separate timing constants without incurring the overhead of additional hardware (such as durations used for sensor-pulsing vs. alarm indication, or audible vs. visual alarm indication).

FIG. 24A shows an alternate embodiment of the present invention wherein a PIC 12Cxx microcontroller U1-24A executes programmable code (i.e., firmware) as represented by the flow-chart shown in FIG. 25. Only a single oscillator is needed, because the PIC microcontroller has an internal clock oscillator whose frequency is determined by external R/C components R4-24A and C2-24A which can clock the microcontroller continuously while a sensor is connected to switch-on power. With suitable timing provided by either firmware or on-chip timer delays, the microcontroller chip runs a continuous "monitor loop" as shown in the flow chart during which it repeatedly polls (and debounces) mode switch S1 (approximately every 0.1-second), pulses and monitors the connected sensor 100 (about every 3 seconds), and also generates, when appropriate, suitable alarm signals to drive BPR and LED—in effect approximately emulating the functions of the discrete embodiment of FIG. 23. Note that the user interface, the control sequences and sensing methods, the automatic power switching of battery BTY via sensor connections SC2 and SC3 (contact pins 620/624), and the ESD protection and bypass configurations are all essentially the same as in the discrete logic embodiment of FIG. 23. Also note that microcontroller U1-24A even has a Schmitt-trigger input line 12 connected to the same resistor network for the sensing portion of the circuit, as described in the discrete logic embodiment. A significant difference in this embodiment (as compared to the previous discrete logic version of FIG. 23) is that here the sensor can, without extra hardware, be advantageously pulsed with much narrower, single pulses (approximately 10- milliseconds long) as opposed to the double 0.1-second pulses or single 0.2-second pulses that are used for alarm or mode-change indications, respectively. As will be appreciated by those skilled in the electronics and firmware programming arts, numerous alternative arrangements or choices of oscillator type, microcontroller chip and configuration of I/O (i.e., input/output) lines as well as various firmware implementations could possibly be used to produce various embodiments of the present invention without departing from this invention's basic elements and unique combination of methods.

On the other hand, likely disadvantages of a microcontroller-based embodiment of monitor circuit 900, relative to the discrete-logic version of FIG. 23, include dependence on a sole-sourced key component (the microcontroller chip itself), possible increased susceptibility to improper operation due to electrical noise or interference, and relatively greater energy consumption. As will be appreciated by those skilled in the art, noise and interference susceptibility can be a problem with microcontroller-based systems in general, usually due to unintended resetting of data stored in RAM (random access memory) registers.

Such an event is particularly troublesome if the data corrupted is critical to functions of the system, and most especially so if program flow is altered due to corruption of the microcontroller's program-instruction counter (which causes unexpected and possibly unacceptable "jumps" in program execution). So-called "watchdog timers" are commonly used to automatically reset the program counter in case of such gross occurrences where the program execution has "hung up" for more than a certain period of time (the PIC microcontroller chips shown in FIG. 24A, FIG. 24B, FIG. 24C, and FIG. 24D, each have a built-in watchdog timer that could optionally be used for this purpose), but this alternative comes with the expense of added power consumption to continuously run the watchdog oscillator and counter.

Relatively increased power consumption by a microcontroller-based embodiment or the present invention stems mainly from the otherwise core advantage of programmed logic in general, i.e., the substitution of program-code execution by the microcontroller for dedicated hardware. Microcontrollers typically require several clock cycles to accomplish the execution of a single program instruction, and they must therefore have a clock frequency several times higher than the highest repetition rate of any output signal to be generated by execution of firmware. This means that if, in the pursuit of minimum component-count, a microcontroller is employed to generate a 2-kHz square wave signal to drive the audible alarm device of the present invention (as shown in FIG. 24A) the input clock frequency for the microcontroller (in this case) would have to be at least 16 kHz. Because total power consumption in CMOS logic is nearly proportional to clock frequency, this arrangement is considerably more energy-expensive than using a 2-kHz oscillator. Also, generation of a continuous 2-kHz square wave for approximately 0.1-second long takes many (hundreds in this case) bytes of instruction code if the microcontroller cycle-time is so slow as to need fully linear coding (where an output line is turned ON/OFF/ON/OFF.. etc., with successive instructions continuously executed for 0.1-second).

For the above reason, the circuit of FIG. 24A can be modified into the version shown in FIG. 24B, wherein the pulses from a 2-KH oscillator OSC are used to clock a PIC 12Cxx microcontroller U1-24B, and are also gated (using an additional logic chip U2-24B under firmware control via an output line O1 of microcontroller U1-24B) directly to audible alarm transducer BPR. With this circuit, the microcontroller can now be clocked at the same 2-kHz frequency used for alarm signals. Although this arrangement is more energy conservative than that of FIG. 24A, it still requires the microcontroller to be clocked at 2-kHz—a considerably faster rate than is needed to accomplish any of the monitor unit's other functions via the execution of firmware.

FIG. 24C shows another variation of a microcontroller-based monitor embodiment where a separate hardware 2-KHz oscillator OSC (similar to U5 BEEPER OSC as used in the discrete embodiment of FIG. 23) is employed and where a PIC 12Cxx microcontroller U1-24C is clocked at the minimum rate (approximately 128 Hz) needed for it to accomplish all needed functions (without use of interrupt-driven code) other than direct audible tone generation. As will be apparent to those skilled in the art, it is alternatively possible in designs with various available microcontroller chips for a relatively slow clock oscillator (operating at 128 Hz, for example) to be combined with a frequency divider to periodically "wake-up" the microcontroller from a relatively lower-current "sleep" mode by resetting it each time it wakes up (every 3-seconds, for example), thereby combining, in the context of the present invention, the features of even lower average frequency clocking with repetitive resets which can effect recovery from "hang-up" events without the current consumption drawback of a dedicated watchdog timer. With this approach, the input employed to monitor mode switch S1 would have to be configured to wake up the microcontroller from "sleep" directly upon operation of the switch instead of the switch input being polled by the microcontroller only every 3-seconds (during each wake-up period), in order to provide adequately fast switch response time, even if the switch is momentarily operated while the microcontroller happens to be "asleep".

Finally, FIG. 24D shows a compromise variation of monitor circuit 900 where a PIC 12Cxx microcontroller U1-24D has its clock oscillator frequency dynamically changeable under firmware control, from a 128-Hz rate needed for most of the monitor's functions to a 16-kHz rate necessary for direct audible alarm drive at 2-kHz. This is done by using the corresponding output line O4-24D, of microcontroller U1-24D, that pulses the sensor—to also simultaneously increase the charging current available to the microcontroller's internal relaxation oscillator through additional resistor R5-24D (and thereby to increase the frequency of oscillation for short bursts, when needed). Also added, in this embodiment, is the blocking-diode D1-24D (any low-leakage type such as a 1N4151), which eliminates reverse current flow when the output line is returned to the low condition, causing the clock frequency to return to the 128-Hz rate. Although any alternative microcontroller chip and/or available output line could be used for the purpose of clock frequency changing, because the inexpensive PIC chip shown is packaged as an 8-pin device, there is no separate I/O line available. This means that the microcontroller must run at 16-kHz throughout the duration of each sensing pulse, but the sensing pulses can be easily made much shorter than the 0.1-sec used in the discrete embodiment of FIG. 23, because the microcontroller does not need additional hardware to provide suitably longer pulses (after the sensor has been triggered) for alarm indications. Pulses can be produced by the microcontroller with minimum duration equal to four clock periods (a single instruction time) without additional hardware. Thus, the "pre-triggered" sensing pulses (and hence the pre-triggered periods of relatively higher current operation can be less than one millisecond long, to both conserve energy and reduce the ionic-dissociation effect (previously described). Also, as shown in FIG. 24D, in order to allow the sensor-pulsing output line of microcontroller U1-24D to have the correct logic sense (i.e., go "high" when asserted), for appropriately accelerating the clock oscillator, the power-switching sensor contacts SC2 and SC3 are connected so as to switch the common end (i.e., –V) of battery BTY-24D instead of the +V end as in the previously described circuit 900 embodiments (FIG. 23 and FIG. 24A, FIG. 24B, and FIG. 24C). This arrangement ensures that zero voltage is applied across the sensor, except during the low duty-cycle sensing pulses, and also that the fast transition-time of the pulses can exploit the high-frequency signal propagation characteristics of the material to be sensed, just as in the previous embodiments as described.

System Energy Requirements And Battery Life

A key requirement for a practical elimination-absorber monitoring system is that it be capable of continuous use for the entire diaper-wearing portion (typically the first 2 years) of a baby's life, without need for either battery changing or recharging. Based on many laboratory measurements, the electronic circuit using the methods and control strategies of the present invention, as shown in FIG. 23, typically operates at such low total energy consumption, that two full years of continuous operation (after extended storage) can be confidently expected with the system's single 560 mA-Hour, 3 Volt lithium coin cell BTY unit (such as a Panasonic CR2354). Cell BTY is intended to be permanently sealed into monitor unit 500 during the manufacturing process. The maximum electrical current requirements and resulting battery life are calculated as follows by using the relationship:

Average Current=(Instantaneous Current)×(Duty-Cycle).

Adding the components of average current for the three operating states of the monitor system:

Pre-Trigger Current+Mode-Changing and Self-test Current+Post-Trigger Current=Total Average Current, where:

Pre-Trigger Current (includes periodic sensor-pulsing)=4.0 uA;

Mode-Changing and Self-Test Current (includes alarm device drive current and assumes that there are an average of 20 Mode-Changes per day over the useful life of the monitor unit, and that each Mode-Change is indicated by a 0.2-second alarm-device beep or flash), Alarm-On Current×Mode-Changes×Alarm Pulse Time 8.0 mA×(20 events/24-Hrs)×(0.20-sec)×(1-Hr/3,600-sec)=0.4 uA and Post-trigger Current (includes alarm device drive current and assumes that there are an average of 5 diaper-changes per day over the useful life of the monitor unit, and that each alarm continues for an average of 12-minutes before each soiled diaper/sensor is changed and the alarm stops, and that the alarm indications consist 1 of two 0.1-second beeps or flashes every 3.0-second, and also that virtually no offtime occurs between changes), Alarm-On Current×Alarm Events×Alarm Pulse Time 8.0 mA×(5 alarms×0.20-Hr/24-Hrs)×(0.20-sec/3.0-sec)=22.2 uA To yield a Total Average Current=26.6 uA Assuming that, for the lithium cell employed, voltage remains essentially constant for the useful life of the cell (the most stringent assumption for calculating Battery Life), Battery Life=Cell Capacity/Total Average Current=560 mA-hrs/ 26.6 uA×(1-Year/8,760 Hours)=2.40 Years The above calculated Battery Life is preferably adjusted downward by a 15% factor to compensate for possible high-temperature storage prior to normal use and for variations in individual battery performance, and also to include a miscellaneous safety factor. With this adjustment, monitor unit 500 of the present invention has a calculated net continuous operating life: 0.85×2.40 Years=2.04 Years Note: In actuality, all the current consumption values shown above are functions of operating voltage (+V), which can be expected to decrease non-linearly to about +2.5-Volts through the operating life of the battery. This fact effectively adds an additional safety factor for the calculated battery life, because in use the actual average current values will all be somewhat lower than those specified above. Actual battery performance depends both on the peak as well as the average discharge current levels, and both these values are well within the range specified by the battery manufacturer with respect to the Cell Capacity (560 mA-hrs) used in the calculation above. Some of the timing assumptions for typically caregiver-determined changes of operating state in the above calculation (such as 12 minutes of uninterrupted alarm indication before each change) are likely rather conservative and could reasonably be modified to extend the calculated battery life specification to 2½ or even 3 years if such specification is deemed more appropriate based on further market research. Alternatively, the actual monitor unit internal electronic timing can be easily modified (such as by increasing the 3-second spacing, or by reducing the 0.1-second width of the alarm pulses) to achieve the same objective.

System Test Device

A diaper-simulating, test strip device 950, for use with the elinination-absorber monitoring system, is shown in FIG. 30A and FIG. 30B. The test strip has a substrate consisting of a thin tab 960, of electrically insulating material. Tab 960 has length and width similar to that of connector tab stiffener 166 of sensor 100 (as previously described), and can be made from the same material (such as 0.010-thick polyester sheet). This tab has a side 961 (illustrated in FIG. 30A), with a first area 964 of relatively electrically-conductive coating (such as thin, i.e., 0.001-inch, aluminum foil or other suitable material) disposed as shown. Side 961 also has a second area 965 of relatively electrically-conductive coating, which is separated from area 964 by an insulating gap 966. A chip resistor (or other device) 968 is preferably disposed on side 961, to bridge areas 964 and 965. Device 968 effectively simulates the value of conductivity that would be measured by monitor 500 (across channel 166, and thus between conductive strips 202 and 204 of a connected sensor 100), when a very small quantity of fecal matter is present in a sensor-equipped diaper. This device and its value (preferably a chip resistor, with value approximately 1.5–2.0 MegOhms, or other appropriate device such as a chip capacitor) are selected to have conductivity (as measured by the monitor) somewhat greater than, but approximately corresponding to, the minimum presentation of fecal matter required for monitor 500 to initiate alarm indications (as has been previously described). The tab's opposite side 962 (illustrated in FIG. 30B) has area 967 of relatively electrically-conductive coating, which is preferably equivalent in all aspects to first area coating 964 on side 961. Side 962 does not, however, have a conductive area corresponding to second area 965.

When substituted for sensor 100 (by simply being inserted into slot 600/610 of monitor 500), the test strip bridges contacts 620 and 622 in unit 500, thereby connecting power in the monitor circuit. Depending on which way the strip is inserted (i.e., which side is "up"), the strip also simulates either a "triggered" or "un-triggered" sensor. With this arrangement, only insertion of the test strip with side 961 "facing up" effectively connects device 968 between monitor contact 624 and contacts 620/622, thereby simulating the "triggered" state. The test strip is preferably provided with a pair distinctive indicative markings 971 and 972 on sides 961 and 962 respectively, so that the user can easily select the desired function. In a preferred embodiment, there also may be provided a suitable hole or opening 974 for the purpose of conveniently retaining the test strip device on a key-ring, thus providing quick access to, and avoiding loss of the relatively small test strip.

In an alternate embodiment, test strip 950 could have a single larger conductive area on side 961, combining areas 964 and 965 and thus eliminating gap 966, or areas 964 and 965 could be connected by a conductive trace or other shunt. Such arrangement would function similarly to the embodiment previously described, but would not verify the sensitivity of the system—rather only its more basic operational status. Alternatively, a test strip device could have suitable disposition of one or more conductive surfaces or reference devices corresponding to the function of side 961 substantially on one end, and at the other end (on the same side) have elements functionally corresponding to side 962, so that rotation of the strip end-for-end, instead of turning it over, would accomplish the same purpose. As will be readily apparent to those skilled in the relevant arts, various geometric shapes and orientations of relatively electrically-conductive and also relatively non-conductive surfaces could be alternatively disposed on, or within any suitable piece or assembly of material so as to appropriately simulate the connection of either a triggered or an un-triggered sensor, and thereby appropriately activate the monitor unit of an elimination-absorber monitoring system. Either the positional orientation of the test device and/or the monitor unit can be changed to allow a single device to simulate either sensor state, or alternatively two separate devices can be employed.

This simple and inexpensive device is useful in several use-environment situations, such as for demonstrating the alarm modes and "triggered" operation of the monitor to a new caregiver, or for verifying that foreign material (such as adhesive or dust) has not accumulated in the connector area of the monitor unit (to cause false triggering or prevent proper sensor connection), or that the connector spring or other means has not been bent or compromised so as to prevent proper connection to the sensor (and therefore requiring cleaning or replacement of a clip or other portion of the connector means).

Manufacture and Assembly
Manufacture and Assembly of Sensor 100

The materials employed in manufacture of sensor 100 are, to the extent possible, biodegradable, non-toxic, light, and readily available in large quantities. The various sensor embodiments can be manufactured by simple manual processes. For example, pre-punched layers can be aligned and affixed via the respective adhesive substrates, followed by wrapping with the protective peel-off cover. Alternatively and much preferably, high-speed, continuous strip production methods can be used. For example, the various layers can be assembled by: heat cured, co-reactive or catalyst cured adhesives, contact or pressure-sensitive adhesives, heat staking, hot-rolling or pressing, ultrasonic welding, induction heating (in the case of metallic strips), stapling, eyeleting, riveting and the like.

In one representative sequence, the component materials are provided already cut to width, perforated (in any or all cases) and spooled on large rolls, to be fed into the manufacturing process. The various layers can be pre-punched on the reel before assembly, or on the way to the joining point. Some or all of the components could be laminated between pressure rollers or plates into a continuous multi-layer strip, or alternatively, certain components or sub-assemblies could be fed as pre-cut components and "dropped" onto a moving substrate strip at the appropriate locations, prior to a final "cut-off" step for each finished unit.

Additional alternative embodiments of layer construction, other than those previously and specifically described, may be preferred to maximize the number of tape-like materials employed in the manufacturing process, to be continuously laminated from bulk supply reels prior to final cutoff of finished sensors, thereby minimizing lateral combination of precut piecewise materials but potentially inserting the requirement for selective adhesive application and/or bonding processes instead of, or in addition to, the use of prefabricated "double-sticky" tapes. In one preferred manufacturing process, the second double-sided adhesive layer 300 is the first component fed into the process. As mentioned previously, layer 300 can be supplied with adhesive already attached, or the adhesive(s) can be applied to suitable portions of both its surfaces as the first step, i.e., prior to attaching layers 250 and 350, but preferably after the perforations in layer 300 are punched or cut out, to avoid or minimize the production of sticky punched fragments. Holes 310 along the edges of layer 300 may advantageously (in addition to their other functions) serve as "sprocket holes" to facilitate the precise, high-speed transport of roll or sheet-fed sensors through the assembly process. Alternatively, the sensors could be laminated with several, or many units in parallel out of wider material rolls, with the final cut-off being more like a "cookie-cutter" operation than like a "taffy-cutter" one. In still another variation, some or all of the components could be "stack laminated" in a fixture, either "one-up" or "many-up" in large sheets.

Embodiments of sensor 100 that are intended for direct-incorporation into diapers can utilize any of the previously described variations of portion 450, either disposed on, or integrated with portion 474 on the front of the diapers. The in-diaper portion can be simply laminated into the diaper, either sequentially or simultaneously during the manufacturing process, with conventional diaper layers being suitably modified as is necessary.

The manufacturing process adjustments necessary to produce the various embodiments of sensor 100 will be apparent to those of ordinary skill in the art. Manufacture of the sensor embodiment that is incorporated as part of a disposable diaper, as opposed to an add-on to a diaper, will take account of the materials used and assembly process for that particular diaper. Alternatively, a separate and relatively complete sensor can simply be applied to the inner lining of a disposable diaper as a final step in an otherwise conventional diaper manufacturing process.

Manufacture and Assembly of Monitor 500

The monitor is manufactured using techniques that are standard in the electronics industry, for the processing of through-hole and/or surface-mount technology components on typical printed circuit board materials. In one example manufacturing sequence for a preferred embodiment as shown in FIG. 29A (and referring to FIG. 21A), all circuit components including lithium coin-cell BTY, including three sensor connector contact pin sockets 621, 623 and 625 (but excepting contact pins 620, 622 and 624), are mounted and/or soldered on a single, small (approximately 1.2 inch× 2.0 inch×0.06 inch thick) rigid printed circuit board 905 which, after assembly, soldering, cleaning and test, is "plugged" onto connector contact pins 620, 622 and 624 which have been previously inserted through molded plastic back case portion 514. These pins may be inserted and sealed in place by several methods, including press-fitting, hot-pressing, induction heating, ultrasonic welding, or insert-molding into the back case portion—or encapsulated via "potting" of the monitor case with a suitable waterproof filler such as epoxy resin or silicone rubber, thus simplifying reliable liquid-tight sealing of the assembly during its manufacture and also increasing its ruggedness. The heads of the contact pins are exposed in connector recess area 600, so that their shank portions protrude through, and continue into the interior of the case, passing through the plane of printed circuit board 905. The circuit board incorporates suitable miniature through-hole sockets 621, 623, and 625. These sockets are preferably of the gold-plated, wiping contact-spring type, to receive and reliably interconnect the contact pins. The fact that entire, fully-functional electronic circuit board assembly 910 comprises a single sub-unit that is independent of its case (and that can be easily tested and placed in inventory for later packaging) is a substantial advantage of this embodiment.

At this point, circuit assembly 910 is preferably held in place by suitable protruding and supporting features in the mating portions 512 and 514 of the case 510, then one or more of several standard coating/potting/sealing methods is used (such as epoxy resin or silicone injection) to both seal and mechanically protect the unit. The front case portion can be physically bonded to the back portion by the same process that seals and protects the case, or it can be separately attached by another process step such as ultrasonic welding. Alternatively, the internal "potting" or injection of other filling material (including inert gas or partial evacuation of the case) can be done either after, or simultaneously as, the two case portions are joined. Next, faceplate overlay 517 is adhered to the shallow aligning recess in the front face surface of upper case portion 512. Spring clip/plate 610 can be attached to recess 600 in back case portion 514 as a final step, or at any earlier time after the contact connector pins are inserted into the back case portion.

FIG. 29B illustrates an assembly sequence for an alternate version of monitor unit 500, that employs an edge-type embodiment of the flex-tab connector means as shown in FIG. 21B. In this situation, three flat edge-type contact springs 621-A, 623-A and 625-A are disposed on circuit board 905, and are designed to press securely against the shanks of contact pins 620, 622, and 624, when circuit assembly 910 is pressed into place inside back case portion 514. An alternative embodiment (to 610) of connector clip/plate 610-A is retained by a pair of dovetail slots 617 in case section 514. Other more detailed process variations potentially suitable for assembly of monitor/alarm 500 will no doubt be apparent to those skilled in the electronics manufacturing art, in light of these specifications.

Methods and Use
Application to a Disposable Diaper (Refer to FIG. 2A)

Sensor 100 is unwrapped from protective bottom cover 110, revealing lower adhesive 156 of layer 150 and exposed adhesive 456 on the bottom edges of layer 300, as well as adhesive 456 on the bottom of layer 452. Cover 110 is disposed of. Sensor 100 is positioned above a diaper, centering fold line 342 over the top front rim, with portion 450 extending over the outside front of the diaper. While stretching the diaper flat, the "inside-diaper" portion of sensor 100 is smoothed into place. The upper portion of sensor 100 that protrudes proximally over fold line 342 is adhered to (typically plastic-coated) section 474 of the diaper by adhesive 456. (This diaper can now be set aside for later use.)

Attachment of the Monitor/Alarm (Refer to FIG. 2B)

Top protective layer 455 is peeled off and discarded. Holding monitor unit 500 in one hand, connector tab 170 is inserted fully into slot 600/610 at the top edge of the monitor as the monitor is engaged with locating block 470. While holding monitor 500 in place, the end of translucent flap 460 is grasped and stretched firmly over the top of the unit. The proximal portion of the flap is then contacted with the exposed adhesive 304 exposed at the top front of the diaper, securing the monitor from tampering or removal.

Operation (Refer to FIG. 2B)

Using a finger tip, dot 702 on the face of monitor 500 (covering mode-change assembly 700) is momentarily pressed to select either the "beep" or the "blink" mode. If a "beep" is heard—the unit is set to beep; if indicating light 750 blinks in upper "balloon" symbol 518 on the monitor face—it is set to blink. Such response also verifies proper monitor operation and that sensor 100 is properly mated (and thus connected with) the monitor unit. The dot can be pressed again at any time to change the beep/blink mode. Subsequent automatic recurring activation of either audible or visual indicators means that a "diaper needs changing" condition exists.

Removal (Refer to FIG. 2B)

When changing diapers, to remove the monitor unit—edge of pull-tab 463 of translucent flap 460 of the sensor is grasped and pulled down away from the diaper. The monitor unit is lifted slightly (away from engagement with locating block 470) and it is slid straight downward—away from tab 170. The diaper and attached sensor pad are discarded as usual, and diaper monitor 500 is ready to be attached to a sensor on the next diaper.

EXAMPLE (The following example should not be considered as limiting the scope of the invention, but merely as being illustrative and representative thereof.)

Preliminary In-Use Effectiveness Tests and Summary of Results

The elimination-absorber monitoring system (shown in FIG. 2B) was initially use-tested in multiple two, three and four-day sessions with a healthy male child subject, beginning at age 8 months. The caregivers in these trials were the adult parents of the test subject. After the caregivers were given basic instruction in use of the system, prototype disposable sensors were unwrapped and applied to various popular brands and models typical of commercially available disposable diapers ("one-at-a-time", just before each diaper change) according to the "method of use" procedure as previously described. In each of the test sessions, approximately 20 disposable sensors were used, with each sensor being applied by one of the caregivers. Each sensor's performance (relative to the caregivers' expectations) was discussed and noted by an observer after the next change of diaper. Caregiver comments were also noted immediately after each application of the sensor and monitor to the diapers. The results of inspecting the soiled diapers (as well as any general observations by the caregivers during use of the system) were discussed and recorded after each change cycle. None of the test subject's or caregivers' routine activities were restricted or modified, other than by the application of sensor and removal/re-application of the monitor unit during diaper changes, and also by occasional activation of the monitor's "mode-switch" by the caregivers. Mode-switch activation was done to verify system operation after each diaper change, and to select either the audible or the visible alarm mode, as the caregivers desired from time to time. For example, the visible alarm mode was always selected for privacy (and confidentiality) when outside a controlled-access test facility.

In each instance, according to the caregivers, the system appeared to respond to the appropriate alarm criteria. There were, in fact, no observed clearly false positive or false negative responses. In reporting their conclusions after completion of the tests, the caregivers expressed the opinions that their use of the system had resulted in significantly improved convenience of care. In several instances, the caregivers also reported that use of the system had initiated more timely diaper changes than would likely have occurred with the typical frequency of their conventional checking methods. Moreover, the resulting monitor-suggested diaper change intervals appeared to otherwise closely replicate the expected "norm" as had been previously observed when only traditional methods were used. In summary, these tests demonstrated that the elimination-absorber monitoring system functioned as intended, in accordance with the criteria of the present specification.

Variations of the Disclosed Embodiments

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. Any such modifications are intended to be within the scope of the claims appended hereto. All patents and publications cited above are hereby incorporated by reference.

What is claimed is:

1. A sensor for use with an elimination-absorber monitoring system, said sensor comprising sensing means and a flow-baffling layer disposed to prevent said sensing means from detecting a liquid to be sensed until such liquid has flowed around said flow-baffling layer and into an elimination-absorber to such an extent that the elimination-absorber requires replacement.

2. The sensor of claim 1 comprising a first liquid-permeable flow-conducting layer disposed adjacent said flow-baffling layer on the side of said flow-baffling layer opposite said sensing means, to collect and conduct a liquid to be sensed across said flow-baffling layer.

3. The sensor of claim 2 comprising a second liquid-permeable flow-conducting layer, disposed opposite said first flow-conducting layer relative to said flow-baffling layer, to conduct liquid from said first flow-conducting layer, around said flow-baffling layer and toward said sensing means.

4. The sensor of claim 3 comprising a first series of openings through and disposed toward the outer edges of said flow-baffling layer to conduct liquid from said first flow-conducting layer, through said flow-baffling layer and to said second flow-conducting layer.

5. The sensor of claim 4 comprising a second series of openings through said flow-baffling layer, disposed between said first series of openings and the outer edges of said flow-baffling layer to conduct liquid from said first flow-conducting layer, through said flow-baffling layer, to the elimination-absorber.

6. The sensor of claim 3 comprising a relatively liquid-impermeable layer disposed opposite said flow-baffling layer with respect to said sensing means and said second flow-conducting layer to form a capillary channel within said sensing means.

7. The sensor of claim 6 comprising:

a first series of openings through and disposed toward the outer edges of said flow-baffling layer to conduct liquid from said first flow-conducting layer, through said flow-baffling layer and to said second flow-conducting layer, and a second series of openings through said flow-baffling layer, disposed between said first series of openings and the outer edges of said flow-baffling layer to conduct liquid from said first flow-conducting layer, through said flow-baffling layer, to the elimination-absorber, wherein said second flow-conducting layer is sufficiently wide to communicate with said first flow-conducting layer through said first series of openings, but not through said second series of openings, and being disposed between said flow-baffling layer and said sensing means, and said relatively liquid-impermeable layer is sufficiently wide to preclude direct flow between said sensing means and the elimination-absorber.

8. The sensor of claim 1 comprising a series of openings through said flow-baffling layer of sufficient size and shape to permit the passage of fecal matter to contact said sensing means, while deterring contact between said sensing means and the skin of a wearer of the elimination-absorber.

9. The sensor of claim 8 wherein said openings are disposed posterior to the sensor portion most likely to be directly impacted by a drop or stream of urine.

10. The sensor of claim 7 comprising a third series of openings through said flow-baffling layer of sufficient size and shape to permit the passage of fecal matter to contact said sensing means while, when taken together with the thickness of said layers, deterring contact between said sensing means and the skin of a wearer of the elimination-absorber, said third series of openings being disposed posterior to the sensor portion most likely to be directly impacted by a drop or stream of urine, there being no liquid conduction between said first flow-conducting layer and said second flow-conducting layer or said sensing means through said third series of openings.

11. The sensor of claim 10 wherein said sensor is incorporated as part of a disposable diaper.

12. The sensor of claim 10 wherein said sensor is adapted for application to an elimination-absorber, comprising:

means for affixing said sensor to the elimination-absorber, and an optional cover layer for separating said first flow-conducting layer from the skin of a wearer of the elimination-absorber.

13. The sensor of claim 3 wherein said second flow-conducting layer is selected from a material that is less absorbent than a dry elimination-absorber, but more absorbent than an elimination-absorber sufficiently wetted to require replacement.

14. The sensor of claim 3 wherein said second flow-conducting layer is configured in size and materials to delay the conduct of the liquid from the first conducting-layer to the sensing means until the elimination-absorber is sufficiently wetted to require replacement.

15. The sensor of claim 11 further comprising a monitor/alarm unit retainer, said retainer comprising:

an interlocking protruding or receiving portion corresponding with a mating portion on an elimination-absorber monitor, and an elastic or semi-elastic flap adapted to be stretched over a monitor/alarm unit, said flap being permanently attached at a distal end to said sensor or said elimination-absorber, and having a proximal end a portion of which is adapted to be releaseably adhered to said sensor, said elimination-absorber, or to another portion of said flap.

16. The sensor of claim 12 further comprising a monitor/alarm unit retainer, said retainer comprising:

an interlocking protruding or receiving portion, corresponding with a mating portion on an elimination-absorber monitor, having adhesive means for attachment to the elimination-absorber, and an elastic or semi-elastic flap adapted to be stretched over a monitor/alarm unit, said flap pending from the distal end of said protruding or receiving portion and having a proximal end, a portion of which is adapted to be releaseably adhered to said sensor or said elimination-absorber.

17. The sensor of claim 15 further comprising a releasable circuit electrical connector, said connector comprising a flexible tab portion adapted to be received in a tab-receiving portion of an elimination-absorber monitor, said tab portion having two or more conductive members of said sensing means disposed on a resilient support.

18. The sensor of claim 17 wherein said tab portion is disposed through a front surface of said diaper above said interlocking protruding or receiving portion.

19. The sensor of claim 16 further comprising a releasable circuit electrical connector, said connector comprising a flexible tab portion adapted to be received in a tab-receiving portion of an elimination-absorber monitor, said tab portion having two or more conductive members of said sensing means disposed on a resilient support.

20. An elimination-absorber monitoring system kit comprising:

a sensor of claim 17,
a monitor/alarm unit comprising:
a power source,
an alarm means,
an interlocking protruding or receiving portion corresponding with the portion on said monitor/alarm unit retainer,
a releasable sensor Connector comprising a tab-receiving portion having two or more protruding contacts arranged to engage said conductive members, lateral surfaces for guiding and positioning said tab, and having means to deform said resilient support thereby retaining said tab portion while maintaining its orientation and pressure against said contacts to ensure continuous electrical connection of said conductive members with said contacts, and
electronic circuitry employing relatively narrow, relatively low duty-cycle pulses to measure conductivity or capacitance between a pair of spaced conductors or semiconductors that are disposed within or that span an appropriate measurement path relative to the elimination-absorber to be monitored and actuates said alarm means when the elimination-absorber requires replacement.

21. An elimination-absorber monitoring system kit comprising:

a sensor of claim 19,
a monitor/alarm unit comprising:
a power source,
an alarm means,
an interlocking protruding or receiving portion corresponding with the portion on said monitor/alarm unit retainer,
a releasable sensor connector comprising a tab-receiving portion having two or more protruding contacts arranged to engage said conductive members, lateral surfaces for guiding and positioning said tab, and having means to deform said resilient support thereby retaining said tab portion while maintaining its orientation and pressure against said contacts to ensure continuous electrical connection of said conductive members with said contacts, and
electronic circuitry employing relatively narrow, relatively low duty-cycle pulses to measure conductivity or capacitance between a pair of spaced conductors or semiconductors that are disposed within or that span an appropriate measurement path relative to the elimination-absorber to be monitored and actuates said alarm means when the elimination-absorber.

22. The sensor of claim 1 comprising a cover layer disposed on the side of said flow-baffling layer farthest from said sensing means, and a liquid-permeable flow-conducting layer disposed on the side of said flow-baffling layer closest to said sensing means to conduct liquid around said flow-baffling layer and toward said sensing means.

23. The sensor of claim 22 further comprising a relatively liquid-impermeable layer disposed opposite said sensing means with respect to said flow-baffling layer.

24. A sensor for use with an elimination-absorber monitoring system, said sensor comprising a layer, sensing means disposed beneath said layer and a series of openings through said layer, said openings being of sufficient size, shape and thickness to permit the passage of fecal matter to contact said sensing means, while deterring contact between said sensing means and the skin of a wearer of the elimination-absorber.

25. The sensor of claim 24 wherein each of said openings is disposed posterior to the sensor portion most likely to be directly impacted by a drop or stream of urine.

26. The sensor of claim 25 wherein said layer is sufficiently absorbent to retain and thereby prevent small volumes of liquid or condensation from penetrating said openings and being detected by said sensing means.

27. The sensor of claim 26 further comprising a relatively liquid-impermeable layer disposed above, below or within said absorbent layer, said openings being continuous through said absorbent and liquid-impermeable layers.

28. The sensor of claim 27 wherein said liquid-impermeable layer is relatively hydrophobic as compared to said absorbent layer even when said absorbent material becomes saturated.

29. The sensor of claim 27 wherein said absorbent layer is bounded by said liquid-impermeable layer to direct the flow of liquid away from said openings.

30. The sensor of claim 24 further comprising a cover layer disposed adjacent said layer opposite said sensing means, said cover layer having nominally closed slits/flaps covering said openings, said slits/flaps being resistant to passage of urine but displaceable by contact with feces to permit the passage of fecal matter into the openings.

31. A monitor/alarm unit retainer for use with an elimination-absorber monitoring system having an elimination-absorber/sensor unit and a monitor/alarm unit, said retainer comprising:

an elastic or semi-elastic flap adapted to be stretched over said monitor/alarm unit, said flap having a monitor/alarm unit contacting portion that is substantially free of adhesive, said monitor/alarm unit contacting portion being at least partially surrounded by second portion having sufficient adhesive for retention on an elimination-absorber, thereby facilitating ready and clean release of the monitor/alarm unit from the retainer when desired; and a locating block and a reciprocally shaped receiving portion disposed respectively on said elimination-absorber/sensor unit or said monitor/alarm unit to prevent movement of said monitor/alarm unit and maintain alignment between protruding tab and barbless receiving slot connection means of said units while said flap is stretched over said elimination-absorber/sensor unit.

32. A releasable electrical circuit connector, said connector comprising a flexible tab portion and a tab-receiving portion,
   said tab portion having two or more conductive members disposed on a resilient support, and
   said tab-receiving portion having two or more protruding contacts arranged to complete a circuit with said conductive members, lateral surfaces for guiding and positioning said tab, and having means to deform said resilient support into a substantially wave-like cross-section thereby releaseably retaining said tab portion, such deformation of said resilient support maintaining said tab portion's orientation and pressure against said contacts to ensure continuous electrical connection of said conductive members with said contacts.

33. A monitor/alarm unit for use with an elimination-absorber monitoring system, said monitor/alarm unit comprising:
   a power source,
   an alarm means,
   a releasable sensor connector, and
   electronic circuitry employing directly driven, relatively narrow, relatively low duty-cycle pulses applied directly across a pair of spaced conductors or semiconductors that are disposed within or that span an appropriate measurement path relative to the elinination-absorber to be monitored, to measure conductivity or capacitance therebetween and actuate said alarm means when the elimination-absorber requires replacement.

34. The monitor/alarm unit of claim 33 wherein the sensor is not subjected by the monitor circuit to substantially any impressed voltage during the time between sensing pulses, so that the electrically charged ions in the material to be sensed can tend to return to their original random distribution between such pulses, and wherein the sensing pulses have relatively fast rise/fall-times substantially shorter than their widths.

35. The monitor/alarm unit of claim 33 wherein repetitive initiation of said alarm means when activated is relatively synchronous with said sensing pulses, or is related to the sensing signal repetition rate via a common master clock frequency from which the respective repetition rates are derived.

36. The monitor/alarm of claim 33 wherein the sensing pulses applied to connecting conductors of a sensor are connected in common with one side of the power source, so that complete disconnection of circuit power can be accomplished by a single additional contact to one of the sensor's connecting conductors or semiconductors.

37. The monitor/alarm of claim 33 further comprising:
   a waterproof case enclosing said power source, said alarm means, said electronic circuitry, said releasable sensor connector being fabricated as part of said case, said case having control surfaces with access for said alarm means and control means, said access being sealed by a thin, at least partially flexible membrane,
   visible alarm means comprising an electro-optical source disposed in a through-opening in said control surface, said through opening being sealed by a relatively thin, substantially optically-permeable covering,
   audible alarm means comprising a shallow recess in said case disposed behind an audibly transmissive, relatively thin flexible membrane with said recess having a sound permeable, structurally supportive, relatively rigid, perforated bottom, said recess allowing said membrane to vibrate freely in response to acoustic pressure waves from the outermost vibrating member of an electro-acoustic transducer disposed within said case but whereby said bottom limits the maximum deflection of said membrane to within its elastic limit thereby protecting said membrane from mechanical damage without excessively attenuating the sound transmission from said transducer during intended operation, and,
   control means disposed through a surface of said case that both changes and indicates the alarm or indicative function selected for the system's operation in response to actuation of said control means, where said indication is by means of activating the visible or audible alarm to emit a representative signal, said control means providing such indication only upon proper connection of an elimination-absorber sensor through said releasable sensor connector.

38. An elimination-absorber monitoring system comprising monitoring means and an electronic monitor/alarm unit releaseably attachable to said elimination-absorber, said monitor/alarm unit comprising:
   a power source, alarm means, electronic elimination-absorber monitoring means wherein said monitoring means actuates said alarm means when the elimination-absorber requires replacement, and wherein said alarm means comprises both an audible and a visible/silent indicative mode for purposes of alarm indication, and
   a single control means which, upon actuation both;
      (a) causes a change in said indicative mode employed by said monitor/alarm unit, from said audible to said visible/silent mode and vice-versa, and
      (b) substantially simultaneous with actuation causes said monitor unit to produce an audible or visible/silent representative alarm indication demonstrating the mode selected and verifying said change.

39. The elimination-absorber monitoring system of claim 38, wherein said monitor/alarm unit further comprises attachment-controlled switching means whereby the on/off operation of said monitor/alarm unit and the switching of said power source are controlled by the mating or attachment of said monitor/alarm unit to said monitoring means.

40. The elimination-absorber monitoring system of claim 38, wherein said representative alarm indication further demonstrates or verifies the proper operable connection of said monitor to said sensor.

41. A fluid-sealed or contaminant-resistant audible signal transmission means for the enclosure of an electronic device, said signal transmission means comprising:
   a shallow recess in said enclosure disposed behind an audibly transmissive, relatively thin flexible sealing membrane with said recess having a sound permeable, structurally supportive, relatively rigid, perforated bottom, said recess allowing said membrane to vibrate freely in response to acoustic pressure waves traveling either to or from the outermost vibrating member of an electro-acoustic transducer disposed within said enclosure, but whereby said bottom limits the maximum deflection of said membrane to within its elastic limit, thereby protecting said membrane from mechanical damage without excessively attenuating the sound transmission to or from said transducer during intended operation.

42. A test device for use with an elimination-absorber monitoring system, said system comprising: a sensor, and an electronic monitor/alarm unit releaseably connectable to said sensor, and said monitor/alarm unit comprising: a power source, an alarm means, a releasable sensor connector and electronic means to measure conductivity or capacitance between a pair of spaced conductors or semiconductors that are disposed within or that span an appropriate measurement path relative to the elimination-absorber to be monitored and wherein said electronic means actuates said alarm means when the elimination-absorber requires replacement, said test device comprising:

a support, two or more conductive contacts disposed on said support whereby said contacts are releaseably connectable to said electronic means of said monitor/alarm unit by means of engagement of said support with said sensor connector, a circuit disposed on said support and communicating with said contacts whereby the relative physical orientation of the support upon its engagement with said monitor/alarm unit substantially determines the conductivity or capacitance presented by said test device to said electronic means, said test device thereby simulating either a relatively unsoiled or soiled elimination-absorber, respectively.

43. The test device of claim 42 further comprising circuitry disposed on said support and communicating with said contacts whereby said circuitry connects said power source within said monitor/alarm unit upon engagement of said test device with said sensor connector regardless of which orientation of said test device is selected for said engagement.

* * * * *